US007812135B2

(12) United States Patent
Smith et al.

(10) Patent No.: US 7,812,135 B2
(45) Date of Patent: Oct. 12, 2010

(54) GITR-BINDING ANTIBODIES

(75) Inventors: L. Mary Smith, Dedham, MA (US); Grazyna Szymanska, Dedham, MA (US); Paul Ponath, San Francisco, CA (US); Michael Rosenzweig, Boston, MA (US); Jose F. Ponte, South Boston, MA (US)

(73) Assignee: TOLERRX, Inc., Cambridge, MA (US)

( * ) Notice: Subject to any disclaimer, the term of this patent is extended or adjusted under 35 U.S.C. 154(b) by 0 days.

(21) Appl. No.: 11/389,880

(22) Filed: Mar. 27, 2006

(65) Prior Publication Data
US 2007/0098719 A1 May 3, 2007

Related U.S. Application Data

(60) Provisional application No. 60/665,322, filed on Mar. 25, 2005, provisional application No. 60/687,265, filed on Jun. 3, 2005.

(51) Int. Cl.
C07K 16/00 (2006.01)
C12P 21/08 (2006.01)
A61K 39/395 (2006.01)

(52) U.S. Cl. .............. 530/388.1; 530/387.1; 530/387.3; 530/388.15; 530/388.22; 424/130.1

(58) Field of Classification Search .................. None
See application file for complete search history.

(56) References Cited

U.S. PATENT DOCUMENTS

| 4,399,216 | A | 8/1983 | Axel et al. |
|---|---|---|---|
| 4,444,878 | A | 4/1984 | Paulus |
| 4,510,245 | A | 4/1985 | Cousens et al. |
| 4,634,665 | A | 1/1987 | Axel et al. |
| 4,683,195 | A | 7/1987 | Mullis et al. |
| 4,683,202 | A | 7/1987 | Mullis |
| 4,704,362 | A | 11/1987 | Itakura et al. |
| 4,741,900 | A | 5/1988 | Alvarez et al. |
| 4,745,055 | A | 5/1988 | Schenk et al. |
| 4,800,159 | A | 1/1989 | Mullis et al. |
| 4,816,397 | A | 3/1989 | Boss et al. |
| 4,816,567 | A | 3/1989 | Cabilly et al. |
| 4,965,188 | A | 10/1990 | Mullis et al. |
| 4,968,615 | A | 11/1990 | Koszinowski et al. |
| 5,168,062 | A | 12/1992 | Stinski |
| 5,179,017 | A | 1/1993 | Axel et al. |
| 5,225,539 | A | 7/1993 | Winter |
| 5,304,489 | A | 4/1994 | Rosen |
| 5,530,101 | A | 6/1996 | Queen et al. |
| 5,569,825 | A | 10/1996 | Lonberg et al. |
| 5,585,089 | A | 12/1996 | Queen et al. |
| 5,585,097 | A | 12/1996 | Bolt et al. |
| 5,589,369 | A | 12/1996 | Seidman et al. |
| 5,591,669 | A | 1/1997 | Krimpenfort et al. |
| 5,658,570 | A | 8/1997 | Newman et al. |
| 5,693,761 | A | 12/1997 | Queen et al. |
| 5,693,762 | A | 12/1997 | Queen et al. |
| 5,693,780 | A | 12/1997 | Newman et al. |
| 5,741,957 | A | 4/1998 | Deboer et al. |
| 5,756,096 | A | 5/1998 | Newman et al. |
| 5,811,524 | A | 9/1998 | Brams et al. |
| 5,837,821 | A | 11/1998 | Wu |
| 5,849,992 | A | 12/1998 | Meade et al. |
| 5,892,019 | A | 4/1999 | Schlom et al. |
| 5,939,598 | A | 8/1999 | Kucherlapati et al. |
| 5,959,083 | A | 9/1999 | Bosslet et al. |
| 5,969,108 | A | 10/1999 | McCafferty et al. |
| 6,075,181 | A | 6/2000 | Kucherlapati et al. |
| 6,111,090 | A | 8/2000 | Gorman et al. |
| 6,150,584 | A | 11/2000 | Kucherlapati et al. |
| 6,180,370 | B1 | 1/2001 | Queen et al. |
| 6,420,140 | B1 | 7/2002 | Hori et al. |
| 6,458,592 | B1 | 10/2002 | Jakobovits et al. |
| 6,476,198 | B1 | 11/2002 | Kang |
| 6,503,184 | B1 | 1/2003 | Ni et al. |
| 6,509,173 | B1 | 1/2003 | Ni et al. |
| 6,689,607 | B2 | 2/2004 | Ni et al. |

(Continued)

FOREIGN PATENT DOCUMENTS

EP 0 068 763 4/1987

(Continued)

OTHER PUBLICATIONS

Balint, Robert F. et al., "Antibody engineering by parsimonious mutagenesis," *Gene*, vol. 137:109-118 (1993).
Davies, Julian et al., "Affinity improvement of single antibody VH domains: residues in all three hypervariable regions affect antigen binding," *Immunotechnology*, vol. 2:169-179 (1996).
Holt, Lucy J. et al., "Domain antibodies: proteins for therapy," *Trends in Biotechnology*, vol. 21(11):484-490 (2003).
Hwang, W.Y. et al., "Use of human germline genes in a CDR homology-based approach to antibody humanization," *Methods*, vol. 36(1):35-42 (2005).

(Continued)

Primary Examiner—Robert Landsman
(74) Attorney, Agent, or Firm—Fish & Richardson P.C.

(57) ABSTRACT

The present invention provides binding molecules that specifically bind to GITR, e.g., human GITR (hGITR), on T cells and dendritic cells. Binding molecules of the invention are characterized by binding to hGITR with high affinity, in the presence of a stimulating agent, e.g., CD3, are agonistic, and abrogate the suppression of Teff cells by Treg cells. Various aspects of the invention relate to binding molecules, and pharmaceutical compositions thereof, as well as nucleic acids, recombinant expression vectors and host cells for making such binding molecules. Methods of using a binding molecule of the invention to detect human GITR or to modulate human GITR activity, either in vitro or in vivo, are also encompassed by the invention.

27 Claims, 13 Drawing Sheets

U.S. PATENT DOCUMENTS

| | | | |
|---|---|---|---|
| 7,025,962 | B1 | 4/2006 | Gorman et al. |
| 2002/0103345 | A1 | 8/2002 | Zhu |
| 2002/0150993 | A1 | 10/2002 | Ashkenazi et al. |
| 2003/0133936 | A1 | 7/2003 | Byrne et al. |
| 2003/0138426 | A1 | 7/2003 | Ni et al. |
| 2003/0153499 | A1 | 8/2003 | Ni et al. |
| 2004/0157786 | A1 | 8/2004 | Bissery |
| 2005/0014224 | A1 | 1/2005 | Collins et al. |
| 2005/0048054 | A1 | 3/2005 | Hanabuchi et al. |
| 2005/0069983 | A1 | 3/2005 | Ashkenazi et al. |
| 2005/0180971 | A1 | 8/2005 | Ashdown |
| 2005/0202008 | A1 | 9/2005 | Williams et al. |
| 2005/0238628 | A1 | 10/2005 | Blau |
| 2006/0002932 | A1 | 1/2006 | Vieweg |
| 2006/0051350 | A1 | 3/2006 | van Oosterhout et al. |
| 2006/0057111 | A1 | 3/2006 | Hedlund et al. |
| 2006/0099171 | A1 | 5/2006 | Tone et al. |
| 2006/0134102 | A1 | 6/2006 | LePage et al. |
| 2006/0135756 | A1 | 6/2006 | Gorman et al. |
| 2006/0141573 | A1 | 6/2006 | Ashkenazi et al. |
| 2006/0281146 | A1 | 12/2006 | Bodary et al. |
| 2007/0098719 | A1 | 5/2007 | Smith et al. |
| 2007/0178093 | A1 | 8/2007 | Hanabuchi et al. |
| 2007/0184444 | A1 | 8/2007 | Abbas et al. |
| 2007/0185017 | A1 | 8/2007 | Aggarwal et al. |
| 2008/0220000 | A1 | 9/2008 | Moore et al. |

FOREIGN PATENT DOCUMENTS

| | | |
|---|---|---|
| EP | 0 255 694 | 2/1988 |
| EP | 0 125 023 | 6/1991 |
| EP | 0 120 694 | 7/1993 |
| EP | 0 368 684 | 3/1994 |
| EP | 0 266 663 | 1/1995 |
| EP | 0 256 654 | 9/1996 |
| EP | 0920505 B1 | 6/1999 |
| EP | 1196186 B1 | 4/2002 |
| WO | WO 87/02671 | 5/1987 |
| WO | WO 88/03559 | 5/1988 |
| WO | WO 88/03565 | 5/1988 |
| WO | WO 90/07861 | 7/1990 |
| WO | WO 92/22653 | 12/1992 |
| WO | WO 94/09817 | 5/1994 |
| WO | WO-98/24895 A1 | 6/1998 |
| WO | WO-99/40196 A1 | 8/1999 |
| WO | WO 00/06605 | 2/2000 |
| WO | WO 00/37504 | 6/2000 |
| WO | WO 00/58499 | 10/2000 |
| WO | WO 00/76310 | 12/2000 |
| WO | WO 02/02781 | 1/2002 |
| WO | WO-03/006058 A1 | 1/2003 |
| WO | WO-03/009865 A1 | 2/2003 |
| WO | WO-03/049758 A1 | 6/2003 |
| WO | WO-2004/084942 A2 | 10/2004 |
| WO | WO-2004/107618 A2 | 12/2004 |
| WO | WO 2005/007190 | 1/2005 |
| WO | WO-2005/007190 A1 | 1/2005 |
| WO | WO-2006/078911 A2 | 7/2006 |
| WO | WO-2006/132272 A1 | 12/2006 |
| WO | WO-2007/084775 A2 | 7/2007 |
| WO | WO-2007/133822 A1 | 11/2007 |

OTHER PUBLICATIONS

Imgenex, "Monoclonal Antibody GITR (Clone DTA-1) FITC Conjugate," retrieved online at: http://www.imgenex.com/antibody_details.php?catalog=IMG-5920C (2007).

Kanamaru, Fumiko et al., "Costimulation via Glucocorticoid-Induced TNF Receptor in Both Conventional and CD25+ Regulatory CD4+ T Cells," *The Journal of Immunology*, vol. 172:7306-7314 (2004).

Kohm, Adam P. et al., "Cutting Edge: Ligation of the Glucocorticoid-Induced TNF Receptor Enhances Autoreactive CD4+ T Cell Activation and Experimental Autoimmune Encephalomyelitis," *The Journal of Immunology*, vol. 172:4686-4690 (2004).

Little, M. et al., "Of mice and men: hybridoma and recombinant antibodies," *Immunol. Today*, vol. 21(8):364-370 (2000).

McHugh, Rebecca S. et al., "CD4+CD25+ Immunoregulatory T Cells: Gene Expression Analysis Reveals a Functional Role for the Glucocorticoid-Induced TNF Receptor," *Immunity*, vol. 16:311-323 (2002).

Nocentini, Giuseppe et al., "A new member of the tumor necrosis factor/nerve growth factor receptor family inhibits T cell receptor-induced apoptosis," *Proc. Natl. Acad. Sci. USA*, vol. 94:6216-6221 (1997).

R&D Systems, "Monoclonal, Anti-human GITR/TNFRSF18 Antibody," Catalog No. MAB689 (2002).

R&D Systems, "Monoclonal, Anti-mouse GITR/TNFRSF18 Antibody," Catalog No. MAB5241 (2006).

Ronchetti, Simona et al., "GITR, a member of the TNF receptor superfamily, is costimulatory to mouse T lymphocyte subpopulations," *Eur. J. Immunol.*, vol. 34:613-622 (2004).

Shimizu, Jun et al., "Stimulation of $CD25^{30}$ CD4+ regulatory T cells through GITR breaks immunological self-tolerance," *Nature Immunology*, vol. 3(2):135-142 (2002).

Stephens, Geoffrey L. et al., "Engagement of Glucocorticoid-Induced TNFR Family-Related Receptor on Effector T Cells by its Ligand Mediates Resistance to Suppression by CD4+CD25+ T Cells," *The Journal of Immunology*, vol. 173:5008-5020 (2004).

Tone, Masahide et al., "Mouse glucocorticoid-induced tumor necrosis factor receptor ligand is costimulatory for T cells," *PNAS*, vol. 100(25):15059-15064 (2003).

International Preliminary Report on Patentability for Application No. PCT/US2006/011114, dated Sep. 25, 2007.

GenBank Accession No. gi40354198 dated Sep. 3, 2007.

GenBank Accession No. gi23238190 dated Apr. 11, 2010.

GenBank Accession No. gi23238193 dated Apr. 11, 2010.

GenBank Accession No. gi23238196 dated Apr. 19, 2010.

Adelman et al., "In Vitro Deletional Mutagenesis for Bacterial Production of the 20,000-Dalton Form of Human Pituitary Growth Hormone," *DNA*, 1983, 2(3):183-193.

Amit et al., "Three-Dimensional Structure of an Antigen-Antibody Complex at 2.8 Å Resolution," *Science*, 1986, 233:747-753.

Arthur and Mason, "T Cells That Help B Cell Responses To Soluble Antigen Are Distinguishable from Those Producing Interleukin 2 on Mitogenic or Allogeneic Stimulation," *J Exp Med*, 1986, 163:774-786.

Askari and McDonnell, "Antisense-oligonucleotide therapy," *N Eng J Med*, 1996, 334:316-318.

Barbas III et al., "Semisynthetic combinatorial antibody libraries: a chemical solution to the diversity problem," *Proc Natl Acad Sci USA*, 1992, 89(10):4457-4461.

Benhar and Pastan, "Cloning, expression and characterization of the Fv fragments of the anti-carbohydrate mAbs B1 and B5 as single-chain immunotoxins," *Protein Eng*, 1994, 7(12):1509-1515.

Bennett and Schwartz, "Antisense therapy for angioplasty restenosis. Some critical considerations," *Circulation*, 1995, 92(7):1981-1983.

Berenbaum, "Synergy, additivism and antagonism in immunosuppression," *Clin. Exp. Immunol.*, 1977, 28:1-18.

Biacore X100—Readily accessible protein interaction analysis—in your lab, GE Healthcare, 2007.

Bird et al., "Single-Chain Antigen-Binding Proteins," *Science*, 1988, 242:423-426.

Boder et al., "Directed evolution of antibody fragments with monovalent femtomolar antigen-binding affinity," *Proc Natl Acad Sci USA*, 2000, 97(20):10701-10705.

Boder and Wittrup, "Yeast surface display for screening combinatorial polypeptide libraries," *Nat Biotechnol*, 1997, 15(6):553-557.

Bushman, "RNA interference: applications in vertebrates," *Mol Ther*, 2003, 7:9-10.

Byrn et al., "Biological properties of a CD4 immunoadhesin," *Nature*, 1990, 344:667-670.

Cadwell and Joyce, "Randomization of genes by PCR mutagenesis," *PCR Meth Appl*, 1992, 2:28-33.

Cadwell and Joyce, "Mutagenic PCR," *PCR Meth Appl*, 1994, 3(6):S136-S140.
Casset et al., "A peptide mimetic of an anti-CD4 monoclonal antibody by rational design," *Biochem Biophys Res Commun*, 2003, 307:198-205.
Chamow and Ashkenazi, "Immunoadhesins: principles and applications," *Trends Biotechnol*, 1996,14:52-60.
Cheung et al., "Epitope-Specific Antibody Response to the Surface Antigen of Duck Hepatitis B Virus in Infected Ducks," *Virology*, 1990, 176:546-552.
Chothia and Lesk, "Canonical Structures for the Hypervariable Regions of Immunoglobulins," *J Mol Biol*, 1987, 196:901-917.
Clackson et al., "Making antibody fragments using phage display libraries," *Nature*, 1991, 352:624-628.
Co et al., "Chimeric and humanized antibodies with specificity for the CD33 antigen," *J Immunol*, 1992, 148:1149-1154.
Connolly, "Analytical Molecular Surface Calculation," *J Appl Cryst*, 1983, 16:548-558.
Cottrell and Doering, "Silence of the strands: RNA interference in eukaryotic pathogens," *Trends Microbiol*, 2003, 11:37-43.
Daugherty et al., "Flow cytometric screening of cell-based libraries," *J Immunol Meth*, 2000, 243:211-227.
de Kruif et al., "Selection and application of human single chain Fv antibody fragments from a semi-synthetic phage antibody display library with designed CDR3 regions," *J Mol Biol*, 1995, 248:97-105.
Delgado et al., "Enhanced tumour specificity of an anti-carcinoembrionic antigen Fab' fragment by poly (ethylene glycol) (PEG) modification," *Br J Cancer*, 1996, 73(2):175-182.
Falkner and Zachau, "Expression of mouse immunoglobulin genes in monkey cells," *Nature*, 1982, 298:286-288.
Finkelman et al., "IL-4 is required to generate and sustain in vivo IgE responses," *J Immunol*, 1988, 141:2335-2341.
Francisco et al., "Production and fluorescence-activated cell sorting of *Escherichia coli* expressing a functional antibody fragment on the external surface," *Proc Natl Acad Sci USA*, 1993, 90(22):10444-10448.
Gautier et al., "α-DNA IV: α-anomeric and β-anomeric tetrathymidylates covalently linked to intercalating oxazolopyridocarbazole. Synthesis, physicochemical properties and poly (rA) binding," *Nucl Acids Res*, 1987, 15(16):6625-6641.
Georgiou et al., "Display of heterologous proteins on the surface of microorganisms: from the screening of combinatorial libraries to live recombinant vaccines," *Nat Biotechnol*, 1997, 15:29-34.
Goding, *Monoclonal Antibodies: Principles and Practice*, 1986, pp. 59-103.
Griffiths and Duncan, "Strategies for selection of antibodies by phage display," *Curr Opin Biotechnol*, 1998, 9:102-108.
Griffiths et al., "Isolation of high affinity huan antibodies directly from large synthetic repertoires," *EMBO J*, 1994, 13:3245-3260.
Gurney et al., "Identification of a new member of the tumor necrosis factor family and its receptor, a human ortholog of mouse GITR," *Curr Biol*, 1999, 9:215-218.
Hanes et al., "Picomolar affinity antibodies from a fully synthetic naïve library selected and evolved by ribosome display," *Nat Biotechnol*, 2000, 18:1287-1292.
Hanes et al., "Ribosome display efficiently selects and evolves high-affinity antibodies in vitro from immune libraries," *Proc Natl Acad Sci USA*, 1998, 95(24):14130-14135.
Hanes and Plückthun, "In vitro selection methods for screening of peptide and protein libraries," *Curr Top Microbiol Immunol*, 1999, 243:107-122.
He and Taussig, "Antibody-ribosome-mRNA (ARM) complexes as efficient selection particles for in vitro display and evolution of antibody combining sites," *Nucl Acids Res*, 1997, 25(24):5132-5134.
Ho et al., "Site-directed mutagenesis by overlap extension using the polymerase chain reaction," *Gene*, 1989, 77:51-59.
Hoogenboom and Chames, "Natural and designer binding sites made by phage display technology," *Immunol Today*, 2000, 21(8):371-378.
Hoogenboom et al., "Antibody phage display technology and its applications," *Immunotechnol*, 1998, 4:1-20.
Hoogenboom and Winter, "By-passing Immunisation. Human Antibodies from Synthetic Repertoires of Germline $V_H$ Gene Segments Rearranged in Vitro," *J Mol Biol*, 1992, 227(2):381-388.

Horton et al., "Gene splicing by overlap extension," *Meth Enzymol*, 1993, 217:270-279.
Huie et al., "Antibodies to human fetal erythroid cells from a nonimmune phage antibody library," *Proc Natl Acad Sci USA*, 2001, 98:2682-2687.
Huse et al., "Generation of a Large Combinatorial Library of the Immunoglobulin Repertoire in Phage Lambda," *Science*, 1989, 2476:1275-1281.
Huston et al., "Protein engineering of antibody binding sites: recovery of specific activity in an anti-digoxin single-chain Fv analogue produced in *Escherichia coli*," *Proc Natl Acad Sci USA*, 1988, 85:5879-5883.
Inoue et al., "Synthesis and hybridization studies on two complementary nona(2'-O-methyl) ribonucleotides," *Nucl Acids Res*, 1987, 15(15):6131-6148.
Inoue et al., "Sequence-dependent hydrolysis of RNA using modified oligonucleotide splints and RNase H," *FEBS Lett*, 1987, 215(2):327-330.
Irving et al., "Ribosome display and affinity maturation: from antibodies to single V-domains and steps towards cancer therapeutics," *J Immunol Meth*, 2001, 248:31-45.
Jendreyko et al., "Intradiabodies, Bispecific, Tetravalent Antibodies for the Simultaneous Functional Knockout of Two Cell Surface Receptors," *J Biol Chem*, 2003, 278(48):47812-47819.
Jones et al., "Replacing the complementarity-determining regions in a human antibody with those from a mouse," *Nature*, 1986, 321:522-525.
Kabat et al., "Unusual Distributions of Amino Acids in Complementarity-determining (Hypervariable) Segments of Heavy and Light Chains of Immunoglobulins and Their Possible Roles in Specificity of Antibody-combining Sites," *J Biol Chem*, 1977, 252:6609-6616.
Karlsson et al., "Analyzing a kinetic titration series using affinity biosensors," *Analyt Biochem*, 2006, 349:136-147.
Kaufman and Sharp, "Amplification and Expression of Sequences Cotransfected with a Modular Dihydrofolate Reductase Complementary DNA Gene," *J Mol Biol*, 1982, 159:601-621.
Kerbel, "Vasohibin: the feedback on a new inhibitor of angiogenesis," *J Clin Invest*, 2004, 114(7):884-886.
Kettleborough et al., "Humanization of a mouse monoclonal antibody by CDR-grafting: the importance of framework residues on loop conformation," *Protein Engineering*, 1991, 4(7):773-783.
Kirkland et al., "Analysis of the fine specificity and cross-reactivity of monoclonal anti-lipid A antibodies," *J Immunol*, 1986, 137:3614-3619.
Kitamura et al., "Chemical engineering of the monoclonal antibody A7 by polyethylene glycol for targeting cancer chemotherapy," *Cancer Res*, 1991, 51(16):4310-4315.
Kitamura et al., "Polyethylene glycol modification of the monoclonal antibody A7 enhances its tumor localization," *Biochem Biophys Res Commun*, 1990, 171(3):1387-1394.
Knauf et al., "Relationship of effective molecular size to systemic clearance in rats of recombinant interleukin-2 chemically modified with water-soluble polymers," *J Biol Chem*, 1988, 263(29):15064-15070.
Ko et al., "Treatment of advanced tumors with agonistic anti-GITR mAb and its effects on tumor-infiltrating Foxp3$^+$CD25$^+$CD4$^+$ regulatory T cells," *J Exp Med*, 2005, 202(7):885-891.
Ko et al., "A Combination of Chemoimmunotherapies Can Efficiently Break Self-Tolerance and Induce Antitumor Immunity in a Tolerogenic Murine Tumor Model," *Cancer Res*, 2007, 67(15):7477-7486.
Köhler and Milstein, "Continuous cultures of fused cells secreting antibody of predefined specificity," *Nature*, 1975, 256:495-497.
Köhler, "Immunoglobulin chain loss in hybridoma lines," *Proc Natl Acad Sci USA*, 1980, 77:2197-2199.
Kolbinger et al., "Humanization of a mouse anti-human IgE antibody: a potential therapeutic IgE-mediated allergies," *Protein Engineering*, 1993, 6(8):971-980.
Krebber et al., "Reliable cloning of functional antibody variable domains from hybridomas and spleen cell repertoires employing a reengineered phage display system," *J Immunol Meth*, 1997, 201:35-55.

Kwon et al., "Identification of a Novel Activation-inducible Protein of the Tumor Necrosis Factor Receptor Superfamily and Its Ligand," *J Biol Chem*, 1999, 274(10):6056-6061.

Lamminmäki et al., "Expanding the conformational diversity by random insertions to CDRH2 results in improved anti-estradiol antibodies," *J Mol Biol*, 1999, 291(3):589-602.

Larrick et al., "Rapid cloning of rearranged immunoglobulin genes from human hybridoma cells using mixed primers and the polymerase chain reaction," *Biochem Biophys Res Commun*, 1989, 160(3):1250-1256.

Lee and Richards, "The Interpretation of Protein Structures: Estimation of Static Accessibility," *J Mol Biol*, 1971, 55:379-400.

Liu et al., "Towards proteome-wide production of monoclonal antibody by phage display," *J Mol Biol*, 2002, 315(5):1063-1073.

MacCallum et al., "Antibody-antigen interactions: contact analysis and binding site topography," *J Mol Biol*, 1996, 262(5):732-745.

Marks et al., "By-Passing Immunization: Building High Affinity Human Antibodies by Chain Shuffling," *Bio/Technol*, 1992, 10:779-783.

Marks et al., "By-passing Immunization. Human Antibodies from V-gene Libraries Displayed on Phage," *J Mol Biol*, 1991, 222:581-597.

Martin and Thornton, "Structural Families in Loops of Homologous Proteins: Automatic Classification, Modelling and Application to Antibodies," *J Mol Biol*, 1996, 263:800-815.

McManus and Sharp, "Gene silencing in mammals by small interfering RNAs," *Nat Rev Genet*, 2002,3(10):737-747.

Mercola and Cohen, "Antisense approaches to cancer gene therapy," *Cancer Gene Ther*, 1995, 2:47-59.

Milenic et al., "Construction, Binding Properties, Metabolism, and Tumor Targeting of a Single-Chain Fv Derived from the Pancarcinoma Monoclonal Antibody CC49," *Cancer Res*, 1991, 51:6363-6371.

Moldenhauer et al., "Identity of HML-1 Antigen on Intestinal Intraepithelial T Cells and of B-ly7 Antigen on Hairy Cell Leukaemia," *Scand J Immunol*, 1990, 32:77-82.

Morel et al., "Monoclonal Antibodies to Bovine Serum Albumin: Affinity and Specificity Determinations," *Mol Immunol*, 1988, 25:7-15.

Morrison et al., "Chimeric human antibody molecules: Mouse antigen-binding domains with human constant region domains," *Proc Natl Acad Sci USA*, 1984, 81:6851-6855.

Morrison, "Sequentially derived mutants of the constant region of the heavy chain of murine immunoglobulins," *J Immun*, 1979, 123:793-800.

Morrison, "Transfer and Expression of Immunoglobulin Genes," *Annu Rev Immunol*, 1984, 2:239-256.

Morrison, "Transfectomas Provide Novel Chimeric Antibodies," *Science*, 1985, 229:1202-1207.

Morrison and Oi, "Genetically engineered antibody molecules," *Adv Immunol*, 1989, 44:65-92.

Mosmann and Coffman, "TH1 and TH2 Cells: Different Patterns of Lymphokine Secretion Lead to Different Functional Properties," *Ann Rev Immunol*, 1989, 7:145-173.

Nagy et al., "Fully human, HLA-DR-specific monoclonal antibodies efficiently induce programmed death of malignant lymphoid cells," *Nat Med*, 2002, 8:801-805.

Newman et al., ""Primatization" of Recombinant Antibodies for Immunotherapy of Human Diseases: A Macaque/Human Chimeric Antibody Against Human CD4," *Biotechnol*, 1992, 10:1455-1460.

Novotny and Haber, "Structural invariants of antigen binding: Comparison of immunoglobulin $V_L$-$V_H$ and $V_L$-$V_L$ domain dimers," *Proc Natl Acad Sci USA*, 1985, 82:4592-4596.

Orlandi et al., "Cloning immunoglobulin variable domains for expression by the polymerase chain reaction," *Proc Natl Acad Sci USA*, 1989, 86:3833-3837.

Padlan, "A possible procedure for reducing the immunogenicity of antibody variable domains while preserving their ligand-binding properties," *Mol Immunol*, 1991, 28:489-498.

Padlan, "Anatomy of the antibody molecule," *Mol Immunol*, 1994, 31:169-217.

Paliard et al., "Simultaneous production of IL-2, IL-4, and IFN-gamma by activated human $CD4^+$ and $CD8^+$ T cell clones," *J Immunol*, 1988, 141:849-855.

Pantoliano et al., "Conformational Stability, Folding, and Ligand-Binding Affinity of Single-Chain Fv Immunoglobulin Fragments Expressed in *Escherichia coli*," *Biochem*, 1991, 30:10117-10125.

De Pascalis et al., "Grafting of "abbreviated" complementarity-determining regions containing specificity-determining residues essential for ligand contact to engineer a less immunogenic humanized monoclonal antibody," *J. Immunol.*, 2002, 169:3076-3084.

Paul and Seder, "Lymphocyte Responses and Cytokines," *Cell*, 1994, 76:241-251.

Paul, *Fundamental Immunology*, $3^{rd}$ Edition, 1993, pp. 292-295.

Pedley et al., "The potential for enhanced tumour localization by poly(ethylene glycol) modification of anti-CEA antibody," *Br J Cancer*, 1994, 70:1126-1130.

Presta, "Antibody engineering," *Curr Opin Struct Biol*, 1992, 3(4):394-398.

Queen et al., "A humanized antibody that binds to the interleukin 2 receptor," *Proc Natl Acad Sci USA*, 1989, 86:10029-10033.

Queen et al., "Cell-Type Specific Regulation of a κ Immunoglobulin Gene by Promoter and Enhancer Elements," *Immunol Rev*, 1986, 89:49-68.

Raso and Griffin, "Hybrid Antibodies with Dual Specificity for the Delivery of Ricin to Immunoglobulin-bearing Target Cells," *Cancer Res*, 1981, 41:2073-2078.

Riechmann et al., "Reshaping human antibodies for therapy," *Nature*, 1988, 332:323-327.

Rossi, "Therapeutic antisense and ribozymes," *Br Med Bull*, 1995, 51:217-225.

Ruberti et al., "The use of the RACE method to clone hybridoma cDNA when V region primers fail," *J Immunol Meth*, 1994, 173:33-39.

Rudikoff et al., "Single amino acid substitution altering antigen-binding specificity," *Proc. Natl. Acad. Sci. USA*, 1982, 79:1979-1983.

Sblattero and Bradbury, "A definitive set of oligonucleotide primers for amplifying human V regions," *Immunotechnol*, 1998, 3:271-278.

Sharp and Zamore, "Molecular biology. RNA interference," *Science*, 2000, 287:2431-2432.

Shields et al., "High resolution mapping of the binding site on human IgG1 for Fc gamma RI, Fc gamma RII, Fc gamma RIII, and FcRn and design of IgG1 variants with improved binding to the Fc gamma R," *J Biol Chem*, 2001, 276:6591-6604.

Stahli et al., "Distinction of Epitopes by Monoclonal Antibodies," *Meth Enzymol*, 1983, 92:242-253.

Strejan et al., "Suppression of chronic-relapsing experimental allergic encephalomyelitis in strain-13 guinea pigs by administration of liposome-associated myelin basic protein," *J Neuroimmunol*, 1984, 7:27.

Takkinen et al., "An active single-chain antibody containing a cellulose linker domain is secreted by *Escherichia coli*," *Protein Eng*, 1991, 4:837-841.

Tallarida, *Drug Synergism and Dose-effect Analysis*, 2000, Chapman & Hall/CRC, Boca Raton, pp. 1-13.

Taylor et al., "A transgenic mouse that expresses a diversity of human sequence heavy and light chain immunoglobulins," *Nucl Acids Res.*, 1992, 20:6287-6295.

Tempest et al., "Reshaping a human monoclonal antibody to inhibit human respiratory syncytial virus infection in vivo," *Biotechnol*, 1991, 9:266-271.

Thompson et al., "Affinity maturation of a high-affinity human monoclonal antibody against the third hypervariable loop of human immunodeficiency virus: use of phage display to improve affinity and broaden strain reactivity," *J Mol Biol*, 1996, 256:77-88.

Tramontano et al., "Framework Residue 71 is a Major Determinant of the Position and Conformation of the Second Hypervariable Region in the $V_H$ Domains of Immunoglobulins," *J Mol Biol*, 1990, 215:175-182.

Tuschl et al., "Targeted mRNA degradation by double-stranded RNA in vitro," *Genes Dev*, 1999, 13:3191-3197.

Urlaub and Chasin, "Isolation of Chinese hamster cell mutants deficient in dihydrofolate reductase activity," *Proc Natl Acad Sci USA*, 1980, 77:4216-4220.

Verhoeyen et al., "Reshaping Human Antibodies: Grafting an Antilysozyme Activity," *Science*, 1988, 239:1534-1536.

Wagner, "Gene inhibition using antisense oligodeoxynucleolides," *Nature*, 1994, 372:333-335.

Waldmann and Cobbold, "Regulating the Immune Response to Transplants: A Role for CD4[+] Regulatory Cells?" *Immunity*, 2001, 14:399-408.

Wiesenthal (http://weisenthal.org/feedback.html, Feb. 4, 2002).

Wilson et al., "The use of mRNA display to select high-affinity protein-binding peptides," *Proc Natl Acad Sci USA*, 2001, 98(7):3750-3755.

Winter and Milstein, "Man-made antibodies," *Nature*, 1991, 349:293-299.

Winter et al., "Making antibodies by phage display technology," *Annu Rev Immunol*, 1994, 12:433-455.

Yang et al., "Identification of the Ebola virus glycoprotein as the main viral determinant of vascular cell cytotoxicity and injury," *Nat Med*, 2000, 6:886-889.

Zamore et al., "RNAi: double-stranded RNA directs the ATP-dependent cleavage of mRNA at 21 to 23 nucleotide intervals," *Cell*, 2000, 101:25-33.

Zapata et al., *FASEB J*, 1995, 9:A1479.

Authorized officer Dorothée Mülhausen, International Preliminary Report on Patentability in PCT/US2008/008502, dated Jan. 21, 2010, 9 pages.

Mouse α Human GITR (6C8)

6C8 VHD

A.

**ATGGACAGACTTACATTCTCATTCCTGCTGCTGATTGTCCCTGCA
TATGTCTTGTCCCA**GTTACTCTAAAAGAGTCTGGCCCTGGGATATT
GAAGCCCTCACAGACCCTCAGTCTGACTTGTTCTTTCTCT*GGGTTT
TCACTGAGCACTTCTGGTATGGGTGTAGGC*TGGATTCGTCAGCCT
TCAGGGAAGGGTCTGGAGTGGCTGGCG*CACATTTGGTGGGATGA
TGATAAGTACTATAATCCATCCCTGAAGAGC*CAGCTCACAATCTCC
AAGGATACCTCCAGAAACCAGGTATTCCTCAAGATCACCAGTGTG
GACACTGCAGATGCTGCCACTTACTACTGTGCTCGA*ACTAGGAGG
TACTTCCCCTTTGCTTAC*TGGGGCCAAGGGACACTAGTCACAGTC
TCCTCA

B.

MDRLTFSFLLLIVPAYVLSQVTLKESGPGILKPSQTLSLTCSFS*GFSLS
TSGMGVGW*IRQPSGKGLEWLA*HIWWDDDKYYNPSLKS*QLTISKDTS
RNQVFLKITSVDTADAATYYCAR*TRRYFPFA*YWGQGTLVTVSS

6C8 VKA

C.

**ATGGAGACACAGTCTCAGGTCTTTGTATACATGTTGCTGTGGTTG
TCTGGTGTTGATGGA**GACATTGTGATGACCCAGTCTCAAAAATTCA
TGTCCACATCAGTAGGAGACAGGGTCAGCGTCACCTGC*AAGGCC
AGTCAGAATGTGGGTACTAATGTAGCC*TGGTATCAACAGAAACCA
GGGCAATCTCCTAAAGCACTGATTTAC*TCGGCATCCTACCGGTAC
AGT*GGAGTCCCTGATCGCTTCACAGGCAGTGGATCTGGGACAGAT
TTCACTCTCACCATCAACAATGTGCACTCTGAAGACTTGGCAGAGT
ATTTCTGT*CAACAATATAACACCGATCCGCTCACG*TTCGGAGCTGG
GACCAAGCTGGAAATCAAA

D.

METQSQVFVYMLLWLSGVDGDIVMTQSQKFMSTSVGDRVSVTC*KA
SQNVGTNVA*WYQQKPGQSPKALIY*SASYRYSGVPDRFTGSGSGTDF
TLTINNVHSEDLAEYFCQQ*YNTDPL*TFGAGTKLEIK

*Fig. 18*

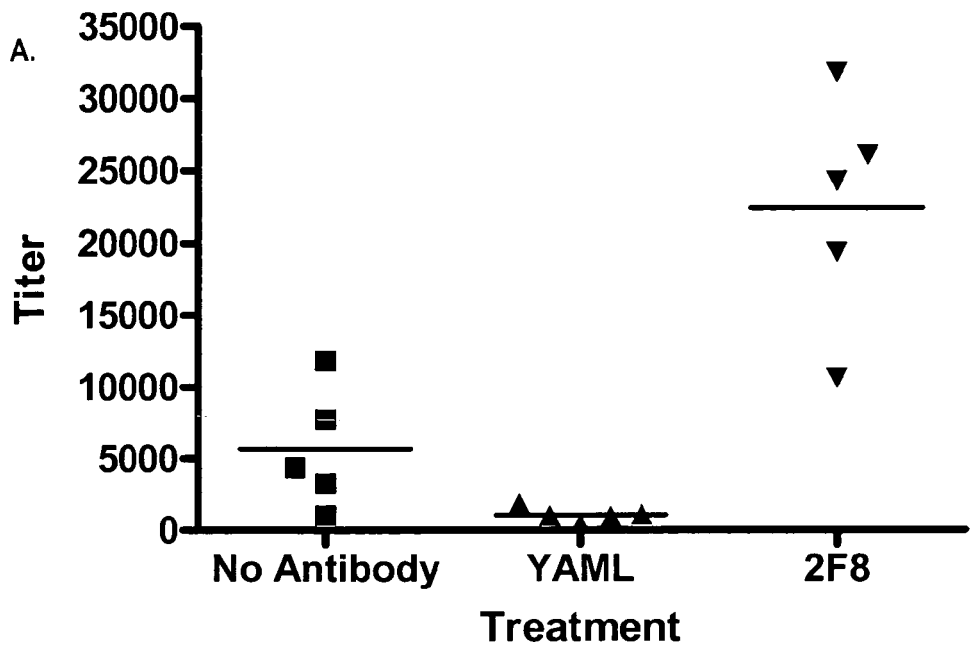
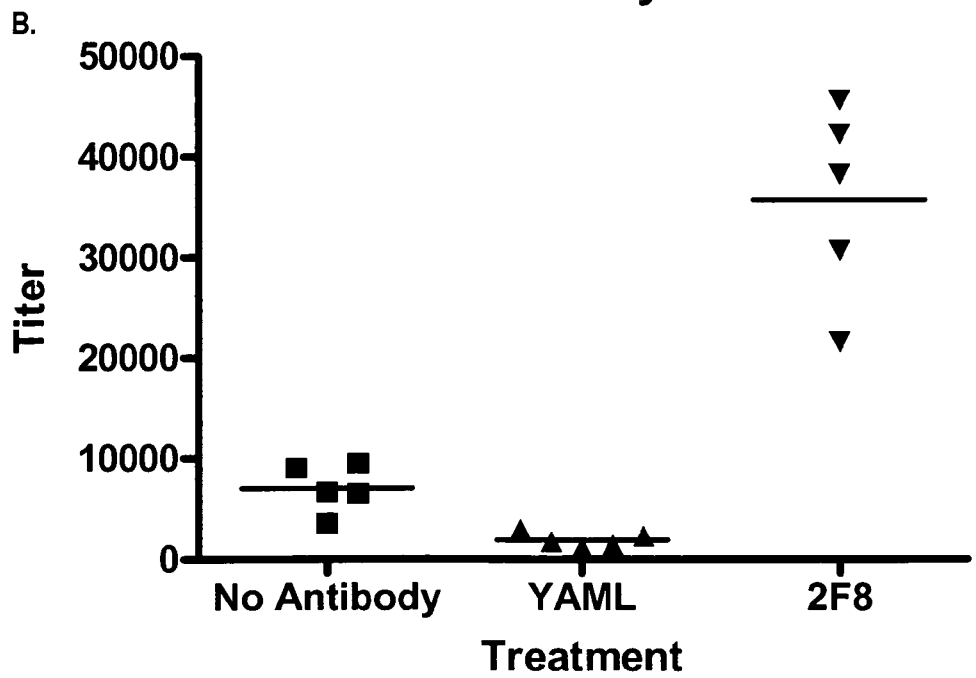
Fig. 19

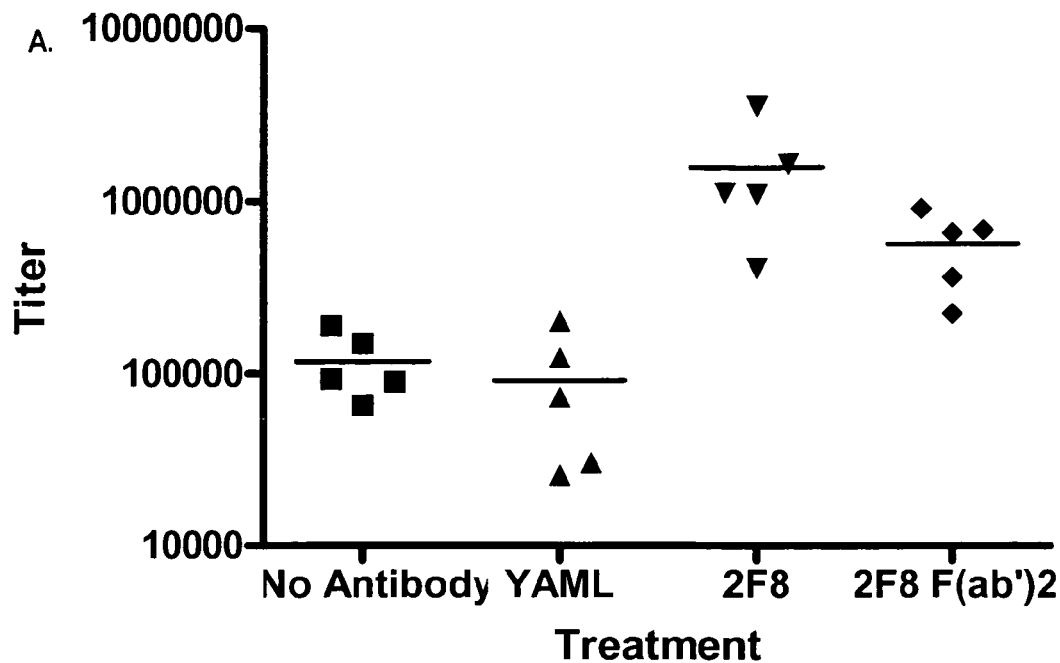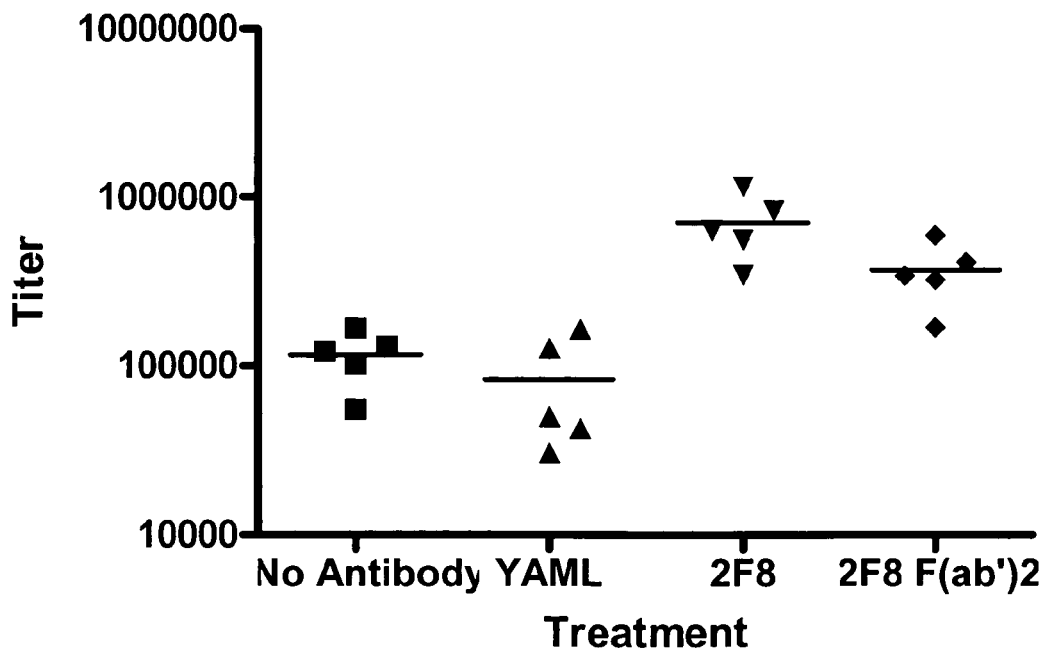
Fig. 20

GITR-BINDING ANTIBODIES

RELATED APPLICATIONS

This application claims the benefit of priority to U.S. Provisional Application 60/665,322, filed on Mar. 25, 2005, titled "GITR BINDING MOLECULES AND USES THEREFOR" and U.S. Provisional Application 60/687,265, filed on Jun. 3, 2005, titled "GITR BINDING MOLECULES AND USES THEREFOR", the entire contents of each are hereby incorporated by reference.

BACKGROUND OF THE INVENTION

Members of the tumor necrosis factor and TNF receptor (TNFR) superfamily regulate diverse biologic functions, including cell proliferation, differentiation, and survival. Using differential display to identify T cell mRNAs induced by the synthetic glucocorticoid hormone dexamethasone, Nocentini et al. ((1997) *Proc. Natl. Acad. Sci., USA* 94:6216-6221997) identified a mouse cDNA encoding a novel member of the TNFR family. The corresponding gene was designated GITR for glucocorticoid-induced TNFR family-related gene (also known as TNFRSF18). Like other TNFRs, the predicted GITR protein contains cysteine-rich repeats in the extracellular domain. In addition, the intracellular domain of GITR shares significant homology with those of the mouse and human TNFRs, 4-1BB and CD27. Nocentini et al. ((1997) *Proc. Natl. Acad. Sci., USA* 94:6216-6221997) demonstrated that the GITR gene is induced in T cells by dexamethasone as well as by other cell-activating stimuli. GITR expression protects T cells from apoptosis induced by treatment with anti-CD3 antibodies, but not by other apoptotic agents.

Shimizu et al. ((2002) *Nat Immunol* 3:135-42) found that GITR was predominantly expressed on CD4+CD25+ regulatory T cells. However, GITR is also expressed on conventional CD4+ and CD8+ T cells, and its expression is enhanced rapidly after activation. In vitro studies have showed that GITR plays a key role in the peripheral tolerance that is mediated by these cells and abrogates the suppressive function of CD4+CD25+ regulatory T cells (Shimizu et al. (2002) *Nat Immunol* 3:135-42; McHugh et al. (2002) *Immunity* 16:311-23).

The development of agents useful in modulating signaling via GITR would be of great benefit.

SUMMARY OF THE INVENTION

The present invention provides binding molecules that specifically bind to GITR, e.g., human GITR (hGITR), on cells, such as T cells and dendritic cells. The binding molecules of the invention are characterized by binding to hGITR with high affinity, are agonistic in the presence of a stimulating agent, e.g., CD3, and abrogate the suppression of T effector (Teff) cells by T regulatory (Treg) cells.

One aspect of the invention features a binding molecule comprising the amino acid sequence of SEQ ID NO.: 1, optionally comprising a leader sequence.

In another aspect, the invention features a binding molecule comprising the amino acid sequence of SEQ ID NO.: 66, optionally comprising a leader sequence.

In another aspect, the invention features a binding molecule comprising the amino acid sequence of SEQ ID NO.:2, optionally comprising a leader sequence.

Another aspect of the invention features a binding molecule comprising the amino acid sequence of SEQ ID NO:58, optionally comprising a leader sequence.

One aspect of the invention features a binding molecule comprising the amino acid sequence of SEQ ID NO.:59, optionally comprising a leader sequence.

In another aspect, the invention features a binding molecule comprising the amino acid sequence of SEQ ID NO.: 60, optionally comprising a leader sequence.

In one aspect, the invention features a binding molecule comprising the amino acid sequence of SEQ ID NO.:61, optionally comprising a leader sequence.

In another aspect, the invention features a binding molecule comprising the amino acid sequence of SEQ ID NO.: 62, optionally comprising a leader sequence.

One aspect of the invention features a binding molecule comprising the amino acid sequence of SEQ ID NO.:63, optionally comprising a leader sequence.

Yet another aspect of the invention features a binding molecule comprising at least one complementarity determining region (CDR) amino acid sequence selected from the group consisting of: SEQ ID NO.:3, SEQ ID NO.:4, or SEQ ID NO:19, and SEQ ID NO.:5. In one embodiment, the binding molecule comprises at least two complementarity determining region (CDR) amino acid sequence selected from the group consisting of: SEQ ID NO.:3, SEQ ID NO.:4, or SEQ ID NO:19, and SEQ ID NO.:5. In another embodiment, the binding molecule comprises at least three complementarity determining region (CDR) amino acid sequence selected from the group consisting of: SEQ ID NO.:3, SEQ ID NO.:4, or SEQ ID NO:19, and SEQ ID NO.:5.

Another aspect of the invention features a binding molecule comprising at least one complementarity determining region (CDR) amino acid sequence selected from the group consisting of: SEQ ID NO.:6, SEQ ID NO.:7, and SEQ ID NO.:8. In one embodiment, the binding molecule comprises at least two complementarity determining region (CDR) amino acid sequence selected from the group consisting of: SEQ ID NO.:6, SEQ ID NO.:7, and SEQ ID NO.:8. In another embodiment, the binding molecule comprises at least three complementarity determining region (CDR) amino acid sequence selected from the group consisting of: SEQ ID NO.:6, SEQ ID NO.:7, and SEQ ID NO.:8.

Another aspect of the invention features a binding molecule comprising the CDRs shown in SEQ ID NOs.: 3, 4, 5, 6, 7, and 8. In another aspect of the invention features a binding molecule comprising the CDRs shown in SEQ ID NOs.:3, 19,5,6,7, and 8.

One aspect of the invention features a binding molecule comprising a heavy chain variable region comprising the amino acid sequence of SEQ ID NO.:1 and further comprising a light chain variable region comprising the amino acid sequence of SEQ ID NO.:2. Another aspect of the invention features a binding molecule comprising a heavy chain variable region comprising the amino acid sequence of SEQ ID NO.:66 and further comprising a light chain variable region comprising the amino acid sequence of SEQ ID NO.:2. In more than one embodiment, the binding molecule comprises human or substantially human heavy and light chain framework regions. In another embodiment, one or more human framework amino acid residues are mutated to the corresponding murine amino acid residue. In another embodiment, the constant region comprises an IgG2b heavy chain constant region. In another embodiment, the constant region comprises a human, e.g., human IgG1, heavy chain constant region. In another embodiment, the binding molecule is altered to reduce effector function and/or glycosylation. In one embodiment, the binding molecule binds to human GITR In one embodiment, the binding molecule does not induce apoptosis. In another embodiment, the binding molecule does not block the primary mixed lymphocyte reaction. In yet another embodiment, the binding molecule abrogates the suppression of T effector cells by T regulatory cells. In one embodiment, the binding molecule modulates effector T cell proliferation. In one embodiment, the binding molecule is murine. In another embodiment, the binding molecule comprises a murine IgG2b heavy chain. In one embodiment, the binding molecule is a humanized antibody. In a further embodiment, the binding molecule is a chimeric antibody. In yet another embodiment, the binding molecule modulates the activity of human GITR. In another embodiment, the binding molecule attenuates degradation of I-κB in T cells.

Another aspect of the invention features a binding molecule that binds to GITR on human T cells and human dendritic cells and has a binding constant (Kd) of $1 \times 10^{-9}$ or less. In one embodiment, the binding molecule abrogates the suppression of T effector cells by T regulatory cells. In another embodiment, the binding molecule is a humanized antibody.

Yet another aspect of the invention features a composition comprising a binding molecule of the invention and a pharmaceutically acceptable carrier. In one embodiment, the composition further comprises at least one additional therapeutic agent for treating cancer in a subject. In one embodiment, the composition further comprises at least one additional therapeutic agent for treating a viral infection in a subject. In another embodiment, the composition further comprises at least one tumor antigen for treating cancer in a subject. In yet another embodiment, the composition further comprises at least one antigen from a pathogenic agent.

One aspect of the invention features a method for abrogating the suppression of T effector cells by T regulatory cells, comprising contacting human immune cells with a binding molecule of the invention such that the suppression of T effector cells by T regulatory cells is abrogated.

Another aspect of the invention features a method for modulating T cell receptor induced signaling in an effector T cell, comprising contacting a cell with a binding molecule of the invention, such that T cell induced receptor signaling in an effector T cell is modulated. In one embodiment, the method modulates the degradation of I-κB. In one embodiment, the T cell is a Th1 cell. In another embodiment, the T cell is a CD4+ cell. In yet another embodiment, the T cell is a CD8+ cell.

Yet another aspect of the invention features a method for enhancing an immune response in a subject, comprising contacting a cell with a binding molecule of the invention such that that an immune response in a subject is enhanced.

Another aspect of the invention features a method for treating cancer in a subject, comprising contacting a cell with a binding molecule of the invention such that cancer is treated in a subject. In one embodiment, the type of cancer is selected from the group consisting of: pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

Another aspect of the invention features a method for treating an infection caused by a pathogenic agent in a subject, comprising contacting a cell with the binding molecule of claim 1, such that the infection caused by a pathogenic agent is treated in a subject. In one embodiment, the pathogenic agent is a virus, e.g., selected from the group consisting of: hepatitis type A, hepatitis type B, hepatitis type C, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV I), and human immunodeficiency virus type II (HIV II), any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein Barr virus, human herpesvirus 6, cercopithecine herpes virus 1 (B virus), and poxviruses. In one embodiment, the method is used to treat a chronic viral infection.

In another embodiment, the pathogenic agent is a bacterium, e.g., selected from the group consisting of: *Neisseria* spp, *Streptococcus* spp, *S. mutans, Haemophilus* spp., *Moraxella* spp, *Bordetella* spp, *Mycobacterium* spp, *Legionella* spp, *Escherichia* spp, *Vibrio* spp, *Yersinia* spp, *Campylobacter* spp, *Salmonella* spp, *Listeria* spp.; *Helicobacter* spp, *Pseudomonas* spp, *Staphylococcus* spp., *Enterococcus* spp, *Clostridium* spp., *Bacillus* spp, *Corynebacterium* spp., *Borrelia* spp., *Ehrlichia* spp, *Rickettsia* spp, *Chlamydia* spp., *Leptospira* spp., *Treponema* spp.

Another aspect of the invention features a method for modulating GITR function comprising contacting human GITR with a binding molecule of the invention in the presence of an immunostimulatory agent such that GITR function is modulated.

One aspect of the invention features a binding molecule comprising at least one CDR amino acid sequence selected from the group consisting of: SEQ ID NO.:3, SEQ ID NO.:4, SEQ ID NO:19, SEQ ID NO.:5, SEQ ID NO.:6, SEQ ID NO.:7, and SEQ ID NO.:8. In one embodiment, the composition further comprises at least one additional therapeutic agent for treating cancer in a subject. In another embodiment, the binding molecule comprises at least one CDR derived from the 6C8 binding molecule. In another embodiment, the binding molecule comprises at least two CDRs derived from the 6C8 binding molecule. In another embodiment, the binding molecule comprises at least three CDRs derived from the 6C8 binding molecule. In another embodiment, the binding molecule comprises at least four CDRs derived from the 6C8 binding molecule. In another embodiment, the binding molecule comprises at least five CDRs derived from the 6C8 binding molecule. In another embodiment, the binding molecule comprises at least six CDRs derived from the 6C8 binding molecule.

Another aspect of the invention features a binding molecule comprising the six CDRs shown in SEQ ID NOs.: 3, 4 or 19, 5, 6, 7, and 8.

Yet another aspect of the invention features a binding molecule comprising a heavy chain variable region comprising the amino acid sequence of SEQ ID NO.:1 and further comprising a light chain variable region comprising the amino acid sequence of SEQ ID NO.:2. In one embodiment, a binding molecule comprises human or substantially human heavy and light chain framework regions. In another embodiment a binding molecule of the invention comprises human framework regions in which one or more human framework amino acid residues are backmutated to the corresponding murine amino acid residue or are mutated to another amino acid residue. In another embodiment, a binding molecule of the invention comprises a constant region of an immunoglobulin molecule, e.g., an IgG2b heavy chain constant region. In yet another embodiment, the binding molecule binds to human GITR (hGITR). In one embodiment, the binding molecule does not induce apoptosis. In another embodiment, the binding molecule does not block the primary mixed lymphocyte reaction. In yet another embodiment, the binding molecule abrogates the suppression of T effector cells by T regulatory cells. In one embodiment, the binding molecule enhances effector T cell proliferation. In another embodiment, the binding molecule neutralizes the activity of human GITR. In yet another embodiment, the binding molecule attenuates degradation of I-κB in T cells.

In one aspect, the invention features a binding molecule that binds to GITR on human T cells and human dendritic cells and has a binding constant (Kd) of $1 \times 10^{-9}$ or less. In one embodiment, the binding molecule abrogates the suppression of T regulatory cells. In another embodiment, the binding molecule is murine or comprises murine CDRs. In a further embodiment, the binding molecule comprises an IgG2b heavy chain. In one embodiment, the binding molecule is a humanized antibody. In a further embodiment, the binding molecule is a chimeric antibody.

Another aspect of the invention features, a composition comprising a binding molecule of the invention and a pharmaceutically acceptable carrier. In one embodiment, the composition further comprises at least one additional therapeutic agent for treating cancer in a subject.

One aspect of the invention features a method for abrogating the suppression of T effector cells by T regulatory cells, comprising contacting human immune cells with a binding molecule of the invention such that the suppression of T regulatory cells is abrogated.

Another aspect of the invention features a method for modulating T cell receptor induced signaling in an effector T cell, comprising contacting a cell with a binding molecule of the invention, such that T cell induced receptor signaling in an effector T cell is modulated. In one embodiment, the method modulates the degradation of I-κB. In one embodiment, the T cell is a Th1 cell.

Yet another aspect of the invention features a method for enhancing an immune response in a subject, comprising contacting a cell with a binding molecule of the invention such that that an immune response in a subject is enhanced.

Another aspect of the invention features a method for treating cancer in a subject, comprising contacting a cell with a binding molecule of the invention such that cancer is treated in a subject. In one embodiment, the type of cancer is selected from the group consisting of: pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

Another aspect of the invention features a method for inhibiting GITR function comprising contacting human GITR with a binding molecule of the invention in the presence of a stimulating agent such that GITR function is inhibited.

One aspect of the invention features an isolated nucleic acid molecule comprising a nucleotide sequence encoding a heavy chain variable region comprising the nucleotide sequence of SEQ ID NO.:9, optionally comprising a leader sequence. Another aspect of the invention features an isolated nucleic acid molecule comprising a nucleotide sequence encoding a heavy chain variable region comprising the nucleotide sequence of SEQ ID NO.:67, optionally comprising a leader sequence.

Another aspect of the invention features an isolated nucleic acid molecule comprising a nucleotide sequence encoding a light chain variable region comprising the nucleotide sequence of SEQ ID NO.:10, optionally comprising a leader sequence.

Yet another aspect of the invention features an isolated nucleic acid molecule comprising a nucleotide sequence encoding at least one CDR selected from the group consisting of: SEQ ID NO.:11, SEQ ID NO.:12 or SEQ ID NO:65, and SEQ ID NO.:13. In one embodiment, the isolated nucleic acid molecule comprises a nucleotide sequence encoding at least two CDRs derived from the 6C8 binding molecule. In another embodiment, the isolated nucleic acid molecule comprises a nucleotide sequence encoding at least three CDRs derived from the 6C8 binding molecule.

Another aspect of the invention features an isolated nucleic acid molecule comprising a nucleotide sequence encoding at least one CDR selected from the group consisting of: SEQ ID NO.:14 SEQ ID NO.:15 and SEQ ID NO.: 16. In one embodiment, the isolated nucleic acid molecule comprises a nucleotide sequence encoding at least at least two CDRs derived from the 6C8 binding molecule. In another embodiment, the isolated nucleic acid molecule comprises a nucleotide sequence encoding at least three CDRs derived from the 6C8 binding molecule.

One aspect of the invention features an isolated nucleic acid molecule comprising the nucleotide sequences shown in SEQ ID NOs.: 11-16 and SEQ ID NO:65.

One aspect of the invention features a recombinant expression vector comprising the nucleic acid molecules of the invention. In one embodiment, a recombinant expression vector comprising a nucleic acid molecule having a nucleotide sequence encoding the binding molecule of the invention is featured. In another embodiment, the invention features a host cell into which the recombinant expression vector of the invention has been introduced. In another aspect the invention features a method for producing a binding molecule that binds human GITR, comprising culturing the host cell of the invention in a culture medium until a binding molecule that binds human GITR is produced by the cell.

BRIEF DESCRIPTION OF THE DRAWINGS

FIGS. 18A-18D depict the nucleic acid and amino acid sequences of the variable heavy chain (VHD) (A and B, respectively; SEQ ID NOs: 1 and 9, respectively) and variable light:Chain (VKA) (C and D, respectively; SEQ ID NOs: 2 and 10, respectively) of the 6C8 binding. molecule. The leader sequences are shown in bold; the framework sequences are underlined; the CDR sequences are italicized.

FIGS. 19A and 19B are graphs showing that 2F8 and 2F8 F(ab')2 fragments enhance the humoral response to HA.

FIGS. 20A and 20B are graphs showing that 2F8 and 2F8 F(ab')2 fragments enhance the humoral response to Ova.

DETAILED DESCRIPTION OF THE INVENTION

Figure 1:
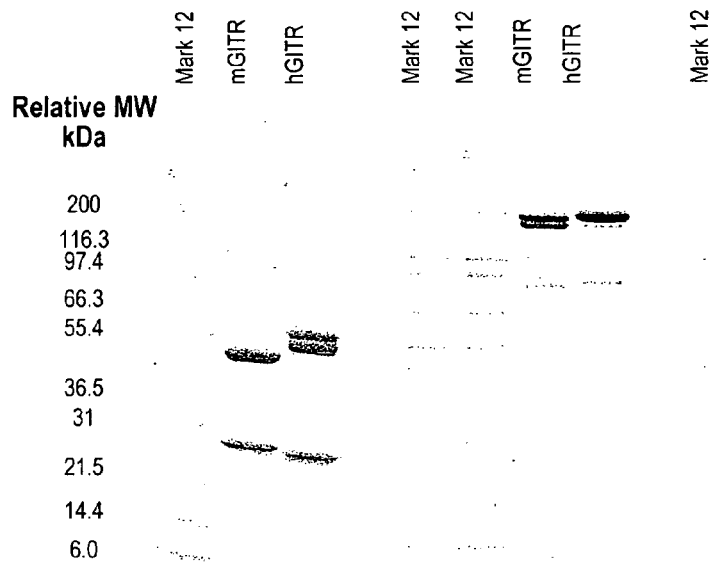
FIG. 1 depicts an SDS-PAGE blot of purified mouse and human GITR binding molecules. Twelve micrograms of protein was loaded per well.

The present invention provides binding molecules that specifically bind to GITR, e.g., human GITR (hGITR), on T cells and dendritic cells. The binding molecules of the invention are characterized by binding to hGITR with high affinity, and in the presence of a stimulating agent, e.g., CD3, they are agonistic, and they abrogate the suppression of T effector (Teff) cells by T regulatory (Treg) cells. Various aspects of the invention relate to binding molecules, and pharmaceutical compositions thereof, as well as nucleic acids encoding binding molecules, recombinant expression vectors and host cells for making such binding molecules. Methods of using a binding molecule of the invention to detect human GITR or to modulate human GITR activity, either in vitro or in vivo, are also encompassed by the invention.

In order that the present invention may be more readily understood, certain terms are first defined.

I. Definitions

The term "glucocorticoid-induced TNFR family-related receptor" (abbreviated herein as "GITR"), also known as TNF receptor superfamily 18 (TNFRSF18), as used herein, refers to a member of the tumor necrosis factor/nerve growth factor receptor family. It is a 241 amino acid type I transmembrane protein characterized by three cysteine pseudorepeats in the extracellular domain and specifically protects T-cell receptor-induced apoptosis, although it does not protect cells from other apoptotic signals, including Fas triggering, dexamethasone treatment, or UV irradiation (Nocentini, G, et al. (1997) Proc. Natl. Acad. Sci., USA 94:6216-622). The nucleic acid sequence of human GITR (hGITR) is set forth in SEQ ID NO.: 17 and the amino acid sequence is set forth in SEQ ID NO.: 18.

The term "binding molecule" as used herein includes molecules that contain at least one antigen binding site that specifically binds to GITR. By "specifically binds" it is meant that the binding molecules exhibit essentially background binding to non-GITR molecules. An isolated binding molecule that specifically binds GITR may, however, have cross-reactivity to GITR molecules from other species.

The binding molecules of the invention may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. Binding molecules may have both a heavy and a light chain. As used herein, the term binding molecule also includes, antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired activity, e.g., binding to GITR.

An "antigen" is an entity (e.g., a proteinaceous entity or peptide) to which a binding molecule specifically binds.

The term "epitope" or "antigenic determinant" refers to a site on an antigen to which a binding molecule specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, X-ray crystallography and 2-dimensional nuclear magnetic resonance. See, e.g., *Epitope Mapping Protocols in Methods in Molecular Biology*, Vol. 66, G. E. Morris, Ed. (1996).

Binding molecules that recognize the same epitope can be identified in a simple immunoassay showing the ability of one antibody to block the binding of another antibody to a target antigen, i.e., a competitive binding assay. Competitive binding is determined in an assay in which the binding molecule being tested inhibits specific binding of a reference binding molecule to a common antigen, such as GITR. Numerous types of competitive binding assays are known, for example: solid phase direct or indirect radioimmunoassay (RIA); solid phase direct or indirect enzyme immunoassay (EIA) sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test binding molecule and a labeled reference binding molecule. Competitive inhibition is measured by determining the amount of label bound to the solid surface or cells in the presence of the test binding molecule. Usually the test binding molecule is present in excess. Usually, when a competing binding molecule is present in excess, it will inhibit specific binding of a reference binding molecule to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

The term "monoclonal binding molecule" as used herein refers to a binding molecule obtained from a population of substantially homogeneous binding molecules. Monoclonal binding molecules are highly specific, being directed against a single antigenic site. Furthermore, in contrast to polyclonal binding molecule preparations which typically include different binding molecules directed against different determinants (epitopes), each monoclonal binding molecule is directed against a single determinant on the antigen. The modifier "monoclonal" indicates the character of the binding molecule as being obtained from a substantially homogeneous population of binding molecules, and is not to be construed as requiring production of the binding molecule by any particular method. For example, the monoclonal binding molecules to be used in accordance with the present invention may be made by the hybridoma method first described by Kohler, et al., *Nature* 256:495 (1975), or may be made by recombinant DNA methods (see, e.g., U.S. Pat. No. 4,816,567). The "monoclonal binding molecules" may also be isolated from phage antibody libraries using the techniques described in Clackson, et al., *Nature* 352:624-628 (1991) and Marks et al., *J Mol. Biol.* 222:581-597 (1991), for example.

The term "chimeric binding molecule" refers to a binding molecule comprising amino acid sequences derived from different species. Chimeric binding molecules can be constructed, for example by genetic engineering, from binding molecule gene segments belonging to different species.

The monoclonal binding molecules herein specifically include "chimeric" binding molecules in which a portion of the heavy and/or light chain is identical with or homologous to corresponding sequences in binding molecules derived from a particular species or belonging to a particular antibody class or subclass, while the remainder of the chain(s) is identical with or homologous to corresponding sequences in binding molecules derived from another species or belonging to another antibody class or subclass, as well as fragments of such binding molecules, so long as they exhibit the desired biological activity (U.S. Pat. No. 4,816,567; and Morrison, et al., *Proc. Natl. Acad. Sci. USA* 81:6851-6855 (1984)). e.g., binding to human GITR (hGITR).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

A "variable region" when used in reference to a binding molecule refers to the amino terminal portion of a binding molecule which confers antigen binding onto the molecule and which is not the constant region. The term includes functional fragments thereof which maintain some or all of the binding function of the whole variable region.

The term "hypervariable region" when used herein refers to the regions of a binding molecule variable domain which are hypervariable in sequence and/or form structurally defined loops. The hypervariable region comprises amino acid residues from a "complementarity determining region" or "CDR".

As used herein, the term "CDR" or "complementarity determining region" means the noncontiguous antigen combining sites found within the variable region of both heavy and light chain polypeptides. These particular regions have been described by Kabat, et al., *J. Biol. Chem.* 252, 6609-6616 (1977) and Kabat, et al., Sequences of protein of immunological interest. (1991), and by Chothia, et al., *J. Mol. Biol.* 196:901-917 (1987) and by MacCallum, et al., *J. Mol. Biol.* 262:732-745 (1996) where the definitions include overlapping or subsets of amino acid residues when compared against each other. Nevertheless, application of either definition to refer to a CDR of a binding molecule or grafted binding molecule or variants thereof is within the scope of the term as defined and used herein.

As used herein, the term "framework region" or "FR" means each domain of the framework that is separated by the CDRs. Therefore, a variable region framework is between about 100-120 amino acids in length but refers only those amino acids outside of the CDRs.

"Humanized" forms of non-human (e.g., murine) binding molecules are chimeric antibodies which contain minimal sequence derived from non-human binding molecule. For the most part, humanized binding molecules are human binding molecules (acceptor/recipient binding molecule) in which residues from a hyper-variable region are replaced by residues from a hypervariable region of a non-human species (donor binding molecule) such as mouse, rat, rabbit or non-human primate having the desired specificity, affinity, and capacity. In some instances, Fv framework region (FR) residues of the human binding molecule are altered, e.g., replaced by, substituted, or backmutated to corresponding non-human residues. Furthermore, humanized binding molecules may comprise residues which are not found in the recipient binding molecule or in the donor binding molecule. These modifications are generally made to further refine binding molecule performance. In general, the humanized binding molecule will comprise substantially all of at least one, and typically two, variable domains, in which all or substantially all of the hypervariable loops correspond to those of a non-human binding molecule and all or substantially all of the FR regions are those of a human binding molecule sequence. The humanized binding molecule optionally also will comprise at least a portion of a binding molecule constant region (Fc), typically that of a human binding molecule. For further details, see Jones, et al., *Nature* 321:522-525 (1986); Riechmann, et al., *Nature* 332:323-329 (1988); and *Presta, Curr. Op. Struct. Biol.* 2:593-596 (1992).

Preferably, a humanized binding molecule of the invention comprises at least one CDR selected from the group consisting of SEQ ID NO.:3 (GFSLSTSGMGVG (HC CDR1)), SEQ ID NO.:4 (HIWWDDDKYYNPSLKS (HC CDR2N)), SEQ ID NO.:5 (TRRYFPFAY (HC CDR3)), SEQ ID NO.:6 (KASQNVGTNVA (LC CDR1)), SEQ ID NO.:7 (SASYRYS (LC CDR2)), SEQ ID NO.:8 (QQYNTDPLT (LC CDR3)), and SEQ ID NO:19 (HIWWDDDKYYQPSLKS (HC CDR2Q)).

The term "engineered" or "recombinant" binding molecule, as used herein includes binding molecules that are prepared, expressed, created or isolated by recombinant means, such as binding molecules expressed using a recombinant expression vector transfected into a host cell, binding molecules isolated from a recombinant, combinatorial binding molecule library, binding molecules isolated from an animal (e.g., a mouse) that is transgenic for human immunoglobulin genes (see e.g., Taylor, L. D., et al. (1992) *Nucl. Acids Res.* 20:6287-6295) or binding molecules prepared, expressed, created or isolated by any other means that involves splicing of human binding molecule gene sequences to other DNA sequences. In certain embodiments, however, such recombinant human binding molecules are subjected to in vitro mutagenesis (or, when an animal transgenic for human Ig sequences is used, in vivo somatic mutagenesis) and thus the amino acid sequences of the VH and VL regions of the recombinant binding molecules are sequences that, while derived from and related to human germline VH and VL sequences, may not naturally exist within the human binding molecule germline repertoire in vivo.

An "isolated binding molecule", as used herein, refers to a binding molecule that is substantially free of other binding molecules having different antigenic specificities (e.g., an isolated binding molecule that specifically binds GITR is substantially free of binding molecules that specifically bind antigens other than GITR). Moreover, an isolated binding molecule may be substantially free of other cellular material and/or chemicals. An "isolated" binding molecule is one which has been identified and separated and/or recovered from a component of its natural environment. Contaminant components of its natural environment include, e.g., materials which would interfere with diagnostic or therapeutic uses for the binding molecule, and may include enzymes, hormones, and other proteinaceous or nonproteinaceous solutes. In preferred embodiments, the binding molecule will be purified (1) to greater than 95% by weight of binding molecule as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding molecules include binding molecules in situ within recombinant cells since at least one component of the binding molecule's natural environment will not be present. Ordinarily, however, isolated binding molecules will be prepared by at least one purification step.

As used herein the term "binding constant" "(kd)", also referred to as "affinity constant", is a measure of the extent of a reversible association between two molecular species and includes both the actual binding affinity as well as the apparent binding affinity. The actual binding affinity is determined by calculating the ratio of the Kassoc in $M^{-1} S^{-1}$ to the Kdissoc in $S^{-1}$ and has the units "$M^{-1}$". Therefore, conferring or optimizing binding affinity includes altering either or both of these components to achieve the desired level of binding affinity. The apparent affinity can include, for example, the avidity of the interaction. For example, a bivalent antibody variable region can exhibit altered or optimized binding affinity due to its valency. Binding affinity can be determined by measurement of surface plasmon resonance, e.g., using a BIAcore™ system.

The term "nucleic acid molecule", as used herein, includes DNA molecules and RNA molecules. A nucleic acid molecule may be single-stranded or double-stranded, but preferably is double-stranded DNA.

The term "isolated nucleic acid molecule", as used herein in reference to nucleic acids encoding binding molecules that bind GITR, refers to a nucleic acid molecule in which the nucleotide sequences encoding the binding molecule are free of other nucleotide sequences which other sequences may naturally flank the nucleic acid in human genomic DNA. These sequences may optionally include 5' or 3'nucleotide sequences important for regulation or protein stability.

The term "vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention includes such other forms of expression vectors, such as viral vectors (e.g., replication defective retroviruses, adenoviruses and adeno-associated viruses), which serve equivalent functions.

The term "recombinant host cell" (or simply "host cell"), as used herein, refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "T cell" (i.e., T lymphocyte) includes all cells within the T cell lineage, including thymocytes, immature T cells, mature T cells and the like, from a mammal (e.g., human). Preferably, T cells are mature T cells that express either CD4 or CD8, but not both, and a T cell receptor. The various T cell populations described herein can be defined based on their cytokine profiles and their function, and are known to one of skill in the art.

As used herein, the term "dendritic cell" refers to professional antigen-presenting cells (APCs) capable of activating naïve T cells and stimulating the growth and differentiation of B cells.

As used herein, the term "naïve T cells" includes T cells that have not been exposed to cognate antigen and so are not activated or memory cells. Naïve T cells are not cycling and human naïve T cells are CD45RA+. If naïve T cells recognize antigen and receive additional signals depending upon but not limited to the amount of antigen, route of administration and timing of administration, they may proliferate and differentiate into various subsets of T cells, e.g. effector T cells.

As used herein, the term "effector T cell" or "Teff cell" includes T cells which function to eliminate antigen (e.g., by producing cytokines which modulate the activation of other cells or by cytotoxic activity). The term "effector T cell" includes T helper cells (e.g., Th1 and Th2 cells) and cytotoxic T cells. Th1 cells mediate delayed type hypersensitivity responses and macrophage activation while Th2 cells provide help to B cells and are critical in the allergic response (Mosmann and Coffman, 1989, *Annu. Rev. Immunol.* 7, 145-173; Paul and Seder, 1994, *Cell* 76, 241-251; Arthur and Mason, 1986, *J. Exp. Med.* 163, 774-786; Paliard, et al., 1988, *J. Immunol.* 141, 849-855; Finkelman, et al., 1988, *J. Immunol.* 141, 2335-2341).

As used herein, the term "T helper type 1 response" (Th1 response) refers to a response that is characterized by the production of one or more cytokines selected from IFN-γ, IL-2, TNF, and lymphotoxin (LT) and other cytokines produced preferentially or exclusively by Th1 cells rather than by Th2 cells. As used herein, a "T helper type 2 response" (Th2 response) refers to a response by CD4+ T cells that is characterized by the production of one or more cytokines selected from IL-4, IL-5, IL-6 and IL-10, and that is associated with efficient B cell "help" provided by the Th2 cells (e.g., enhanced IgG1 and/or IgE production).

As used herein, the term "regulatory T cell" or "Treg cell" includes T cells which produce low levels of IL-2, IL-4, IL-5, and IL-12. Regulatory T cells produce TNFα, TGFβ, IFN-γ, and IL-10, albeit at lower levels than effector T cells. Although TGFβ is the predominant cytokine produced by regulatory T cells, the cytokine is produced at levels less than or equal to that produced by Th1 or Th2 cells, e.g., an order of magnitude less than in Th1 or Th2 cells. Regulatory T cells can be found in the CD4+ CD25+population of cells (see, e.g., Waldmann and Cobbold. 2001. *Immunity.* 14:399). Regulatory T cells actively suppress the proliferation and cytokine production of Th1, Th2, or naïve T cells which have been stimulated in culture with an activating signal (e.g., antigen and antigen presenting cells or with a signal that mimics antigen in the context of MHC, e.g., anti-CD3 antibody, plus anti-CD28 antibody).

As used herein, the term "tolerance" includes refractivity to activating receptor-mediated stimulation. Such refractivity is generally antigen-specific and persists after exposure to the tolerizing antigen has ceased. For example, tolerance is characterized by lack of cytokine production, e.g., IL-2, or can be assessed by use of a mixed lymphocyte culture assay. Tolerance can occur to self antigens or to foreign antigens.

A "mixed lymphocyte culture" ("MLC") is a type of lymphocyte proliferation test in which lymphocytes from two individuals are cultured together and the proliferative response ("mixed lymphocyte reaction") is measured by $^3$H-labeled thymidine uptake.

As used herein, the term "apoptosis" also referred to as programmed cell death (PCD), is the death of a cell characterized by features including, but not limited to, condensation of nuclear heterochromatin, cell shrinkage, cytoplasmic condensation, and in a later stage of apoptosis, endonuclease mediated cleavage of the DNA of the cell into discrete fragments. Upon electrophoretic analysis of the DNA of a cell in which apoptosis has occurred, a characteristic "ladder" of discrete DNA fragments may be apparent.

"Treatment" refers to both therapeutic treatment and prophylactic or preventative measures. Those in need of treatment may include those already having a disorder as well as those which do not yet have a disorder.

A "disorder" is any condition that would benefit from treatment with a binding molecule of the present invention. This includes chronic and acute disorders or diseases or pathological conditions associated with immune responses that are too high or too low.

Various aspects of the invention are described in further detail in the following subsections.

II. GITR Binding Molecules

The present invention provides isolated GITR binding molecules. Exemplary binding molecules of the present invention include the 6C8 antibody and the 2F8 antibody. The 6C8 antibody is an anti-GITR antibody that binds to GITR on T cells and dendritic cells, e.g., human T cells and dendritic cells, with high affinity. Preferably, such binding molecules abrogate the suppression of Teff cells by Treg cells and are agonistic to partially activated T cells in vitro in the presence of a stimulating agent, e.g., CD3.

In one embodiment, the a VH domain of a binding molecule of the invention comprises the amino acid sequence set forth in SEQ ID NO:1. (6C8 VH domain "N", including leader). It will be understood that although some of the sequences of binding molecules described herein include leader sequences, a binding molecule of the invention may also exclude the leader sequence, which is optional. For example, in one embodiment, a binding molecule of the invention comprises the amino acid sequence of the mature protein shown in SEQ ID NO:1. e.g., amino acids 20-138 of SEQ ID NO:1.

In one embodiment, the a VH domain of a binding molecule of the invention comprises the amino acid sequence set forth in SEQ ID NO:66. (6C8 VH domain "Q", including leader).

In one embodiment, the a VL domain of a binding molecule of the invention comprises the amino acid sequence set forth in SEQ ID NO:2. (6C8 VL domain, including leader).

In one embodiment, the a VH domain of a binding molecule of the invention comprises amino acid residues 20-138 of SEQ ID NO.:1. (6C8 VH domain "N", without leader).

In one embodiment, the a VH domain of a binding molecule of the invention comprises amino acid residues 20-138 of SEQ ID NO.:66. (6C8 VH domain "Q", without leader).

In one embodiment, the a VL domain of a binding molecule of the invention comprises amino acid residues 21-127 of SEQ ID NO.:2. (6C8 VL domain, without leader).

In one embodiment of the invention the VL chain comprises a leader and/or signal sequence, i.e., amino acid residues 1-20 of SEQ ID NO:2 (SEQ ID NO:59). In one embodiment, the VH chain comprises a leader and/or signal sequence, i.e., amino acid residues 1-19 of SEQ ID NO:1 (SEQ ID NO:64).

In one embodiment, a binding molecule of the invention comprisies a VH domain comprising a CDR set forth in SEQ ID NO:3. (6C8 VH CDR1).

In one embodiment, a binding molecule of the invention comprisies a VH domain comprising a CDR set forth in SEQ ID NO:4. (6C8 VH CDR2-"N").

In one embodiment, a binding molecule of the invention comprises a VH domain comprising a CDR set forth in SEQ ID NO:5. (6C8 VH CDR3).

In one embodiment, a binding molecule of the invention comprises a VH domain comprising a CDR set forth in SEQ ID NO:19. (6C8 VH CDR2-alternate "Q").

In one embodiment, a binding molecule of the invention comprisies a VL domain comprising a CDR set forth in SEQ ID NO:6. (6C8 VL CDR1).

In one embodiment, a binding molecule of the invention comprises a VL domain comprising a CDR set forth in SEQ ID NO:7. (6C8 VL CDR2).

In one embodiment, a binding molecule of the invention comprisies a VL domain comprising a CDR set forth in SEQ ID NO:8. (6C8 VL CDR3).

The invention also pertains to nucleic acid molecules encoding the above amino acid sequences.

In one embodiment, the a VH domain of a binding molecule of the invention comprises the nucleotide sequence set forth in SEQ ID NO:9. (6C8 VH domain, "N", including leader).

In one embodiment, the a VH domain of a binding molecule of the invention comprises the nucleotide sequence set forth in SEQ ID NO:65. (6C8 VH domain, "Q", including leader).

In one embodiment, the a VH domain of a binding molecule of the invention comprises nucleotides 58-414 of SEQ ID NO.:9. (6C8 VH domain, "N", without leader).

In one embodiment, the a VH domain of a binding molecule of the invention comprises nucleotides 58-414 of SEQ ID NO.:65. (6C8 VH domain, "Q", without leader).

In one embodiment, the a VL domain of a binding molecule of the invention comprises the nucleotide sequence set forth in SEQ ID NO:10. (6C8 VL domain, including leader).

In one embodiment, the a VL domain of a binding molecule of the invention comprises nucleotides 61-381 of SEQ ID NO.: 10. (6C8 VL domain, without leader).

In one embodiment, a binding molecule of the invention comprises a VH domain comprising a CDR the nucleic acid sequence of which is set forth in SEQ ID NO:11. (6C8 VH CDR1).

In one embodiment, a binding molecule of the invention comprises a VH domain comprising a CDR the nucleic acid sequence of which is set forth in SEQ ID NO:12. (6C8 VH CDR2-"AAT").

In one embodiment, a binding molecule of the invention comprises a VH domain comprising a CDR the nucleic acid sequence of which is set forth in SEQ ID NO:13. (6C8 VH CDR3).

In one embodiment, a binding molecule of the invention comprises a VH domain comprising a CDR the nucleic acid sequence of which is set forth in SEQ ID NO:65. (6C8 VH CDR2-alternate "CAA").

In one embodiment, a binding molecule of the invention comprises a VL domain comprising a CDR the nucleic acid sequence of which is set forth in SEQ ID NO:14. (6C8 VL CDR1).

In one embodiment, a binding molecule of the invention comprises a VL domain comprising a CDR the nucleic acid sequence of which is set forth in SEQ ID NO:15. (6C8 VL CDR2).

In one embodiment, a binding molecule of the invention comprises a VL domain comprising a CDR the nucleic acid sequence of which is set forth in SEQ ID NO:16. (6C8 VL CDR3).

In one embodiment, the a CL domain of a binding molecule of the invention comprises the amino acid sequence set forth in SEQ ID NO:20. (Murine IgG2a light chain constant region). In one embodiment, the a CH domain of a binding molecule of the invention comprises the amino acid sequence set forth in SEQ ID NO:21. (Murine IgG2a heavy chain constant region).

In one embodiment, a binding molecule of the invention comprises the amino acid sequence set forth in SEQ ID NO:22. (Chimeric-6C8 VL/human CL IgG1).

In one embodiment, a binding molecule of the invention comprises the amino acid sequence set forth in SEQ ID NO:23. (Chimeric Gly-6C8 VH/human CH IgG1).

In one embodiment, a binding molecule of the invention comprises the amino acid sequence set forth in SEQ ID NO:24. (Chimeric Agly-6C8 VH/human CH IgG1).

In one embodiment, a binding molecule of the invention comprises the amino acid sequence set forth in SEQ ID NO:44. (Humanized 6C8 VL).

In one embodiment, a binding molecule of the invention comprises the amino acid sequence set forth in SEQ ID NO:53. (Humanized 6C8 VH "N").

In one embodiment, a binding molecule of the invention comprises the amino acid sequence set forth in SEQ ID NO:54. (Humanized 6C8 VH "Q").

In one embodiment, the a CL domain of a binding molecule of the invention comprises the amino acid sequence set forth in SEQ ID NO:55. (Human IgG1 Gly heavy chain constant region).

In one embodiment, the a CH domain of a binding molecule of the invention comprises the amino acid sequence set forth in SEQ ID NO:56. (Human IgG1 Agly heavy chain constant region).

In one embodiment, the a CL domain of a binding molecule of the invention comprises the amino acid sequence set forth in SEQ ID NO:57. (Human IgG1 light chain constant region).

In one embodiment, a binding molecule of the invention comprises the amino acid sequence set forth in SEQ ID NO:58. (Complete Humanized 6C8 Light).

In one embodiment, a binding molecule of the invention comprises the amino acid sequence set forth in SEQ ID NO:60. (Complete Humanized 6C8 Heavy-HuN6C8-Gly).

In one embodiment, a binding molecule of the invention comprises the amino acid sequence set forth in SEQ ID NO:61. (Complete Humanized 6C8 Heavy-HuN6C8-Agly).

In one embodiment, a binding molecule of the invention comprises the amino acid sequence set forth in SEQ ID NO:62. (Complete Humanized 6C8 Heavy-HuQ6C8-Gly).

In one embodiment, a binding molecule of the invention comprises the amino acid sequence set forth in SEQ ID NO:63. (Complete Humanized 6C8 Heavy-HuQ6C8-Agly).

In one embodiment, a binding molecule of the invention has VL and VH sequences as shown in FIGS. 18A-18D; the amino acid sequence of the 6C8 VH region is also shown in SEQ ID NO: 1; the amino acid sequence of the 6C8 VL region is shown in SEQ ID NO: 2. In another embodiment, a binding molecule of the invention has LC and HC sequences as set forth in SEQ ID NOs:20 and 21;

```
                                                (SEQ ID NO: 20)
ADAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVKS

FNRNE;

(SEQ ID NO: 21)
AKTTPPSVYPLAPGCGDTTGSSVTLGCLVKGYFPESVTVTWNSGSLSSSV

HTFPALLQSGLYTMSSSVTVPSSTWPSQTVTCSVAHPASSTTVDKKLEPS

GPISTINPCPPCKECKCPAPNLEGGPSVFIFPPNIKDVLMISLTPKVTCV

VVDVSEDDPDVQISWFVNNVEVHTAQTQTHREDYNSTIRVVSTLPIQHQD

WMSGKEFKCKVNNKDLPSPIERTISKIKGLVRAQVYILPPPAEQLSRKDV

SLTCLVVGFNPGDISVEWTSNGHTEENYKDTAPVLDSDGSYFIYSKLNMK

TSKWEKTDSFSCNVRHEGLKNYYLKKTISRSPGK.
```

In one embodiment of the invention the VL chain comprises a leader and/or signal sequence, e.g., amino acid residues 1-20 of SEQ ID NO:2. In one embodiment, the VH chain comprises a leader and/or signal sequence, e.g., amino acid residues 1-19 of SEQ ID NO:1. In another embodiment, a binding molecule of the invention does not comprise a leader and/or signal sequence.

In one aspect, the invention pertains to 6C8 binding molecules and other binding molecules with equivalent properties to 6C8, such as high affinity binding to GITR and abrogation of suppression of Teff cells by Treg cells. In addition, the binding molecules of the invention do not induce apoptosis, nor do they inhibit a mixed lymphocyte reaction. Accordingly, equivalent binding molecules of the invention are GITR agonists, i.e., they induce signaling via GITR. GITR is a member of the TNFR superfamily. Since members of the TNFR family are involved in cell survival and apoptosis by signaling through NF-κB, in one embodiment, the binding molecules of the present invention attenuate degradation of I-κB.

In one embodiment, the invention provides isolated hGITR binding molecules with a light chain variable region (VL) comprising the amino acid sequence of SEQ ID NO: 2, and optionally a leader sequence, and a heavy chain variable region (VH) comprising the amino acid sequence of SEQ ID NO: 1, and optionally a leader sequence. In certain embodiments, a binding molecule comprises a heavy chain constant region, such as an IgG1, IgG2, IgG3, IgG4, IgA, IgE, IgM or IgD constant region. Furthermore, the binding molecule can comprise a light chain constant region, either a kappa light chain constant region or a lambda light chain constant region. Preferably, the binding molecule comprises a kappa light chain constant region. In one embodiment, a binding molecule of the invention comprises a light chain constant region as set forth in SEQ ID NO:20. In one embodiment, a binding molecule of the invention comprises a heavy chain constant region as set forth in SEQ ID NO:21. In one embodiment, a binding molecule of the invention comprises a heavy chain constant region as set forth in SEQ ID NO:55. In one embodiment, a binding molecule of the invention comprises a heavy chain constant region as set forth in SEQ ID NO:56. In one embodiment, a binding molecule of the invention comprises a heavy chain constant region as set forth in SEQ ID NO:57.

In another embodiment, the invention provides a binding molecule having 6C8-related VL CDR domains, for example, binding molecules with a light chain variable region (VL) having at least one CDR domain comprising an amino acid sequence selected from the group consisting of SEQ ID NO: 6, SEQ ID NO: 7, SEQ ID NO: 8. In another embodiment, a light chain variable region (VL) has at least two CDR domains comprising an amino acid sequence selected from the group consisting of SEQ ID NO: 6, SEQ ID NO: 7, SEQ ID NO: 8. In yet another embodiment, a light chain variable region (VL) has CDR domains comprising the amino acid sequences consisting of SEQ ID NO: 6, SEQ ID NO: 7, SEQ ID NO: 8.

In still other embodiments, the invention provides a binding molecule having 6C8-related VH CDR domains, for example, binding molecules with a light chain variable region (VH) having a CDR domain comprising an amino acid sequence selected from the group consisting of SEQ ID NO: 3, SEQ ID NO: 4, SEQ ID NO: 5, and SEQ ID NO:19. In another embodiment, a heavy chain variable region (VH) has at least two CDR domains comprising an amino acid sequence selected from the group consisting of SEQ ID NO: 3, SEQ ID NO: 4, SEQ ID NO: 5, and SEQ ID NO:19. In yet another embodiment, a heavy chain variable region (VH) has CDR domains comprising the amino acid sequences consisting of SEQ ID NO: 3, SEQ ID NO: 4, SEQ ID NO: 5, and SEQ ID NO:19.

In another embodiment, a binding molecule of the invention comprises at least one CDR derived from a murine anti-human GITR binding molecule, e.g., a 6C8 binding molecule. As used herein the term "derived from" a designated protein refers to the origin of the polypeptide. In one embodiment, the polypeptide or amino acid sequence which is derived from a particular starting polypeptide is a CDR sequence or sequence related thereto. In another embodiment, the polypeptide or amino acid sequence which is derived from a particular starting polypeptide is a FR sequence or sequence related thereto. In one embodiment, the amino acid sequence which is derived from a particular starting polypeptide is not contiguous.

For example, in one embodiment, one, two, three, four, five, or six CDRs are derived from a murine 6C8 antibody. In one embodiment, a binding molecule of the invention comprises at least one heavy or light chain CDR of a murine 6C8 antibody. In another embodiment, a binding molecule of the invention comprises at least two CDRs from a murine 6C8 antibody. In another embodiment, a binding molecule of the invention comprises at least three CDRs from a murine 6C8 antibody. In another embodiment, a binding molecule of the invention comprises at least four CDRs from a murine 6C8 antibody. In another embodiment, a binding molecule of the invention comprises at least five CDRs from a murine 6C8 antibody. In another embodiment, a binding molecule of the invention comprises at least six CDRs from a murine 6C8 antibody.

It will also be understood by one of ordinary skill in the art that a binding molecule of the invention may be modified such that they vary in amino acid sequence from the 6C8 molecule from which they were derived. For example, nucleotide or amino acid substitutions leading to conservative substitutions or changes at "non-essential" amino acid residues may be made (e.g., in CDR and/or framework residues) and maintain the ability to bind to GITR, e.g., human GITR.

In one embodiment, the at least one CDR (or at least one CDR from the greater than one 6C8 CDRs that are present in the binding molecule) is modified to vary in sequence from the CDR of a naturally occurring 6C8 binding molecule, yet retains the ability to bind to 6C8. For example, in one embodiment, one or more CDRs from a 6C8 antibody are modified to remove potential glycosylation sites. For example, since the amino acid sequence Asn-X—(Ser/Thr) is a putative consensus sequence for a glycosylation site which may affect the production of the binding molecule, and CDR2 of the 6C8 heavy chain has the sequence Asn- Pro-Ser, a second version of the heavy chain was prepared to conservatively substitute a glutamine (Gln) for an asparagine (Asn) at amino acid residue 62 of SEQ ID NO:53.

In one embodiment, a binding molecule of the invention comprises a polypeptide or amino acid sequence that is essentially identical to that of a 6C8 antibody, or a portion thereof wherein the portion consists of at least 3-5 amino acids, of at least 5-10 amino acids, at least 10-20 amino acids, at least 20-30 amino acids, or at least 30-50 amino acids, or which is otherwise identifiable to one of ordinary skill in the art as having its origin in the starting sequence.

In another embodiment, the polypeptide or amino acid sequence which is derived from a particular starting polypeptide or amino acid sequence shares an amino acid sequence identity that is about 80%, 85%, 86%, 87%, 88%, 89%, 90%, 91%, 92%, 93%, 94%, 95%, 96%, 97%, 98%, 99%, or which is otherwise identifiable to one of ordinary skill in the art as having its origin in the starting sequence.

An isolated nucleic acid molecule encoding a non-natural variant of a polypeptide can be created by introducing one or more nucleotide substitutions, additions or deletions into the nucleotide sequence of the binding molecule such that one or more amino acid substitutions, additions or deletions are introduced into the encoded protein. Mutations may be introduced by standard techniques, such as site-directed mutagenesis and PCR-mediated mutagenesis. In one embodiment, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding molecule polypeptide may be replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the binding molecule coding sequence.

Preferred binding molecules of the invention comprise framework and constant region amino acid sequences derived from a human amino acid sequence. However, binding molecules may comprise framework and/or constant region sequences derived from another mammalian species. For example, a primate framework region (e.g., non-human primate), heavy chain portion, and/or hinge portion may be included in the subject binding molecules. In one embodiment, one or more murine amino acids may be present in the framework region of a binding polypeptide, e.g., a human or non-human primate framework amino acid sequence may comprise one or more amino acid substitutions and/or back-mutations in which the corresponding murine amino acid residue is present. Preferred binding molecules of the invention are less immunogenic than the starting 6C8 murine antibody.

The present invention also features chimeric and/or humanized binding molecules (i.e., chimeric and/or humanized immunoglobulins) specific for GITR. Chimeric and/or humanized binding molecules have the same or similar binding specificity and affinity as a mouse or other nonhuman binding molecules that provide the starting material for construction of a chimeric or humanized binding molecule.

A chimeric binding molecule is one whose light and heavy chain genes have been constructed, typically by genetic engineering, from immunoglobulin gene segments belonging to different species. For example, the variable (V) segments of the genes from a mouse monoclonal binding molecule may be joined to human constant (C) segments, such as IgG1 or IgG4. Human isotype IgG1 is preferred. An exemplary chimeric binding molecule is thus a hybrid protein consisting of the V or antigen-binding domain from a mouse binding molecule and the C or effector domain from a human binding molecule.

In one embodiment, the invention pertains to humanized variable regions of the 6C8 binding molecule and polypeptides comprising such humanized variable regions. In one embodiment, a binding molecule of the invention comprises at least one humanized 6C8 binding molecule variable region, e.g., a light chain or heavy chain variable region.

The term "humanized binding molecule" refers to a binding molecule comprising at least one chain comprising variable region framework residues derived from a human binding molecule chain (referred to as the acceptor immunoglobulin or binding molecule) and at least one complementarity determining region derived from a mouse-binding molecule, (referred to as the donor immunoglobulin or binding molecule). Humanized binding molecules can be produced using recombinant DNA technology, which is discussed below. See for example, e.g., Hwang, W. Y. K., et al. (2005) *Methods* 36:35; Queen et al., Proc. Natl. Acad. Sci. USA, (1989), 86:10029-10033; Jones et al., Nature, (1986), 321:522-25; Riechmann et al., Nature, (1988), 332:323-27; Verhoeyen et al., Science, (1988), 239:1534-36; Orlandi et al., Proc. Natl. Acad. Sci. USA, (1989), 86:3833-37; U.S. Pat. Nos. 5,225,539; 5,530,101; 5,585,089; 5,693,761; 5,693,762; 6,180,370, Selick et al., WO 90/07861, and Winter, U.S. Pat. No. 5,225,539 (incorporated by reference in their entirety for all purposes). The constant region(s), if present, are preferably is also derived from a human immunoglobulin.

When a preferred non-human donor binding molecule has been selected for humanization, an appropriate human acceptor binding molecule may be obtained, e.g., from sequence databases of expressed human antibody genes, from germline Ig sequences or a consensus sequence of several human binding molecules.

In one embodiment, a CDR homology based method is used for humanization (see, e.g., Hwang, W. Y. K., et al. (2005) Methods 36:35, the contents of which is incorporated in its entirety herein by this reference). This method generally involves substitution of mouse CDRs into a human variable domain framework based on similarly structured mouse and human CDRs rather than similarly structured mouse and human frameworks. The similarity of the mouse and human CDRs is generally determined by identifying human genes of the same chain type (light or heavy) that have the same combination of canonical CDR structures as the mouse binding molecules and thus retain three-dimensional conformation of CDR peptide backbones. Secondly, for each of the candidate variable genes with matching canonical structures, residue to residue homology between the mouse and candidate human CDRs is evaluated. Finally, to generate a humanized binding molecule, CDR residues of the chosen human candidate CDR not already identical to the mouse CDR are converted to the mouse sequence. In one embodiment, no mutations of the human framework are introduced into the humanized binding molecule.

In one embodiment, human germline sequences are evaluated for CDR homology to the GITR binding molecule CDRs. For example, for the murine 6C8 antibody, all germ line light chain kappa chain V genes with a 2-1-1 canonical structure in the IMGT database were compared with the 6C8 antibody sequence. The same was done for the heavy chain where all 3-1 germ line heavy chain V genes were compared to the 6C8 amino acid sequence. Accordingly, in one embodiment, a binding molecule of the invention comprises a human kappa chain V region framework with a 2-1-1 canonical structure. In another embodiment, a binding molecule of the invention comprises a human heavy chain V region framework with a 3-1 canonical structure.

The following potential human light chain germline sequences were identified and may be incorporated into a binding molecule of the invention:

The IMGT accession number of the IGKV3-15 gene is M23090. The amino acid sequence is:

(SEQ ID NO: 25)
EIVMTQSPATLSVSPGERATLSCRASQSVSSNLAWYQQKPGQAPRLLIYG

ASTRATGIPARFSGSGSGTEFTLTISSLQSEDFAVYYCQQYNNWP.

The IMGT accession number of the IGKV3D-11 gene is X17264. The amino acid sequence is:

(SEQ ID NO: 26)
EIVLTQSPATLSLSPGERATLSCRASQGVSSYLAWYQQKPGQAPRLLIYD

ASNRATGIPARFSGSGPGTDFTLTISSLEPEDFAVYYCQQRSNWH.

There are two alleles of the IGKV3-11 gene. The IMGT accession number of allele *01 of the IGKV3-11gene is X01668. The amino acid sequence is:

(SEQ ID NO: 27)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWP.

The IMGT accession number of allele *02 of the IGKV3-11gene is K02768. The amino acid sequence is:

(SEQ ID NO: 28)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWP.

The IMGT accession number of the IGKV1D-43 gene is X72817. The amino acid sequence is:

(SEQ ID NO: 29)
AIRMTQSPFSLSASVGDRVTITCWASQGISSYLAWYQQKPAKAPKLFIYY

ASSLQSGVPSRFSGSGSGTDYTLTISSLQPEDFATYYCQQYYSTP.

There are two alleles of the IGKV1-39 gene. The IMGT accession number of allele *01 of the IGKV1-39 gene is X59315. The amino acid sequence is:

(SEQ ID NO: 30)
DIQMTQSPSSLSASVGDRVTITCRASQSISSYLNWYQQKPGKAPKILIYA

ASSLQSGVPSRFSGSGSGTDFTLTISSLQPEDFATYYCQQSYSTP.

The IMGT accession number of allele *02 of the IGKV1-39 gene is X59318. The amino acid sequence is:

(SEQ ID NO: 31)
DIQMTQSPSFLSASVGDRVTITCRASQSISSYLNWYQQKPGKAPKLLIYA

ASSLQSGVPSRFSGSGSGTDFTLTISSLQPEDFATYYCQCGYSTP.

The IMGT accession number of the IGKV1-33 gene is M64856. The amino acid sequence is:

(SEQ ID NO: 32)
DIQMTQSPSSLSASVGDRVTITCQASQDISNYLNWYQQKPGKAPKLLIYD

ASNLETGVPSRFSGSGSGTDFTFTISSLQPEDIATYYCQQYDNLP.

The IMGT accession number of the IGKV1-27 gene is X63398. The amino acid sequence is:

(SEQ ID NO: 33)
DIQMTQSPSSLSASVGDRVTITCRASQGISNYLAWYQQKPGKVPKLLIYA

ASTLQSGVPSRFSGSGSGTDFTLTISSLQPEDVATYYCQKYNSAP.

There are two alleles of the IGKV1-17 gene. The IMGT accession number of allele *01 of the IGKV1-17 gene is X72808. The amino acid sequence is:

(SEQ ID NO: 34)
DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYP.

The IMGT accession number of allele *02 of the IGKV1-17 gene is D88255. The amino acid sequence is:

(SEQ ID NO: 35)
DIQMTQSPSSLSASVGDRVTITCRASQGIRNDLGWYQQKPGKAPKRLIYA

ASSLQSGVPSRFSGSGSGTEFTLTISNLQPEDFATYYCLQHNSYP.

There are two alleles of the IGKV1D-16 gene. The IMGT accession number of allele *01 of the IGKV1D-16 gene is K01323. The amino acid sequence is:

(SEQ ID NO: 36)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYP.

The IMGT accession number of allele *02 of the IGKV1D-16 gene is J00244. The amino acid sequence is:

(SEQ ID NO: 37)
DIQMTQSPSSLSASVGDRVTITCRARQGISSWLAWYQQKPEKAPKSLIYA

ASSLQSGVPSRFSGSGSGTDFTLTISSLQPEDFATYYCQQYNSYP.

The IMGT accession number of the IGKV1-16 gene is J00248. The amino acid sequence is:

(SEQ ID NO: 38)
DIQMTQSPSSLSASVGDRVTITCRASQGISNYLAWFQQKPGKAPKSLIYA

ASSLQSGVPSRFSGSGSGTDFTLTISSLQPEDFATYYCQQYNSYP.

There are two alleles of the IGKV 1-12 gene. The IMGT accession number of allele *01 of the IGKV1-12 gene is V01577. The amino acid sequence is:

(SEQ ID NO: 39)
DIQMTQSPSSVSASVGDRVTITCRASQGISSWLAWYQQKPGKAPKLLIYA

ASSLQSGVPSRFSGSGSGTDFTLTISSLQPEDFATYYCQQANSFP.

The IMGT accession number of allele *02 of the IGKV1-12 gene is V01576. The amino acid sequence is:

(SEQ ID NO: 40)
DIQMTQSPSSVSASVGDRVTITCRASQGISSWLAWYQQKPGKAPKLLIYA

ASSLQSGVPSRFSGSGSGTDFTLTISSLQPEDFATYYCQQANSFP.

The IMGT accession number of the IGKV1-9 gene is Z00013. The amino acid sequence is:

(SEQ ID NO: 41)
DIQLTQSPSFLSASVGDRVTITCRASQGISSYLAWYQQKPGKAPKLLIYA

ASTLQSGVPSRFSGSGSGTEFTLTISSLQPEDFATYYCQQLNSYP.

The IMGT accession number of the IGKV1-6 gene is M64858. The amino acid sequence is:

(SEQ ID NO: 42)
AIQMTQSPSSLSASVGDRVTITCRASQGIRNDLGWYQQKPGKAPKLLIYA

ASSLQSGVPSRFSGSGSGTDFTLTISSLQPEDFATYYCLQDYNYP.

There are three alleles of the IGKV1-5 gene. The IMGT accession number of allele *01 of the IGKV1-5 gene is Z00001. The amino acid sequence is:

(SEQ ID NO: 43)
DIQMTQSPSTLSASVGDRVTITCRASQSISSWLAWYQQKPGKAPKLLIYD

ASSLESGVPSRFSGSGSGTEFTLTISSLQPDDFATYYCQQYNSYS.

The following potential human heavy chain germline sequences were identified and may be incorporated into a binding molecule of the invention:

There are ten alleles of the IGHV2-5 gene. The IMGT accession number of allele *01 of the IGHV2-5 gene is X62111. The amino acid sequence is:

(SEQ ID NO: 45)
QITLKESGPTLVKPTQTLTLTCTFSGFSLSTSGVGVGWIRQPPGKALEWL

ALIYWNDDKRYSPSLKSRLTITKDTSKNQVVLTMTNMDPVDTATYY.

The IMGT accession number of the IGHV2-26 gene is M99648. The amino acid sequence is:

(SEQ ID NO: 46)
QVTLKESGPVLVKPTETLTLTCTVSGFSLSNARMGVSWIRQPPGKALEWL

AHIFSNDEKSYSTSLKSRLTISKDTSKSQVVLTMTNMDPVDTATYYCA

RI.

There are thirteen alleles of the IGHV2-70 gene. The IMGT accession number of allele *01 of the IGHV2-70 gene is L21969. The amino acid sequence is:

(SEQ ID NO: 47)
QVTLRESGPALVKPTQTLTLTCTFSGFSLSTSGMCVSWIRQPPGKALEWL

ALIDWDDDKYYSTSLKTRLTISKDTSKNQVVLTMTNMDPVDTATYYCA

RI.

There are four alleles of the IGHV4-30-2 gene. The IMGT accession number of allele *01 of the IGHV4-30-2 gene is L 10089. The amino acid sequence is:

(SEQ ID NO: 48)
QLQLQESGSGLVKPSQTLSLTCAVSGGSISSGGYSWSWIRQPPGKGLEWI

GYIYHSGSTYYNPSLKSRVTISVDRSKNQFSLKLSSVTAADTAVYYCAR.

There are six alleles of the IGHV4-30-4 gene. The IMGT accession number of allele *01 of the IGHV4-30-4 gene is Z14238. The amino acid sequence is:

(SEQ ID NO: 49)
QVQLQESGPGLVKPSQTLSLTCTVSGGSISSGDYYWSWIRQPPGKGLEWI

GYIYYSGSTYYNPSLKSRVTISVDTSKNQFSLKLSSVTAADTAVYYCAR.

There are ten alleles of the IGHV4-31 gene. The IMGT accession number of allele *01 of the IGHV2-5 gene is L10098. The amino acid sequence is:

(SEQ ID NO: 50)
QVQLQESGPGLVKPSQTLSLTCTVSGGSISSGGYYWSWIRQHPGKGLEWI

GYIYYSGSTYYNPSLKSLVTISVDTSKNQFSLKLSSVTAADTAVYYCAR.

There are six alleles of the IGHV4-39 gene. The IMGT accession number of allele *01 of the IGHV4-39 gene is L10094. The amino acid sequence is:

(SEQ ID NO: 51)
QLQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCAR.

There are eight alleles of the IGHV4-61 gene. The IMGT accession number of allele *01 of the IGHV4-61 gene is M29811. The amino acid sequence is:

(SEQ ID NO: 52)
QVQLQESGPGLVKPSETLSLTCTVSGGSVSSGSYYWSWIRQPPGKGLEWI

GYIYYSGSTNYNPSLKSRVTISVDTSKNQFSLKLSSVTAADTAVYYCAR.

Each of these germline sequences may be used to provide framework regions for use with one or more 6C8 CDRs.

As used herein, "canonical structures" are conserved hypervariable loop conformations made by different CDRs by which the binding molecule forms the antigen contacts. The assignment of canonical structure classes to a new binding molecule can be achieved using publicly available software.

In another embodiment, the substitution of mouse CDRs into a human variable domain framework is based on the retention of the correct spatial orientation of the mouse variable domain framework by identifying human variable domain frameworks which will retain the same conformation as the mouse variable domain frameworks from which the CDRs were derived. In one embodiment, this is achieved by obtaining the human variable domains from human binding molecules whose framework sequences exhibit a high degree of sequence identity with the murine variable framework domains from which the CDRs were derived. See Kettleborough et al., *Protein Engineering* 4:773 (1991); Kolbinger et al., *Protein Engineering* 6:971 (1993) and Carter et al., WO 92/22653.

Preferably the human acceptor binding molecule retains the canonical and interface residues of the donor binding molecule. Additionally, the human acceptor binding molecule preferably has substantial similarity in the length of CDR loops. See Kettleborough et al., Protein Engineering 4:773 (1991); Kolbinger et al., Protein Engineering 6:971 (1993) and Carter et al., WO 92/22653.

In another embodiment, appropriate human acceptor sequences may be selected based on homology to framework regions of the 6C8 binding molecule. For example, the amino acid sequence of the 6C8 binding molecule may be compared to the amino acid sequence of other known binding molecules by, for example, by comparing the FR regions or the variable region sequences of the 6C8 amino acid sequence against a publicly available database of known binding molecules and selecting those sequences with the highest percent identity of amino acids in the variable or FR region, i.e., 80%, 85%, 86%, 87%, 88%, 89%, 90%, 91%, 92%, 93%, 94%, 95%, 96%, 97%, 98%, 99%, 99.5%. In one embodiment, the framework sequence set forth in SEQ ID NO:67 may be used (QVTLKESGPGILQPSQTLSLTCSFSGF-SLSTSGMGVGWIRQPSGKGLEWL AHIWWD-DDKYNPSLKSRLTISKDTSSNQVFL-KITSVDTRDTATYYCARTRR YFPFAYWGEGTSVTVTS (SEQ ID NO:67; Framework residues are in bold)). In another embodiment, the framework sequence set forth in SEQ ID NO:68 may be used (QVTLRESGPALVKPTQTLTLTCTF-SGFSLSTSGMGVGWIRQPPGKALEW LAHIWWD-DDKYNPSLKSRLTISKDTSKNQVVLTMT-NMDPVDTATYYCAR TRRYFPFAYWGQGTLVTVSS (SEQ ID NO:68; Framework residues are in bold)).

Having identified the complementarity determining regions of the murine donor immunoglobunlin and appropriate human framework acceptor immunoglobulins, the next step is to determine which; if any, residues from these components should be substituted to optimize the properties of the resulting humanized binding molecule. In general, substitution of human amino acid residues with murine should be minimized, because introduction of murine residues increases the risk of the binding molecule eliciting a human-anti-mouse-antibody (HAMA) response in humans. Art-recognized methods of determining immune response can be performed to monitor a HAMA response in a particular patient or during clinical trials. Patients administered humanized binding molecules can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (using a BIAcore™ system) and/or solid-phase ELISA analysis.

When necessary, one or more residues in the human framework regions can be changed or substituted to residues at the corresponding positions in the murine antibody so as to preserve the binding affinity of the humanized antibody to the antigen. This change is sometimes called "backmutation". Certain amino acids from the human variable region framework residues are selected for back mutation based on their possible influence on CDR conformation and/or binding to antigen. The placement of murine CDR regions with human variable framework region can result in conformational restraints, which, unless corrected by substitution of certain amino acid residues, lead to loss of binding affinity.

In one embodiment, the selection of amino acid residues for backmutation can be determined, in part, by computer modeling, using art recognized techniques. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid may be substituted by the equivalent framework amino acid from the mouse binding molecule when it is reasonably expected that the amino acid: (1) noncovalently binds antigen directly, (2) is adjacent to a CDR region, (3) otherwise interacts with a CDR region (e.g., is within about 3-6 Å of a CDR region as determined by computer modeling), or (4) participates in the VL-VH interface.

Residues which "noncovalently bind antigen directly" include amino acids in positions in framework regions which are have a good probability of directly interacting with amino acids on the antigen according to established chemical forces, for example, by hydrogen bonding, Van der Waals forces, hydrophobic interactions, and the like.

Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk *JMB* 196:901 (1987)). These amino acids are particularly likely to interact with the amino acids in the CDRs and, if chosen from the acceptor, may distort the donor CDRs and reduce affinity. Moreover, the adjacent amino acids may interact directly with the antigen (Amit et al., *Science*, 233:747 (1986), which is incorporated herein by reference) and selecting these amino acids from the donor may be desirable to keep all the antigen contacts that provide affinity in the original binding molecule.

Residues that "otherwise interact with a CDR region" include those that are determined by secondary structural analysis to be in a spatial orientation sufficient to effect a CDR region. In one embodiment, residues that "otherwise interact with a CDR region" are identified by analyzing a three-dimensional model of the donor immunoglobulin (e.g., a computer-generated model). A three-dimensional model, typically of the original donor binding molecule, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 Å of some atom in the CDRs and must contain an atom that could interact with the CDR atoms according to established chemical forces, such as those listed above.

In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact binding molecule, and (2) in a hypothetical molecule consisting of the binding molecule with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an binding molecule, using algorithms known in the art (e.g., Connolly, *J. Appl. Cryst.* 16:548 (1983) and Lee and Richards, *J. Mol. Biol.* 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many binding molecules (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26-30, 71 and 94 of the heavy chain (numbering according to Kabat) are known to be capable of interacting with the CDRs in many binding molecules. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized binding molecule.

Residues which "participate in the VL-VH interface" or "packing residues" include those residues at the interface between VL and VH as defined, for example, by Novotny and Haber (*Proc. Natl. Acad. Sci. USA*, 82:4592-66 (1985)) or Chothia et al, supra. Generally, unusual packing residues should be retained in the humanized binding molecule if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant binding molecules are produced, one of which has that particular substitution, the other of which does not. Alternative variant binding molecules so produced can be tested in any of the assays described herein for the desired activity, and the preferred binding molecule selected.

Usually the CDR regions in humanized binding molecules are substantially identical, and more usually, identical to the corresponding CDR regions of the donor binding molecule. Although not usually desirable, it is sometimes possible to make one or more conservative amino acid substitutions of CDR residues without appreciably affecting the binding affinity of the resulting humanized binding molecule. By conservative substitutions it is meant combinations such as Gly, Ala; Val, Ile, Leu; Asp, Glu; Asn, Gln; Ser, Thr; Lys, Arg; and Phe, Tyr.

Additional candidates for substitution are acceptor human framework amino acids that are unusual or "rare" for a human immunoglobulin at that position. These amino acids can be substituted with amino acids from the equivalent position of the mouse donor binding molecule or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criterion help ensure that an atypical amino acid in the human framework does not disrupt the binding molecule structure. Moreover, by replacing an unusual human acceptor amino acid with an amino acid from the donor binding molecule that happens to be typical for human binding molecules, the humanized binding molecule may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions. Notably, CDR1 in the variable heavy chain is defined as including residues 26-32.

Additional candidates for substitution are acceptor framework residues that correspond to a rare or unusual donor framework residue. Rare or unusual donor framework residues are those that are rare or unusual (as defined herein) for murine binding molecules at that position. For murine binding molecules, the subgroup can be determined according to Kabat and residue positions identified which differ from the consensus. These donor specific differences may point to somatic mutations in the murine sequence which enhances activity. Unusual residues that are predicted to affect binding are retained, whereas residues predicted to be unimportant for binding can be substituted.

Additional candidates for substitution are non-germline residues occurring in an acceptor framework region. For example, when an acceptor binding molecule chain (i.e., a human binding molecule chain sharing significant sequence identity with the donor binding molecule chain) is aligned to a germline binding molecule chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized binding molecules are usually substantially identical, and more usually, identical to the framework regions of the human binding molecules from which they were derived. Of course, many of the amino acids in the framework region make little or no direct contribution to the specificity or affinity of a binding molecule. Thus, many individual conservative substitutions of framework residues can be tolerated without appreciable change of the specificity or affinity of the resulting humanized binding molecule. Thus, in one embodiment the variable framework region of the humanized binding molecule shares at least 85% sequence identity to a human variable framework region sequence or consensus of such sequences. In another embodiment, the variable framework region of the humanized binding molecule shares at least 90%, preferably 95%, more preferably 96%, 97%, 98% or 99% sequence identity to a human variable framework region sequence or consensus of such sequences. In general, however, such substitutions are undesirable.

In one embodiment, a binding molecule of the invention further comprises at least one backmutation of a human amino acid residue to the corresponding mouse amino acid residue where the amino acid residue is an interface packing residue. "Interface packing residues" include those residues at the interface between VL and VH as defined, for example, by Novotny and Haber, Proc. Natl. Acad. Sci. USA, 82:4592-66 (1985).

In one embodiment, a binding molecule of the invention further comprises at least one backmutation of a human amino acid residue to the corresponding mouse amino acid residue is a canonical residue. "Canonical residues" are conserved framework residues within a canonical or structural class known to be important for CDR conformation (Tramontano et al., J. Mol. Biol. 215:175 (1990), all of which are incorporated herein by reference). Canonical residues include 2, 25, 27B, 28, 29, 30, 33, 48, 51, 52, 64, 71, 90, 94 and 95 of the light chain and residues 24, 26, 27 29, 34, 54, 55, 71 and 94 of the heavy chain. Additional residues (e.g., CDR structure-determining residues) can be identified according to the methodology of Martin and Thorton (1996) J. Mol. Biol. 263:800.

In one embodiment, a binding molecule of the invention further comprises at least one backmutation of a human amino acid residue to the corresponding mouse amino acid residue where the amino acid residue is at a position capable of interacting with a CDR. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs.

Based on CLUSTAL W analysis, several amino acid residues in the human framework were identified for potential substitution, e.g., with corresponding amino acid residues from the 6C8 light chain. These included positions 1, 8, 9, 10, 11, 13, 15, 17, 19, 20, 21, 22, 43, 45, 46, 58, 60, 63, 70, 76, 77, 78, 79, 83, 85, 87, 100, and 104.

In one embodiment, a variable light chain framework of a binding molecule of the invention further comprises at least one substitution of a human amino acid residue to the corresponding mouse amino acid residue selected from the group consisting of: E1D (i.e., the E at position 1 of the CDR-grafted antibody which comprises murine CDRs and human FR regaions is mutated to a D, which is the corresponding amino acid residue in the 6C8 antibody), P8Q, A9K, T10F, L11M, V13T, P15V, E17D, A19V, T20S, L21V, S22T, A43S, R45K, L46A, I58V, A60D, S63T, E70D, S76N, S77N, L78V, Q79H, F83L, V85E, Y87F, G100A, and V104L.

Based on CLUSTAL W analysis, several amino acid residues in the human framework were identified for potential substitution, e.g., with corresponding amino acid residues from the 6C8 heavy chain. These included positions 5, 10, 11, 12, 15, 19, 23, 43, 46, 68, 77, 81, 83, 84, 86, 87, 89, 90, and 92.

In one embodiment, a variable heavy chain framework of a binding molecule of the invention further comprises at least one substitution of a human amino acid residue to the corresponding mouse amino acid residue selected from the group consisting of: R5K (i.e., the R at position 5 of the CDR-grafted antibody which comprises murine CDRs and human FR regaions is mutated to a K, which is the corresponding amino acid residue in the 6C8 antibody), A10G, L11I, V12L, T15S, T19S, T23S, P43S, A46G, R68Q, K77R, V81F, T83K, M84I, N86S, M87V, P89T, V90A, and T92A.

The humanized binding molecules preferably exhibit a specific binding affinity for antigen of at least $10^7$, $10^8$, $10^9$ or $10^{10}$ M$^{-1}$. Usually the upper limit of binding affinity of the humanized binding molecules for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized binding molecule having no substitutions (e.g., a binding molecule having donor CDRs and acceptor FRs, but no FR substitutions). In such instances, the binding of the optimized binding molecule (with substitutions) is preferably at least two- to three-fold greater, or three- to four-fold greater, than that of the unsubstituted binding molecule. For making comparisons, activity of the various binding molecules can be determined, for example, by BIAcore™ (i.e., surface plasmon resonance using unlabelled reagents) or competitive binding assays.

Having conceptually selected the CDR and framework components of humanized binding molecules, a variety of methods are available for producing such binding molecules. Because of the degeneracy of the code, a variety of nucleic acid sequences will encode each binding molecule amino acid sequence. The desired nucleic acid sequences can be produced by de novo solid-phase DNA synthesis or by PCR mutagenesis of an earlier prepared variant of the desired polynucleotide.

Oligonucleotide-mediated mutagenesis is a preferred method for preparing substitution, deletion and insertion variants of target polypeptide DNA. See Adelman et al. (DNA 2:183 (1983)). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

The variable segments of binding molecules produced as described supra (e.g., the heavy and light chain variable regions of chimeric, humanized, or human binding molecules) are typically linked to at least a portion of an immunoglobulin constant region (Fc), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the binding molecule will contain both light chain and heavy chain constant regions. The heavy chain constant region usually includes CH1, hinge, CH2, CH3, and CH4 regions. A binding molecule described herein include antibodies having all types of constant regions, including IgM, IgG, IgD, IgA and IgE, and any isotype, including IgG1, IgG2, IgG3 and IgG4. The choice of constant region depends, in part, or whether binding molecule-dependent complement and/or cellular mediated toxicity is desired. For example, isotopes IgG1 and IgG3 have complement activity and isotypes IgG2 and IgG4 do not. When it is desired that the binding molecule (e.g., humanized binding molecule) exhibit cytotoxic activity, the constant domain is usually a complement fixing constant domain and the class is typically IgG1. When such cytotoxic activity is not desirable, the constant domain may be, e.g., of the IgG2 class. Choice of isotype can also affect passage of antibody into the brain. Human isotype IgG1 is preferred. Light chain constant regions can be lambda or kappa. The humanized binding molecule may comprise sequences from more than one class or isotype. Binding molecules can be expressed as tetramers containing two light and two heavy chains, as separate heavy chains, light chains, as Fab, Fab' F(ab')2, and Fv, or as single chain binding molecules in which heavy and light chain variable domains are linked through a spacer.

III. Production of Binding Molecules

The present invention features binding molecules having specificity for GITR, e.g., human GITR. Such binding molecules can be used in formulating various therapeutic compositions of the invention or, preferably, provide complementarity determining regions for the production of humanized or chimeric binding molecules (described in detail below). The production of non-human monoclonal binding molecules, e.g., murine, guinea pig, primate, rabbit or rat, can be accomplished by, for example, immunizing the animal with GITR or with a nucleic acid molecule encoding GITR. For example, the 6C8 binding molecule was made by placing the gene encoding human GITR in an expression vector and immunizing animals. A longer polypeptide comprising GITR or an immunogenic fragment of GITR or anti-idiotypic binding molecule of GITR can also be used. (see, for example, Harlow & Lane, supra, incorporated by reference for all purposes). Such an immunogen can be obtained from a natural source, by peptide synthesis or by recombinant expression. Optionally, the immunogen can be administered, fused or otherwise complexed with a carrier protein, as described below. Optionally, the immunogen can be administered with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages. Several types of adjuvants can be used as described below. Complete Freund's adjuvant followed by incomplete adjuvant is preferred for immunization of laboratory animals.

Rabbits or guinea pigs are typically used for making polyclonal binding molecules. Exemplary preparation of polyclonal binding molecules, e.g., for passive protection, can be performed as follows. Animals are immunized with 100 µg GITR, plus adjuvant, and euthanized at 4-5 months. Blood is collected and IgG is separated from other blood components. Binding molecules specific for the immunogen may be partially purified by affinity chromatography. An average of about 0.5-1.0 mg of immunogen-specific binding molecule is obtained per animal, giving a total of 60-120 mg.

Mice are typically used for making monoclonal binding molecules. Monoclonals can be prepared against a fragment by injecting the fragment or longer form of GITR into a mouse, preparing hybridomas and screening the hybridomas for a binding molecule that specifically binds to GITR. Optionally, binding molecules are screened for binding to a specific region or desired fragment of GITR without binding to other nonoverlapping fragments of GITR. The latter screening can be accomplished by determining binding of a binding molecule to a collection of deletion mutants of a GITR peptide and determining which deletion mutants bind to the binding molecule. Binding can be assessed, for example, by Western blot or ELISA. The smallest fragment to show specific binding to the binding molecule defines the epitope of the binding molecule. Alternatively, epitope specificity can be determined by a competition assay in which a test and reference binding molecule compete for binding to GITR. If the test and reference binding molecule compete, then they bind to the same epitope (or epitopes sufficiently proximal) such that binding of one binding molecule interferes with binding of the other. The preferred isotype for such binding molecules is mouse isotype IgG2a or equivalent isotype in other species. Mouse isotype IgG2a is the equivalent of human isotype IgG1.

In another embodiment, DNA encoding a binding molecule may be readily isolated and sequenced using conventional procedures (e.g., by using oligonucleotide probes that are capable of binding specifically to genes encoding the heavy and light chains of murine binding molecules). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture of binding molecules as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. Transformed cells expressing the desired antibody may be produced in relatively large quantities to provide clinical and commercial supplies of the binding molecule.

Those skilled in the art will also appreciate that DNA encoding binding molecules or fragments thereof (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. Immunol. Today 21:371; Nagy et al. 2002. Nat. Med. 8:801; Huie et al. 2001. Proc. Natl. Acad. Sci. USA 98:2682; Lui et al. 2002. J. Mol. Biol. 315:1063, each of which is incorporated herein by reference. Several publications (e.g., Marks et al. Bio/Technology 10:779-783 (1992)) have described the production of high affinity human binding molecules by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. Nat. Biotechnol. 18:1287; Wilson et al. 2001. Proc. Natl. Acad. Sci. USA 98:3750; or Irving et al. 2001 J. Immunol. Methods 248:31. In yet another embodiment, cell surface libraries can be screened for binding molecules (Boder et al. 2000. Proc. Natl. Acad. Sci. USA 97:10701; Daugherty et al. 2000 J. Immunol. Methods 243:211. Such procedures provide alternatives to traditional hybridoma techniques for the isolation and subsequent cloning of monoclonal binding molecules.

Yet other embodiments of the present invention comprise the generation of human or substantially human binding molecules in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human binding molecules upon antigen challenge. Another preferred means of generating human binding molecules using SCID mice is disclosed in U.S. Pat. No. 5,811,524 which is incorporated herein by reference. It will be appreciated that the genetic material associated with these human binding molecules may also be isolated and manipulated as described herein.

Yet another highly efficient means for generating recombinant binding molecules is disclosed by Newman, Biotechnology, 10: 1455-1460 (1992). Specifically, this technique results in the generation of primatized binding molecules that contain monkey variable domains and human constant sequences. This reference is incorporated by reference in its entirety herein. Moreover, this technique is also described in U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or synthetic to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the binding molecule may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the binding molecule light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In one embodiment, a binding molecule of the invention comprises or consists of an antigen binding fragment of an antibody. The term "antigen-binding fragment" refers to a polypeptide fragment of an immunoglobulin or antibody that binds antigen or competes with intact antibody (i.e., with the intact antibody from which they were derived) for antigen binding (i.e., specific binding). As used herein, the term "fragment" of an antibody molecule includes antigen-binding fragments of antibodies, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

In one embodiment, a binding molecule of the invention is an engineered or modified antibody. Engineered forms of antibodies include, for example, minibodies, diabodies, diabodies fused to CH3 molecules, tetravalent antibodies, intra-diabodies (e.g., Jendreyko et al. 2003. J. Biol. Chem. 278: 47813), bispecific antibodies, fusion proteins (e.g., antibody cytokine fusion proteins) or, bispecific antibodies. Other immunoglobulins (Ig) and certain variants thereof are described, for example in U.S. Pat. No. 4,745,055; EP 256, 654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In one embodiment, the modified antibodies of the invention are minibodies. Minibodies are dimeric molecules made up of two polypeptide chains each comprising an ScFv molecule (a single polypeptide comprising one or more antigen binding sites, e.g., a VL domain linked by a flexible linker to a VH domain fused to a CH3 domain via a connecting peptide.

ScFv molecules can be constructed in a VH-linker-VL orientation or VL-linker-VH orientation.

The flexible hinge that links the VL and VH domains that make up the antigen binding site preferably comprises from about 10 to about 50 amino acid residues. An exemplary connecting peptide for this purpose is (Gly4Ser)$_3$ (SEQ ID NO:17) (Huston et al. 1988. Proc. Natl. Acad. Sci. USA 85:5879). Other connecting peptides are known in the art.

Methods of making single chain antibodies are well known in the art, e.g., Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

Minibodies can be made by constructing an ScFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

Diabodies are similar to scFv molecules, but usually have a short (less than 10 and preferably 1-5) amino acid residue linker connecting both V-domains, such that the VL and VH domains on the same polypeptide chain can not interact. Instead, the VL and VH domain of one polypeptide chain interact with the VH and VL domain (respectively) on a second polypeptide chain (WO 02/02781). In one embodiment, a binding molecule of the invention is a diabody fused to at least one heavy chain portion. In a preferred embodiment, a binding molecule of the invention is a diabody fused to a CH3 domain.

Other forms of modified antibodies are also within the scope of the instant invention (e.g., WO 02/02781 A1; 5,959, 083; 6,476,198 B1; US 2002/0103345 A1; WO 00/06605; Byrn et al. 1990. Nature. 344:667-70; Chamow and Ashkenazi. 1996. Trends Biotechnol. 14:52).

In one embodiment, a binding molecule of the invention comprises an immunoglobulin constant region. It is known in the art that the constant region mediates several effector functions. For example, binding of the C1 component of complement to binding molecules activates the complement system. Activation of complement is important in the opsonisation and lysis of cell pathogens. The activation of complement also stimulates the inflammatory response and may also be involved in autoimmune hypersensitivity. Further, binding molecules bind to cells via the Fc region, with a Fc receptor site on the binding molecule Fc region binding to a Fc receptor (FcR) on a cell. There are a number of Fc receptors which are specific for different classes of binding molecule, including IgG (gamma receptors), IgE (epsilon receptors), IgA (alpha receptors) and IgM (mu receptors). Binding of binding molecule to Fc receptors on cell surfaces triggers a number of important and diverse biological responses including engulfment and destruction of binding molecule-coated particles, clearance of immune complexes, lysis of binding molecule-coated target cells by killer cells (called antibody-dependent cell-mediated cytotoxicity, or ADCC), release of inflammatory mediators, placental transfer and control of immunoglobulin production.

In one embodiment, effector functions may be eliminated or reduced by using a constant region of an IgG4 binding molecule, which is thought to be unable to deplete target cells, or making Fc variants, wherein residues in the Fc region critical for effector function(s) are mutated using techniques known in the art, for example, U.S. Pat. No. 5,585,097. For example, the deletion or inactivation (through point mutations or other means) of a constant region domain may reduce Fc receptor binding of the circulating modified binding molecule thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or binding molecule flexibility. More generally, those skilled in the art will realize that binding molecules modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, a binding molecule of the invention can be derivatized or linked to another functional molecule (e.g., another peptide or protein). Accordingly, a binding molecule of the invention include derivatized and otherwise modified forms of the anti-GITR binding molecules described herein, including immunoadhesion molecules. For example, a binding molecule of the invention can be functionally linked (by chemical coupling, genetic fusion, noncovalent association or otherwise) to one or more other molecular entities, such as another binding molecule (e.g., a bispecific antibody or a diabody), a detectable agent, a cytotoxic agent, a pharmaceutical agent, and/or a protein or peptide that can mediate association of the binding molecule with another molecule (such as a streptavidin core region or a polyhistidine tag).

One type of derivatized binding molecule is produced by crosslinking two or more binding molecules (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a binding molecule of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. A binding molecule may also be derivatized with detectable enzymes, such as alkaline phosphatase, horseradish peroxidase, glucose oxidase and the like. When a binding molecule is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding molecule may also be derivatized with biotin, and detected through indirect measurement of avidin or streptavidin binding.

IV. Expression of Binding Molecules

A binding molecule of the invention can be prepared by recombinant expression of immunoglobulin light and heavy chain genes in a host cell. To express a binding molecule recombinantly, a host cell is transfected with one or more recombinant expression vectors carrying DNA fragments encoding the immunoglobulin light and heavy chains of the binding molecule such that the light and heavy chains are expressed in the host cell and, preferably, secreted into the medium in which the host cells are cultured, from which medium a binding molecule can be recovered. Standard recombinant DNA methodologies are used to obtain antibody heavy and light chain genes, incorporate these genes into recombinant expression vectors, and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss, et al.

To express a binding molecule of the invention, DNAs encoding partial or full-length light and heavy chains may be inserted into expression vectors such that the genes are operatively linked to transcriptional and translational control sequences. In this context, the term "operatively linked" means that a binding molecule gene is ligated into a vector such that transcriptional and translational control sequences within the vector serve their intended function of regulating the transcription and translation of the binding molecule gene. In one embodiment, the expression vector and expression control sequences are chosen to be compatible with the expression host cell used. The binding molecule light chain gene and the binding molecule heavy chain gene may be inserted into separate vector or, more typically, both genes are inserted into the same expression vector. The binding molecule genes may be inserted into the expression vector by standard methods (e.g., ligation of complementary restriction sites on the binding molecule gene fragment and vector, or blunt end ligation if no restriction sites are present). Prior to insertion of the binding molecule light or heavy chain sequences, the expression vector may already carry binding molecule constant region sequences. For example, one approach to converting VH and VL sequences to full-length binding molecule genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the binding molecule chain from a host cell. The binding molecule chain gene can be cloned into the vector such that the signal peptide is linked in-frame to the amino terminus of the binding molecule chain gene. The signal peptide can be an immunoglobulin signal peptide or a heterologous signal peptide (i.e., a signal peptide from a non-immunoglobulin protein).

In addition to the binding molecule chain genes, the recombinant expression vectors of the invention carry regulatory sequences that control the expression of the binding molecule chain genes in a host cell. The term "regulatory sequence" includes promoters, enhancers and other expression control elements (e.g., polyadenylation signals) that control the transcription or translation of the binding molecule chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner, et al.

In addition to the binding molecule chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the binding molecule heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express a binding molecule of the invention in either prokaryotic or eukaryotic host cells, expression of binding molecules in eukaryotic cells, and most preferably mammalian host cells, is the most preferred because such eukaryotic cells, and in particular mammalian cells, are more likely than prokaryotic cells to assemble and secrete a properly folded and immunologically active binding molecule.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding binding molecules). See Winnacker, From Genes to Clones, VCH Publishers, N.Y., N.Y. (1987). Eukaryotic cells are actually preferred, because a number of suitable host cell lines capable of secreting heterologous proteins (e.g., intact binding molecules) have been developed in the art, and include CHO cell lines, various Cos cell lines, HeLa cells, myeloma cell lines, or transformed B-cells or hybridomas. Preferably, the cells are nonhuman. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149(1992).

Alternatively, binding molecule-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Preferred mammalian host cells for expressing the recombinant binding molecules of the invention include Chinese Hamster Ovary (CHO cells) (including dhfr- CHO cells, described in Urlaub and Chasin, (1980) *Proc. Natl. Acad. Sci. USA* 77:4216-4220, used with a DHFR selectable marker, e.g., as described in R. J. Kaufman and P.A. Sharp (1982) *Mol. Biol.* 159:601-621), NS0 myeloma cells, COS cells and SP2 cells. When recombinant expression vectors encoding binding molecule genes are introduced into mammalian host cells, binding molecules are produced by culturing the host cells for a period of time sufficient to allow for expression of the binding molecule in the host cells or, more preferably, secretion of the binding molecule into the culture medium in which the host cells are grown. Binding molecules can be recovered from the culture medium using standard protein purification methods.

The vectors containing the polynucleotide sequences of interest (e.g., the binding molecule heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole binding molecules, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure binding molecules of at least about 90 to 95% homogeneity are preferred, and 98 to 99% or more homogeneity most preferred, for pharmaceutical uses.

Host cells can also be used to produce portions of intact binding molecules, such as Fab fragments or scFv molecules.

It will be understood that variations on the above procedure are within the scope of the present invention. For example, it may be desirable to transfect a host cell with DNA encoding either the light chain or the heavy chain (but not both) of a binding molecule of this invention. Recombinant DNA technology may also be used to remove some or all of the DNA encoding either or both of the light and heavy chains that is not necessary for binding to GITR. The molecules expressed from such truncated DNA molecules are also encompassed by a binding molecule of the invention. In addition, bifunctional binding molecules may be produced in which one heavy and one light chain are a binding molecule of the invention and the other heavy and light chain are specific for an antigen other than GITR by crosslinking a binding molecule of the invention to a second binding molecule by standard chemical crosslinking methods.

In view of the foregoing, another aspect of the invention pertains to nucleic acid, vector and host cell compositions that can be used for recombinant expression of a binding molecule of the invention. The nucleotide sequence encoding the 6C8 light chain variable region is shown in FIG. 18 and SEQ ID NO.: 10. The CDR1 domain of the VL encompasses nucleotides 130-162 of SEQ ID NO: 10 (SEQ ID NO: 14), the CDR2 domain encompasses nucleotides 208-228 of SEQ ID NO: 10 (SEQ ID NO: 15) and the CDR3 domain encompasses nucleotides 325-351 of SEQ ID NO: 10 (SEQ ID NO: 16). The nucleotide sequence encoding the 6C8 heavy chain variable region is also shown in FIG. 18 and SEQ ID NO.: 9. The CDR1 domain of the VH encompasses nucleotides 133-168 of SEQ ID NO: 9 (SEQ ID NO: 11), the CDR2 domain encompasses nucleotides 211-258 of SEQ ID NO: 9 (SEQ ID NO: 12) and the CDR3 domain encompasses nucleotides 355-381 of SEQ ID NO: 9 (SEQ ID NO: 13). In one embodiment, the nucleotide sequence encoding CDR2 of the VH comprises SEQ ID NO: 12. In another embodiment, the nucleotide sequence encoding CDR2 of the VH comprises SEQ ID NO: 65 (CACATTTGGTGGGATGATGATAAG-TACTATCAACCATCCCTGAAGAGCCA). It will be appreciated by the skilled artisan that nucleotide sequences encoding 6C8-related binding molecules can be derived from the nucleotide sequences encoding the 6C8 VL and VH using the genetic code and standard molecular biology techniques.

In one embodiment, the invention provides isolated nucleic acid molecules encoding a polypeptide sequence comprising a 6C8 CDR, e.g., comprising an amino acid sequence selected from the group consisting of: SEQ ID NO: 3, SEQ ID NO: 4, SEQ ID NO:19, SEQ ID NO:5, SEQ ID NO: 6, SEQ ID NO: 7, SEQ ID NO: 8.

In still another embodiment, the invention provides an isolated nucleic acid molecule encoding a binding molecule light chain variable region comprising the amino acid sequence of SEQ ID NO: 2, although the skilled artisan will appreciate that due to the degeneracy of the genetic code, other nucleic acid molecules can encode the amino acid sequence of SEQ ID NO: 2. The nucleic acid molecule can encode only the VL or can also encode a binding molecule light chain constant region, operatively linked to the VL. In one embodiment, this nucleic acid molecule is in a recombinant expression vector.

In still another embodiment, the invention provides an isolated nucleic acid molecule encoding a binding molecule heavy chain variable region comprising the amino acid sequence of SEQ ID NO: 1, although the skilled artisan will appreciate that due to the degeneracy of the genetic code, other nucleic acid molecules can encode the amino acid sequence of SEQ ID NO: 1. In another embodiment, the invention provides an isolated nucleic acid molecule encoding a binding molecule heavy chain variable region comprising the amino acid sequence of SEQ ID NO: 66, although the skilled artisan will appreciate that due to the degeneracy of the genetic code, other nucleic acid molecules can encode the amino acid sequence of SEQ ID NO: 66. The nucleic acid molecule can encode only the VH or can also encode a heavy chain constant region, operatively linked to the VH. For example, the nucleic acid molecule can comprise an IgG1 or IgG2 constant region. In one embodiment, this nucleic acid molecule is in a recombinant expression vector.

The invention also provides recombinant expression vectors encoding a binding molecule heavy chain and/or a binding molecule light chain. For example, in one embodiment, the invention provides a recombinant expression vector encoding:

a) a binding molecule light chain having a variable region comprising the amino acid sequence of SEQ ID NO: 2; and b) a binding molecule heavy chain having a variable region comprising the amino acid sequence of SEQ ID NO: 1.

In another embodiment, the invention provides a recombinant expression vector encoding:

a) a binding molecule light chain having a variable region comprising the amino acid sequence of SEQ ID NO: 2; and b) a binding molecule heavy chain having a variable region comprising the amino acid sequence of SEQ ID NO: 66.

The invention also provides host cells into which one or more of the recombinant expression vectors of the invention have been introduced. Preferably, the host cell is a mammalian host cell.

Still further the invention provides a method of synthesizing a recombinant binding molecules of the invention by culturing a host cell of the invention in a suitable culture medium until a recombinant binding molecule of the invention is synthesized. The method may further comprise isolating the recombinant binding molecule from the culture medium.

V. Uses of Binding Molecules of the Invention

Given their ability to bind to GITR, the binding molecules of the invention may be used to detect GITR (e.g., in a biological sample, such as serum or plasma), using a conventional immunoassay, such as an enzyme linked immunosorbent assays (ELISA), a radioimmunoassay (RIA) or tissue immunohistochemistry. The invention provides a method for detecting hGITR in a biological sample comprising contacting a biological sample with a binding molecule of the invention and detecting either the binding molecule bound to hGITR or unbound binding molecule, to thereby detect hGITR in the biological sample. The method may be performed in vitro or in vivo. The binding molecule is directly or indirectly labeled with a detectable substance to facilitate detection of the bound or unbound binding molecule. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Alternative to labeling the binding molecule, hGITR can be assayed in biological fluids by a competition immunoassay utilizing GITR standards labeled with a detectable substance and an unlabeled anti-hGITR binding molecule. In this assay, the biological sample, the labeled GITR standards and the anti-hGITR binding molecule are combined and the amount of labeled GITR standard bound to the unlabeled binding molecule is determined. The amount of hGITR in the biological sample is inversely proportional to the amount of labeled GITR standard bound to the anti-hGITR binding molecule.

An anti-GITR binding molecule of the invention can also be used to detect GITRs in samples from species other than humans, in particular GITRs from primates (e.g., chimpanzee, baboon, marmoset, cynomolgus and rhesus).

In another embodiment, the invention provides a method for abrogating the suppression of T effector cells by T regulatory cells. Abrogation of suppression of T effector cells by T regulatory cells can be assayed, for example, by measuring the ability of the binding molecule to enhance T cell effector function in the presence of T regulatory cells, e.g., cytokine production, (e.g., IL-2 production) or cell proliferation (e.g., T helper cell proliferation), by, for example, measuring $^3$H-thymidine incorporation or by FACS analysis. For example, the response or activity of T effector cells will be low in the presence of T regulatory cells, but will increase with the addition of a GITR binding molecule even if T regulatory cells are present, i.e., a GITR binding molecules abrogates the suppression of T effector cells by T regulatory cells.

The binding molecules of the invention may also be used to attenuate the degradation of I-κB in cells. Attenuated degradation of I-κB in cells can be assayed, for example, by Western blotting and quantitating the amount of I-κB following treatment of cells with anti-GITR binding molecule.

Numerous disease or pathological conditions would benefit from enhancing the activity of T effector cells and/or downmodulating the activity of T regulatory cells, e.g., by abrogating the suppression of T effector cells by T regulatory cells. For example, immune effector cells often fail to react effectively with cancer cells. Accordingly, when an enhanced effector T cell or antibody response is desired, the methods of the invention can be used to treat a subject suffering from such a disorder. In one embodiment such methods comprise administering to the subject a binding molecule of the invention such that suppression of T effector cells by T regulatory cells is abrogated, thereby enhancing an immune response. Preferably, the subject is a human subject. Alternatively, the subject can be a mammal expressing a GITR with which a binding molecule of the invention cross-reacts. Still further, the subject can be a mammal into which GITR has been introduced (e.g., by administration of GITR or by expression of a GITR transgene). A binding molecule of the invention may be administered to a human subject for therapeutic or prophylactic purposes. For example, the subject may have been diagnosed as having the disease or disorder or may be predisposed or susceptible to the disease. Moreover, a binding molecule of the invention can be administered to a non-human mammal expressing a GITR molecule with which the binding molecule cross-reacts (e.g., a primate) for veterinary purposes or as an animal model of human disease. Regarding the latter, such animal models may be useful for evaluating the therapeutic and/or, prophylactic efficacy of binding molecules of the invention (e.g., testing of dosages and/or time courses of administration).

Exemplary uses of the binding molecules of the invention are discussed further below:

Immunostimulatory Compositions

As described in the appended examples, the binding molecules of the invention can be used as immunostimulatory compositions (or vaccines), e.g., in combination with an antigen, to promote an enhanced immune response to an antigen of interest, e.g., a protein antigen, in a subject. That is, the binding molecules of the invention can serve as adjuvants to enhance immune responses. For example, to stimulate an antibody or cellular immune response to an antigen of interest (e.g., for vaccination purposes), the antigen and a binding molecules of the invention can be coadministered (e.g., coadministered at the same time in the same or separate compositions, or sequentially in time) such that an enhanced immune response occurs. The antigen of interest and a binding molecule can be formulated together into a single pharmaceutical composition or in separate compositions. In one embodiment, the antigen of interest and the binding molecule are administered simultaneously to the subject. Alternatively, in certain situations it may be desirable to administer the antigen first and then the binding molecule or vice versa (for example, it may be beneficial to first administer the antigen alone to stimulate a response and then administer a binding molecule, alone or together with a boost of antigen). In preferred embodiments, a GITR binding molecule of the invention is administered at the time of priming with antigen, i.e., at the time of the first administration of antigen. For example, day −3, −2, −1, 0, +1, +2, +3. A particularly preferred day of administration of a GITR binding molecule of the invention is day −1 prior to administration of antigen.

An antigen of interest is, for example, one capable of providing protection in subject against challenge by an infectious agent from which the antigen was derived, or which is capable of affecting tumor growth and metastasis in a manner which is of benefit to a subject. Exemplary antigens of interest therefore include those derived from infectious agents, cancer cells, and the like, wherein an immune response directed against the antigen serves to prevent or treat disease caused by the agent. Such antigens include, but are not limited to, viral, bacterial, fungal or parasite proteins, glycoproteins, lipoproteins, glycolipids, and the like. Antigens of interest also include those which provide benefit to a subject which is at risk for acquiring or which is diagnosed as having a tumor and may include, e.g., tumor-related antigens expressed exclusively by or at increased levels by tumor cells. The subject is preferably a mammal and most preferably, is a human.

As used herein the term "pathogen" or "pathogenic agent" includes microorganisms that are capable of infecting or parasitizing normal hosts (e.g., animals (such as mammals, preferably primates, e.g. humans)). As used herein, the term also includes opportunistic agents, e.g., microorganisms that are capable of infecting or parasitizing abnormal hosts, e.g., hosts in which normal flora have been supplanted, e.g., as a result of a treatment regimen, or immunocompromised hosts. As used herein the term also includes microorganisms whose replication is unwanted in a subject or toxic molecules (e.g., toxins) produced by microorganisms.

Non-limiting examples of viral antigens include, but are not limited to, the nucleoprotein (NP) of influenza virus and the Gag proteins of HIV. Other heterologous antigens include, but are not limited to, HIV Env protein or its component parts, gp120 and gp41, HIV Nef protein, and the HIV Pol proteins, reverse transcriptase and protease. In addition, other viral antigens such as Ebola virus (EBOV) antigens, such as, for example, EBOV NP or glycoprotein (GP), either full-length or GP deleted in the mucin region of the molecule (Yang Z-Y, et al. (2000) *Nat Med* 6:886-9, 2000), small pox antigens, hepatitis A, B or C virus, human rhinovirus such as type 2 or type 14, Herpes simplex virus, poliovirus type 2 or 3, foot-and-mouth disease virus (FMDV), rabies virus, rotavirus, influenza virus, coxsackie virus, human papilloma virus (HPV), for example the type 16 papilloma virus, the E7 protein thereof, and fragments containing the E7 protein or its epitopes; and simian immunodeficiency virus (SIV) may be used. The antigens of interest need not be limited to antigens of viral origin. Parasitic antigens, such as, for example, malarial antigens are included, as are fungal antigens, bacterial antigens and tumor antigens can also be used in connection with the disclosed compositions and methods. Non-limiting examples of bacterial antigens include: *Bordetella pertussis* (e.g., P69 protein and filamentous haemagglutinin (FHA) antigens), *Vibrio cholerae, Bacillus anthracis*, and *E. coli* antigens such as *E. coli* heat Labile toxin B subunit (LT-B), *E. coli* K88 antigens, and enterotoxigenic *E. coli* antigens. Other examples of antigens include *Schistosoma mansoni* P28 glutathione S-transferase antigens (P28 antigens) and antigens of flukes, mycoplasma, roundworms, tapeworms, *Chlamydia trachomatis*, and malaria parasites, e.g., parasites of the genus *plasmodium* or *babesia*, for example *Plasmodium falciparum*, and peptides encoding immunogenic epitopes from the aforementioned antigens.

An infection, disease or disorder which may be treated or prevented by the administration of a vaccine of the invention includes any infection, disease or disorder wherein a host immune response acts to prevent the infection, disease or disorder. Diseases, disorders, or infection which may be treated or prevented by the administration of the immunostimulatory compositions of the invention include, but are not limited to, any infection, disease or disorder caused by or related to a fungus, parasite, virus, or bacteria, diseases, disorders or infections caused by or related to various agents used in bioterrorism, listeriosis, Ebola virus, SARS, small pox, hepatitis A, hepatitis B, hepatitis C, and hepatitis E, diseases and disorders caused by human rhinovirus, HIV (e.g., HIV-1 and HIV-2), and AIDS, Herpes, polio, foot-and-mouth disease, rabies, diseases or disorders caused by or related to: rotavirus, influenza, coxsackie virus, human papilloma virus, SIV, malaria, cancer, e.g., tumors, human herpes viruses, cytomegalovirus (esp. Human), Epstein-Barr virus, Varicella Zoster Virus, hepatitis viruses, such as hepatitis B virus, hepatitis A virus, hepatitis C virus a, paramyxoviruses: Respiratory Syncytial virus, parainfluenza virus, measles virus, mumps virus, human papilloma viruses (for example HPV6, 11, 16, 18, and the like), flaviviruses (e.g. Yellow Fever Virus, Dengue Virus, Tick-borne encephalitis virus, Japanese Encephalitis Virus), or influenza virus, e.g., influenza A (e.g., subtypes, hemagglutinin (H) and neuraminidase (N)), influenza B, and influenza C, and diseases or disorders caused by or related to infection by bacterial organisms, including gram-positive and gram-negative bacteria. Examples include, but are not limited to, *Neisseria* spp, including *N. gonorrhea* and *N. meningitidis, Streptococcus* spp, including *S. pneumoniae, S. pyogenes, S. agalactiae, S. mutans; Haemophilus* spp, including *H. influenzae* type B, non typeable *H. influenzae, H. ducreyi; Moraxella* spp, including M catarrhalis, also known as Branhamella catarrhalis; *Bordetella* spp, including *B. pertussis, B. parapertussis* and *B. bronchiseptica; Mycobacterium* spp., including *M. tuberculosis, M. bovis, M leprae, M avium, M paratuberculosis, M smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae*, S. flexnerii; *Yersinia* spp, including Y enterocolitica, *Y. pestis*, Y pseudotuberculosis, *Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including *H. pylori; Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic *Ehrlichiosis; Rickettsia* spp, including *R. rickettsii; Chlamydia* spp., including *C. trachomatis, C. neumoniae, C. psittaci; Leptospira* spp., including L. interrogans; *Treponema* spp., including *T pallidum, T denticola, T hyodysenteriae*. Preferred bacteria include, but are not limited to, Listeria, mycobacteria, mycobacteria (e.g., tuberculosis), Anthrax, *Salmonella* and *Listeria monocytogenes*, *Bordetella pertussis*, *Vibrio cholerae*, flukes, mycoplasma, roundworms, tapeworms, *Chlamydia trachomatis*, and *malaria parasites.*

As used herein, the term "bacterial infections" include infections with a variety of In another embodiment, T cells can be removed from a patient, and contacted in vitro with an anti-GITR binding molecule, optionally with an activating signal (e.g., antigen plus APCs or a polyclonal antibody) and reintroduced into the patient.

Regulatory T cells play an important role in the maintenance of immunological self-tolerance by suppressing immune responses against autoimmune diseases and cancer. Accordingly, in one embodiment, abrogating the suppression of T effector cells by T regulatory cells would be beneficial for enhancing an immune response in cancer. Therefore, the binding molecules of the invention can be used in the treatment of malignancies, to inhibit tumor growth or metastasis. The binding molecules may be administered systemically or locally to the tumor site.

In one embodiment, modulation of GITR function may be useful in the induction of tumor immunity, i.e., for the treatment of a subject with a neoplastic disease or cancer. In one embodiment, a binding molecule of the invention reduces tumor size, inhibits tumor growth and/or prolongs the survival time of a tumor-bearing subject. A GITR binding molecule can be administered to a patient having tumor cells (e.g., sarcoma, melanoma, lymphoma, leukemia, neuroblastoma, carcinoma) to overcome tumor-specific tolerance in the subject.

By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens include any known or heretofore unknown tumor antigen, including, without limitation, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer.

As used herein, the term "neoplastic disease" is characterized by malignant tumor growth or in disease states characterized by benign hyperproliferative and hyperplastic cells. The common medical meaning of the term "neoplasia" refers to "new cell growth" that results as a loss of responsiveness to normal growth controls, e.g., neoplastic cell growth.

As used herein, the terms "hyperproliferative", "hyperplastic", malignant" and "neoplastic" are used interchangeably, and refer to those cells in an abnormal state or condition characterized by rapid proliferation or neoplasia. The terms are meant to include all types of hyperproliferative growth, hyperplastic growth, cancerous growths or oncogenic processes, metastatic tissues or malignantly transformed cells, tissues, or organs, irrespective of histopathologic type or stage of invasiveness. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be either benign, premalignant or malignant.

The terms "neoplasia," "hyperplasia," and "tumor" are often commonly referred to as "cancer," which is a general name for more than 100 disease that are characterized by uncontrolled, abnormal growth of cells. Examples of cancer include, but are not limited to: breast; colon; non-small cell lung, head and neck; colorectal; lung; prostate; ovary; renal; melanoma; and gastrointestinal (e.g., pancreatic and stomach) cancer; and osteogenic sarcoma.

In one embodiment, the cancer is selected from the group consisting of: pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues.

Accordingly, this invention also relates to a method of treating neoplastic disease or cancer in a subject, preferably a human, or other animal by administering to such subject or animal an effective amount of a binding molecule of the invention. One skilled in the art is able, by routine experimentation, to determine what an effective amount of polypeptide would be for the purpose of treating neoplastic disease or cancer. For example, a therapeutically effective amount of a binding molecule of the invention may vary according to factors such as the disease stage (e.g., stage I versus stage IV), age, sex, medical complications (e.g., immunosuppressed conditions or diseases) and weight of the subject, and the ability of the binding molecule to elicit a desired response in the subject. The dosage regimen may be adjusted to provide the optimum therapeutic and/or prophylactic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

Methods of Enhancing Immune Responses

The subject binding molecules may also be used in methods of enhancing immune responses. Upregulation of immune responses may be in the form of enhancing an existing immune response or eliciting an initial immune response. For example, enhancing an immune response by modulation of GITR may be useful in cases of viral infection. As anti-GITR binding molecules act to enhance immune responses, they would be therapeutically useful in situations where more rapid or thorough clearance of pathogenic agents, e.g., bacteria and viruses would be beneficial. Accordingly, the anti-GITR binding molecules of the invention may be used therapeutically, either or alone or in combination with an antigen or an additional immunostimulatory agent, to treat a subject suffering from a disease or disorder, such as an infectious disease or malignancy, e.g., those listed supra.

Anti-GITR binding molecules may also be used prophylactically in vaccines against various pathogens. Immunity against a pathogen, e.g., a virus, could be induced by vaccinating with a viral protein along with a GITR binding molecule (as described above). Alternately, an expression vector which encodes genes for both a pathogenic antigen and a GITR binding molecule, e.g., a vaccinia virus expression vector engineered to express a nucleic acid encoding a viral protein and a nucleic acid encoding a GITR binding molecule, can be used for vaccination. Pathogens for which vaccines may be useful include, for example, hepatitis B, hepatitis C, Epstein-Barr virus, cytomegalovirus, HIV-1, HIV-2, influenza, tuberculosis, malaria and schistosomiasis.

The present invention is further directed to binding molecule-based therapies which involve administering binding molecules of the invention to an animal, preferably a mammal, and most preferably a human, patient for treating, detecting, and/or preventing one or more of the disclosed diseases, disorders, or conditions. Therapeutic compounds of the invention include, but are not limited to, binding molecules of the invention (including analogs and derivatives thereof as described herein) and anti-idiotypic binding molecules as described herein. A binding molecule of the invention can be used to treat, diagnose, inhibit or prevent diseases, disorders or conditions associated with aberrant activity of GITR, including, but not limited to, any one or more of the diseases, disorders, or conditions described herein (e.g., binding molecules of the invention may be provided in pharmaceutically acceptable compositions as known in the art or as described herein.

A binding molecule of this invention may be advantageously utilized in combination with other monoclonal or chimeric binding molecules, or with lymphokines or hematopoietic growth factors (such as, e.g., IL-2, IL-3 and IL-7), for example, which serve to increase the number or activity of effector cells which interact with a binding molecule.

A binding molecule of the invention may be administered alone or in combination with other types of treatments (e.g., radiation therapy, chemotherapy, hormonal therapy, immunotherapy and anti-tumor agents, antibiotics, therapy directed against a pathogenic agent (such as for example an immunotherapeutic or chemotherapeutic agent effective against a viral pathogen or a bacterial antigen) and immunostimulatory agents. A binding molecule of the invention may also be administered in combination with an antigen to which an enhanced immune response is desired, e.g., a vaccine or an antigen from a pathogenic agent (or an attenuated form of a virus or bacterium) or an antigen from a tumor as described above. In one embodiment, a binding molecule of the invention is administered alone or in a combination therapy to a subject with an infection. In another embodiment, a binding molecule of the invention is administered alone or in combination to a subject with a chronic viral infection. In yet another embodiment, a binding molecule of the invention are administered alone or in combination to a subject with cancer.

Generally, administration of binding molecules derived a species that is the same species as that of the patient is preferred. Thus, in a preferred embodiment, human binding molecules, derivatives, analogs, or nucleic acids, are administered to a human patient for therapy or prophylaxis.

VI. Pharmaceutical Compositions

A binding molecule of the invention can be incorporated into pharmaceutical compositions suitable for administration to a subject. Typically, the pharmaceutical composition comprises a binding molecule of the invention and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacturer and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, a binding molecule of the invention is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical compositions can be included in a container, pack, or dispenser together with instructions for administration.

VII. Administration of Binding Molecules of the Invention

Binding molecules of the invention are contacted with cells from a subject in a biologically compatible form in vitro or in vivo. By "biologically compatible form" is meant a form of the agent to be administered in which any toxic effects are outweighed by the therapeutic effects of the binding molecule.

In one embodiment, the subject compositions are administered to a subject. Administration of a therapeutically active amount of the therapeutic compositions of the present invention is defined as an amount effective, at dosages and for periods of time necessary to achieve the desired result. For example, a therapeutically active amount of binding molecule may vary according to factors such as the disease state, age, sex, and weight of the individual, and the ability of the binding molecule to elicit a desired response in the individual. Dosage regimens can be adjusted to provide the optimum therapeutic response. For example, several divided doses can be administered daily or the dose can be proportionally reduced as indicated by the exigencies of the therapeutic situation.

The pharmaceutical compositions of the invention may include a "therapeutically effective amount" or a "prophylactically effective amount" of a binding molecule of the invention. A "therapeutically effective amount" refers to an amount effective, at dosages and for periods of time necessary, to achieve the desired therapeutic result. A therapeutically effective amount of the binding molecule may vary according to factors such as the disease state, age, sex, and weight of the individual, and the ability of the binding molecule to elicit a desired response in the individual. A therapeutically effective amount is also one in which any toxic or detrimental effects of the binding molecule are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a binding molecule of the invention is, e.g., from about 0.1-25 mg/kg, from about 1.0-10 mg/kg, from about 0.5-2.5 mg/kg, from about 5-25 mg/kg, from about 1-400 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Additional, non-limiting ranges for a therapeutically or prophylactically effective amount of a binding molecule of the invention is from about 0.0001 to 100 mg/kg, and from about 0.01 to 5 mg/kg (e.g., 0.02 mg/kg, 0.25 mg/kg, 0.5 mg/kg, 0.75 mg/kg, 1 mg/kg, 2 mg/kg, etc.), of the subject body weight. For example, dosages can be 1 mg/kg body weight or 10 mg/kg body weight or within the range of 1-10 mg/kg, preferably at least 1 mg/kg. Doses intermediate in the above ranges are also intended to be within the scope of the invention.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly.

Binding molecules of the invention can be administered on multiple occasions. Intervals between single dosages can be, e.g., daily, weekly, monthly or yearly. Intervals can also be irregular as indicated by measuring blood levels of binding molecule in the patient.

Binding molecules of the invention can optionally be administered in combination with other agents that are effective in treating the disorder or condition in need of treatment (e.g., prophylactic or therapeutic). Preferred additional agents are those which are art recognized and are standardly administered for a particular disorder.

The binding molecule can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, to administer the agent by other than parenteral administration, it may be desirable to coat, or co-administer the agent with, a material to prevent its inactivation.

A binding molecule of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, a binding molecule of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Binding molecules can be co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) J. Neuroimmunol. 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

When the active compound is suitably protected, as described above, the binding molecule can be orally administered, for example, with an inert diluent or an assimilable edible carrier.

Supplementary active compounds can also be incorporated into the compositions. In certain embodiments, a binding molecule of the invention is coformulated with and/or coadministered with one or more additional therapeutic agents. For example, an anti-GITR binding molecule of the invention may be coformulated and/or coadministered with one or more additional antibodies that bind other targets e.g., antibodies that bind other cytokines or that bind cell surface molecules. Such combination therapies may advantageously utilize lower dosages of the administered therapeutic agents, thus avoiding possible toxicities or complications associated with the various monotherapies.

The present invention further encompasses binding molecules conjugated to a diagnostic or therapeutic agent. A binding molecule can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the binding molecule or indirectly, through an intermediate (such as, for example, a linker known in the art) using techniques known in the art. See, for example, U.S. Pat. No. 4,741,900 for metal ions which can be conjugated to binding molecules for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material $I^{125}$ $I^{131}$, $I^{111}$, $In^{99\ Tc}$.

Further, a binding molecule may be conjugated to a therapeutic moiety such as a cytotoxin, e.g., a cytostatic or cytocidal agent, a therapeutic agent, a radioactive metal ion, e.g., alpha-emitters such as, for example, $^{213}Bi$, biological toxins, prodrugs, peptides, proteins, enzymes, viruses, lipids, biological response modifiers, pharmaceutical agents, immunologically active ligands (e.g., lymphokines or other antibodies). In another embodiment, a binding molecule of the invention can be conjugated to a molecule that decreases vascularization of tumors. In other embodiments, the disclosed compositions may comprise binding molecules of the invention coupled to drugs or prodrugs. Still other embodiments of the present invention comprise the use of binding molecules of the invention conjugated to specific biotoxins or their cytotoxic fragments such as ricin, gelonin, pseudomonas exotoxin or diphtheria toxin. The selection of which conjugated or unconjugated binding molecule to use will depend on the type and stage of cancer, use of adjunct treatment (e.g., chemotherapy or external radiation) and patient condition. It will be appreciated that one skilled in the art could readily make such a selection in view of the teachings herein.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, camustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

This invention is further illustrated by the following examples, which should not be construed as limiting. The contents of all references, patents and published patent applications cited throughout this application, as well as the Figures, are incorporated herein by reference.

EXAMPLES

The following materials and methods were used in certain Examples:

Methods

Culture of T Cell Lines

Differentiated cell lines were produced from cells prepared from human cord blood or peripheral blood CD4+ CD45RA+ naïve T cells by a variety of methods, including flow cytometry and magnetic bead separations. Purity of the starting populations was >95%. Cells were then stimulated by CD3 and CD28 antibodies in RPMI 1640 with 110% FCS and 1% Human AB serum with defined mixtures of cytokines and neutralizing antibodies to cytokines to produce the differentiated cell types. Th1 cells were produced by culture with IL12 (62 U/ml) and anti-IL4 (0.2 µg/ml); Th2 cells were produced by culture in IL4 (145 U/ml) and anti-IL12 (10 µg/ml) and anti-IFNγ (10 ug/ml); and regulatory T cells were produced by culture in TGFβ (32 U/ml), IL9 (42 U/ml), anti-IL4 (10 ug/ml) and anti-IL12 (10 ug/ml) and anti-IFNγ (10 ug/ml). (Note: anti-IL12 was not used in all experiments). All cultures were supplemented with IL2 (65 U/ml) and IL15 (4500 U/ml). Cells were split into larger culture dishes as warranted by cell division.

Example 1

Isolation and Purification of 6C8

Figure 2:
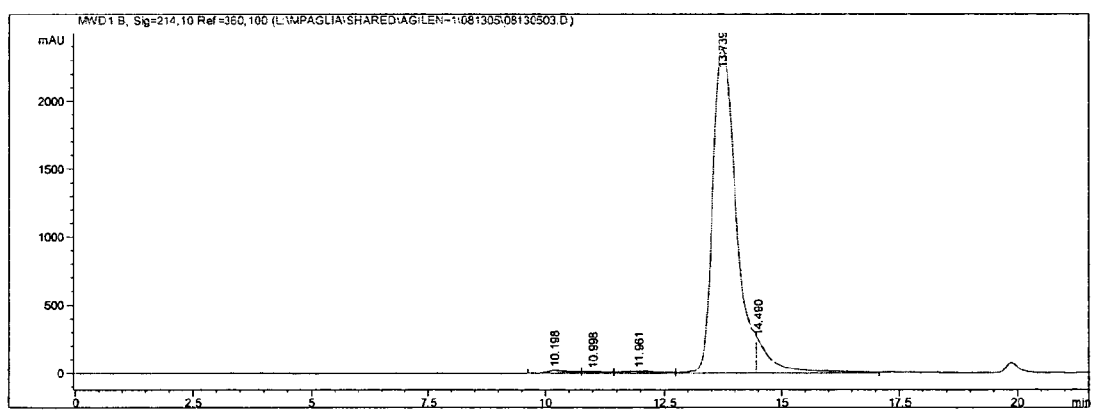
FIG. 2 depicts a size exclusion chromatography (SE-HPLC) of the purified human GITR binding molecule. Fifty micrograms of protein was injected onto the SE-HPLC column at a flow rate of 0.6 mmin. Purity of the binding molecules by SE-HPLC yielded a population of binding molecules in which 99.8% was in monomeric form and 0.2% aggregates.

The 6C8 antibody is an IgG2b, kappa. Purification of this antibody revealed the presence of a double heavy chain (FIG. 1). This could have been due to alternative glycosylation or contamination with another Ab. Size exclusion chromatography showed the presence of one peak (FIG. 2).

The 6C8 antibody was purified as follows:

1. Washed 20 ml Protein G (Pharmacia HR 10/30) with 5CV of dPBS
2. Loaded 1L (run 1) or 2 L (run 2) of hGITR (6C8) supernatant
3. Washed with 10 CV of dPBS
4. Eluted with 100 mM Citrate, pH 2.8 directly into 1 M Tris (20-25% v: v)
5. Stripped with 100 mM Citrate, pH 2.8, 0.3 M NaCl

Example 2

Characterization of 6C8

Figure 3:
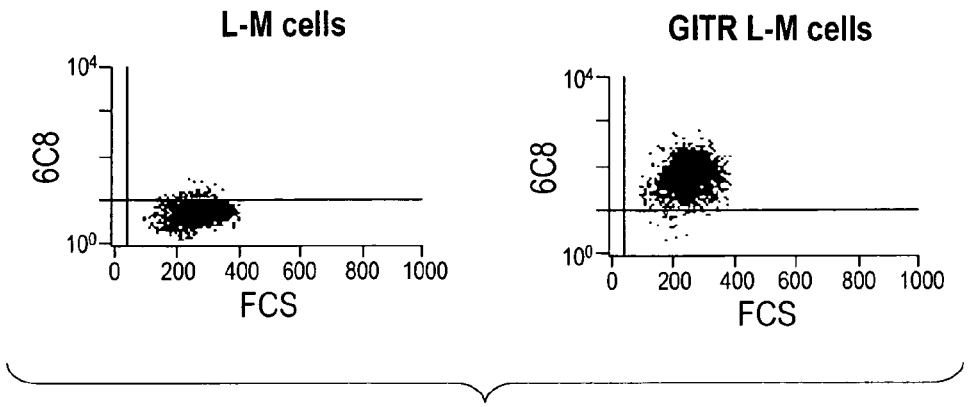
FIG. 3 depicts a FACS analysis of L-M (mouse fibroblast) cells transfected with the GITR gene that were stained with 50 µl of supernatant fluid from GITR-expressing hybridoma cells. The GITR binding molecule stained GITR-transfected cells but not the untransfected L-M cells.
Figure 4:
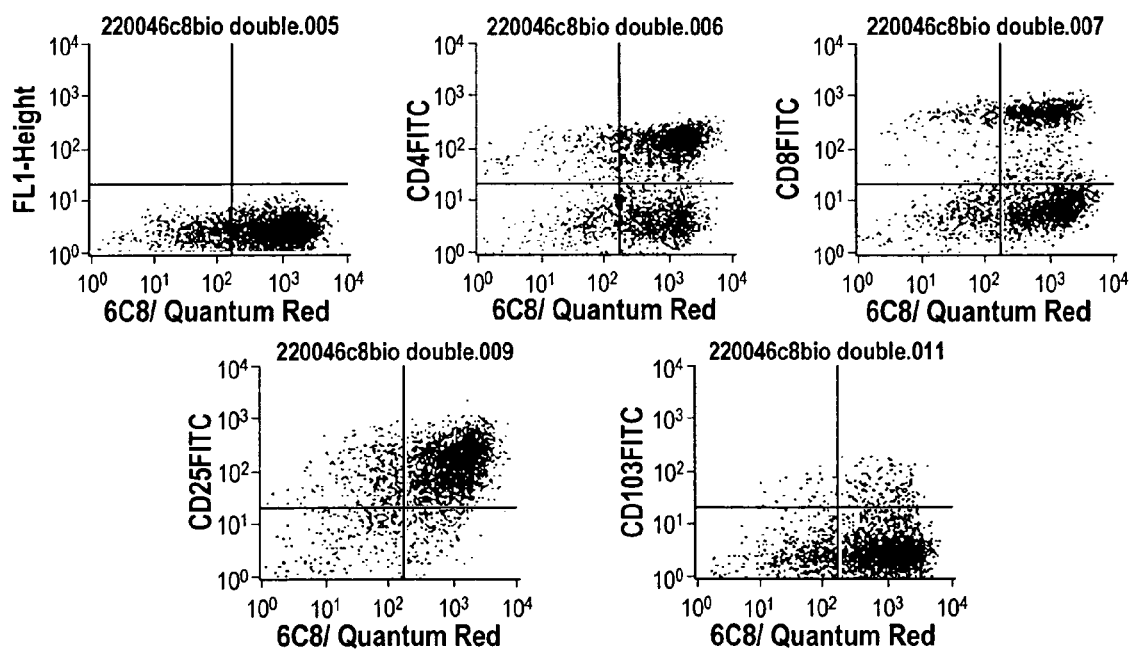
FIG. 4 depicts a FACS analysis demonstrating that GITR is primarily expressed on activated lymphocytes. The 6C8 binding molecules stains CD4+, CD8+, CD25+ lymphocytes and very weakly stains CD103+ cells.
Figure 5:
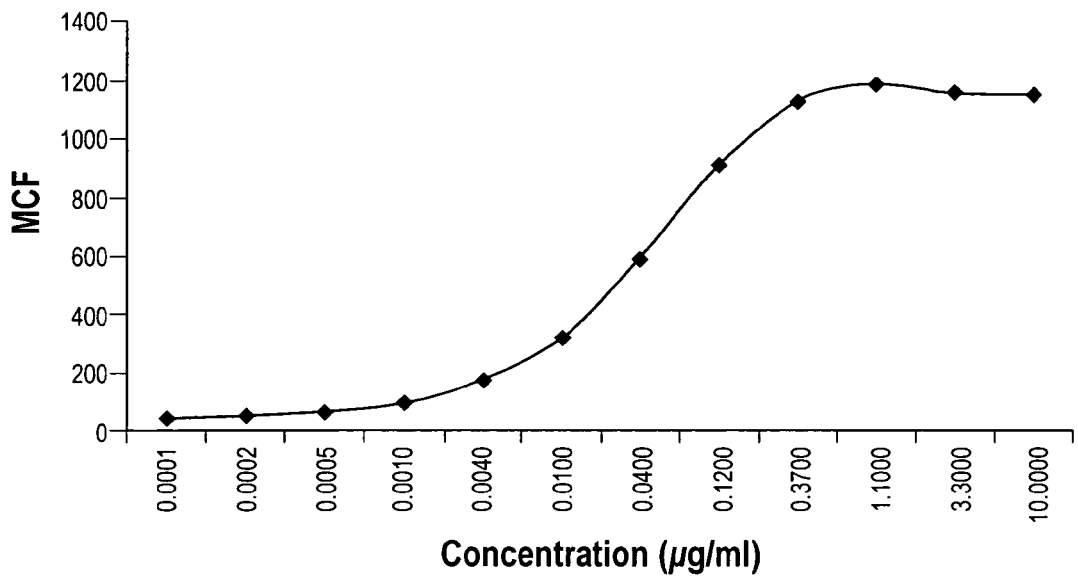
FIG. 5 depicts a saturation curve of the binding of the 6C8 binding molecule which was assessed by titrating biotin-labeled 6C8 on CD3-activated lymphocytes.

The 6C8 antibody binds to GITR-L-M transfected cells (FIG. 3) and activated PBLs (FIG. 4). The saturation curve of biotin-labeled anti-GITR on activated lymphocytes suggests a good relative affinity (FIG. 5).

Figure 6:
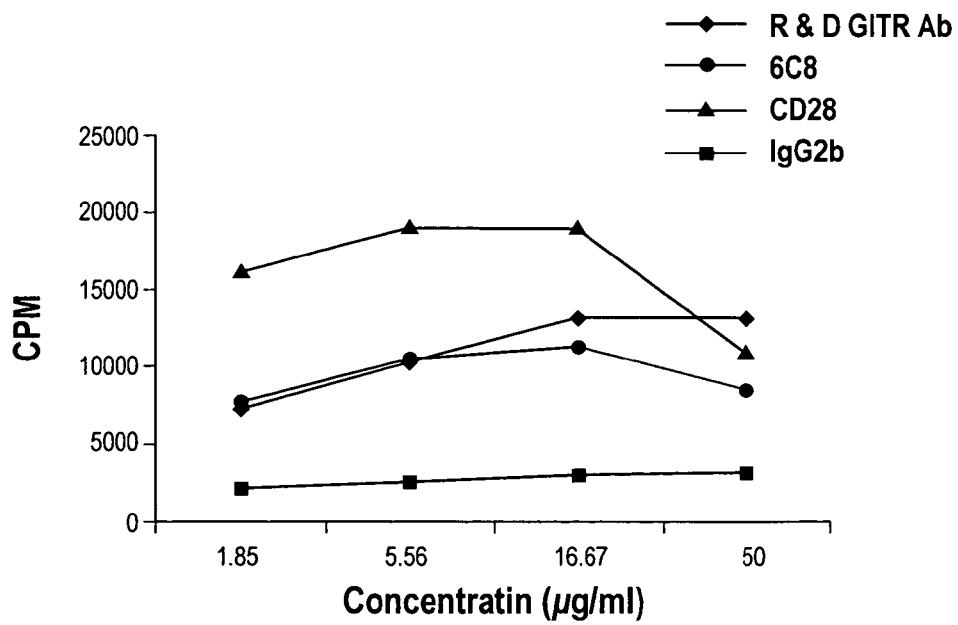
FIG. 6 is a graph showing that the 6C8 binding molecule is costimulatory to T lymphocytes which are stimulated with sub-optimal OKT3 (anti-CD3; 0.01 µg/ml) and incubated with either anti-CD28, or anti-GITR. An isotype control (IgG2b) was also used.

The 6C8 antibody is co-stimulatory on T lymphocytes activated with suboptimal anti-CD3 (FIG. 6). This antibody does not co-stimulate to the same level as CD28, but it is comparable to the commercial anti-GITR (R&D).

Figure 7A:
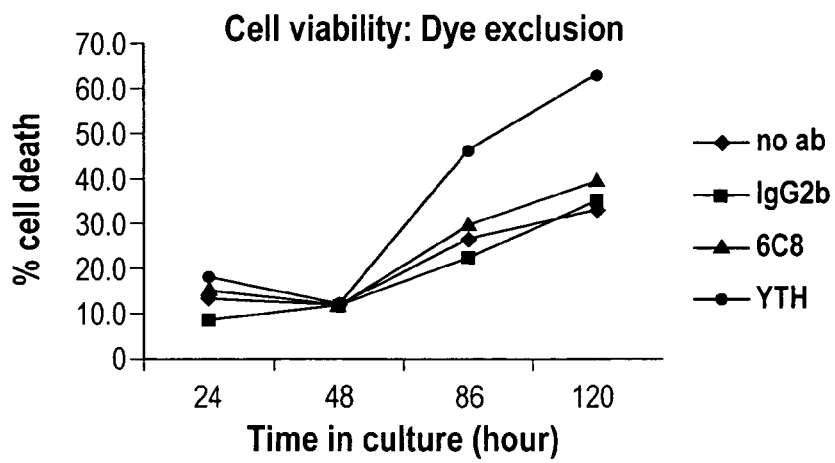
FIGS. 7A and 7B are graphs demonstrating that the 6C8 binding molecule does not induce apoptosis. Lymphocytes were activated with PHA for 3 days prior to the addition of 10 µg/ml of YTH655 (an anti-CD2 antibody known to induce apoptosis on activated lymphocytes; Friend, P., et al. (1987) *Transplant. Proc.* 19:4317), 6C8, or an isotype control (IgG2b). Apoptosis was measured by cell viability counts (A) and annexin V staining (B) and measuring apoptosis by flow cytometry.
Figure 7B:
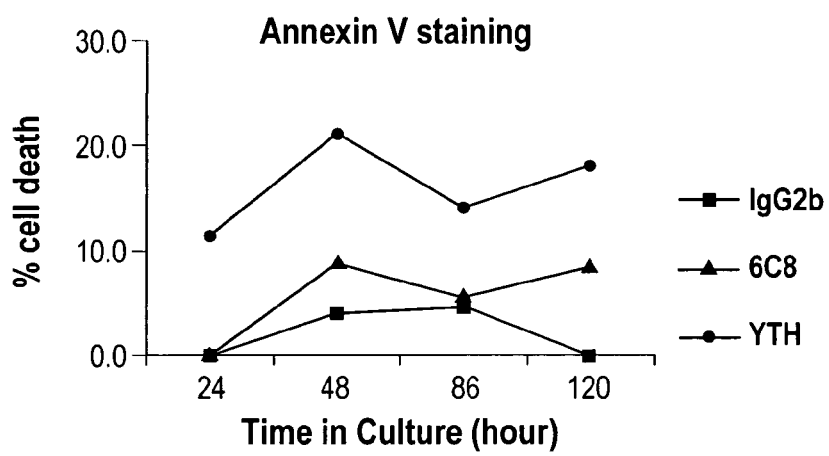

The 6C8 antibody does not induce apoptosis on activated lymphocytes (FIG. 7). Lymphocytes were activated with PHA for 3 days prior to the addition of the antibody. Compared to YTH 655 (anti-human CD2 known to induce apoptosis on activated lymphocytes) 6C8 does not increase the apoptosis of activated T lymphocytes.

Figure 8:
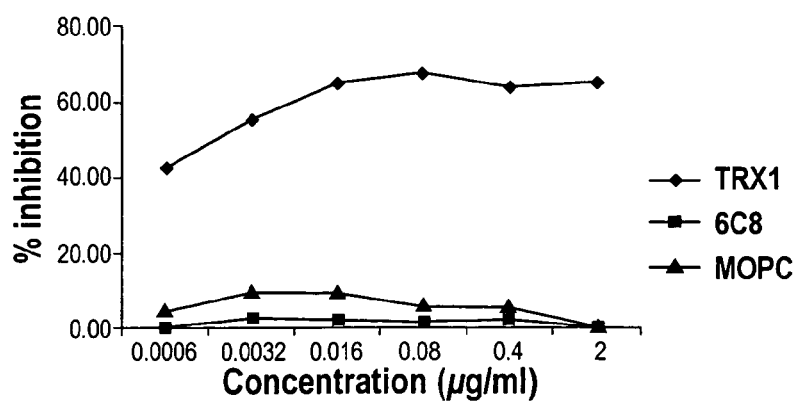
FIG. 8 is a graph demonstrating that the 6C8 binding molecule does not block a primary mixed lymphocyte reaction (MLR). Lymphocytes from allogenic donors were mixed in the presence of TRX1 (anti-human CD4), 6C8 or MOPC (an isotype control for TRX1) at various concentrations. The cells were incubated for 3 days and pulsed with $^3$H-thymidine 18 hours before the cells were harvested and counted.

The 6C8 antibody does not block a primary mixed lymphocyte reaction (MLR) (FIG. 8). TRX1 (anti-human CD4) was used as a positive control for the MLR.

Example 3

Figure 9:
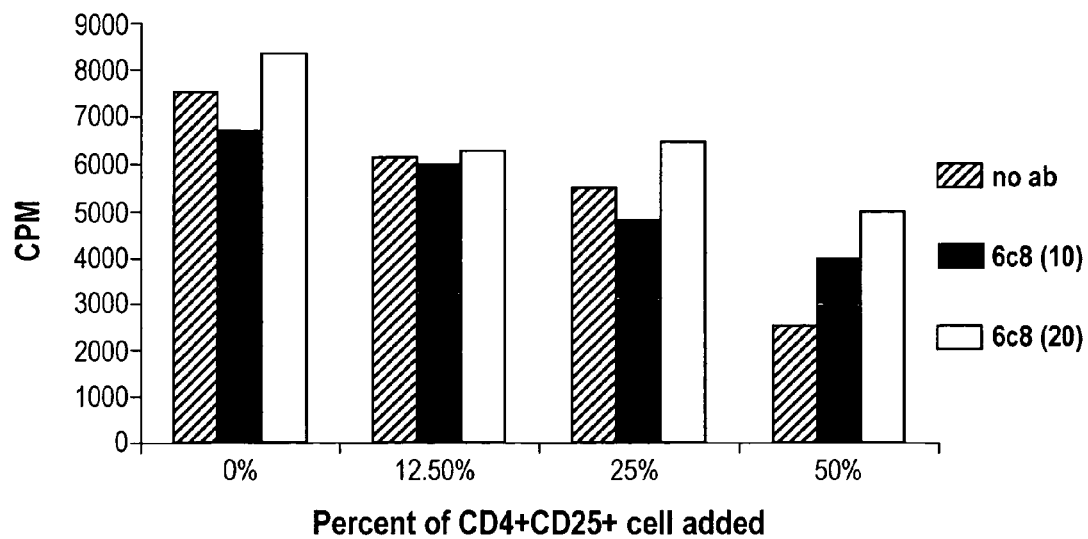
FIG. 9 is a graph demonstrating that the 6C8 binding molecule blocks the suppression of T effector cells induced by Treg cells. CD4+/CD25+ cells were added to CD4+/CD25- cells at various ratios. The cells were stimulated with plate-bound anti-CD3 and anti-CD28. At ratios of 1:1 there was inhibition of proliferation of the CD4+/CD25- cells. The addition of 6C8 at two different dilutions was able to block the suppression of CD4+ T effector cells induced by the CD4+/CD25+T regulatory cells.

The 6C8 Antibody Abrogates Suppression of T Effector Cells Induced by T Regulatory Cells The 6C8 antibody was able to block the suppression induced by T regulatory cells (FIG. 9). CD4+/CD25+ cells were added to CD4+/CD25− cells at various ratios. The cells were stimulated with plate-bound anti-CD3 and anti-CD28. At a ratio of 1:1 the CD4+/CD25+ cells were able to abrogate the proliferation of the CD4+/CD25−cells. The addition of 6C8 to the cultures was able to block the suppression in a dose-dependent manner.

Figure 10:
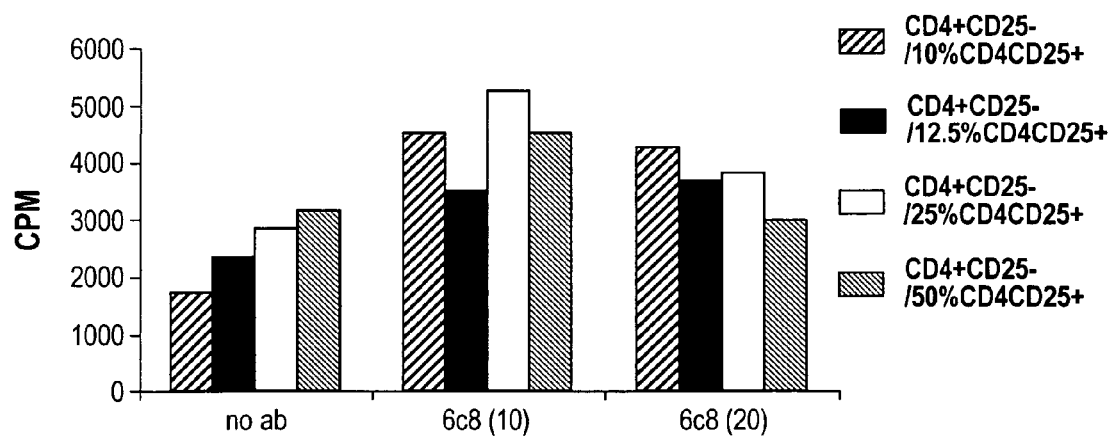
FIG. 10 is a graph demonstrating that the 6C8 binding molecule is co-stimulatory even when T cells are stimulated with anti-CD3 in the absence of anti-CD28. CD4+/CD25+ cells were incubated with CD4+/CD25- cells at different cell ratios. The cells were stimulated with plate-bound anti-CD3 only. 6C8 was added to the cells and under these conditions was co-stimulatory.

When T cells were stimulated through anti-CD3 only (with no co-stimulation with anti-CD28) there was no suppression observed with the addition of CD4+/CD25+ cells to the CD4+/CD25−cells, in fact, the anti-GITR antibody was slightly co-stimulatory under these conditions (FIG. 10).

Example 4

The 6C8 Antibody Modulates Signaling Via NF-kB

Figure 11:
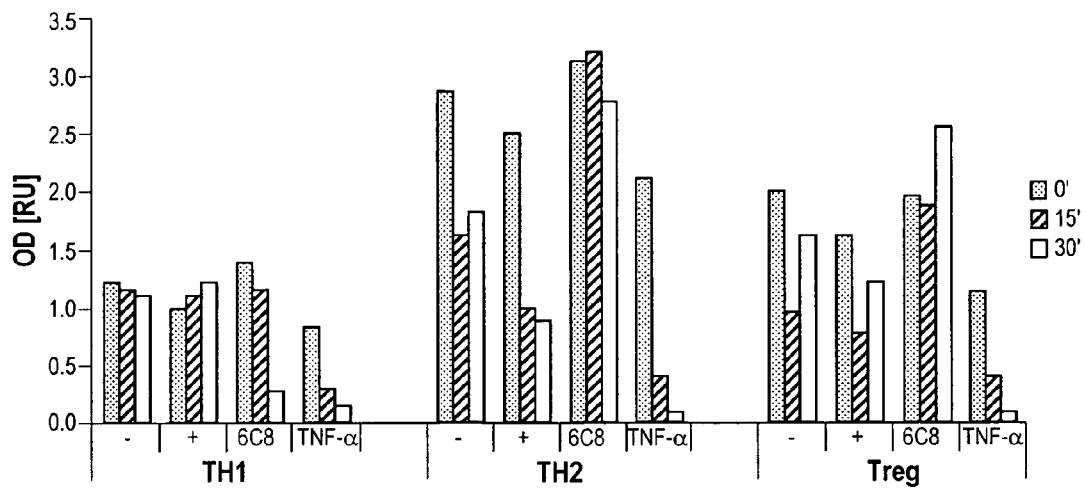
FIG. 11 is a graph demonstrating the effect of anti-GITR on I-κB degradation in CD3 activated T cells.
Figure 12:
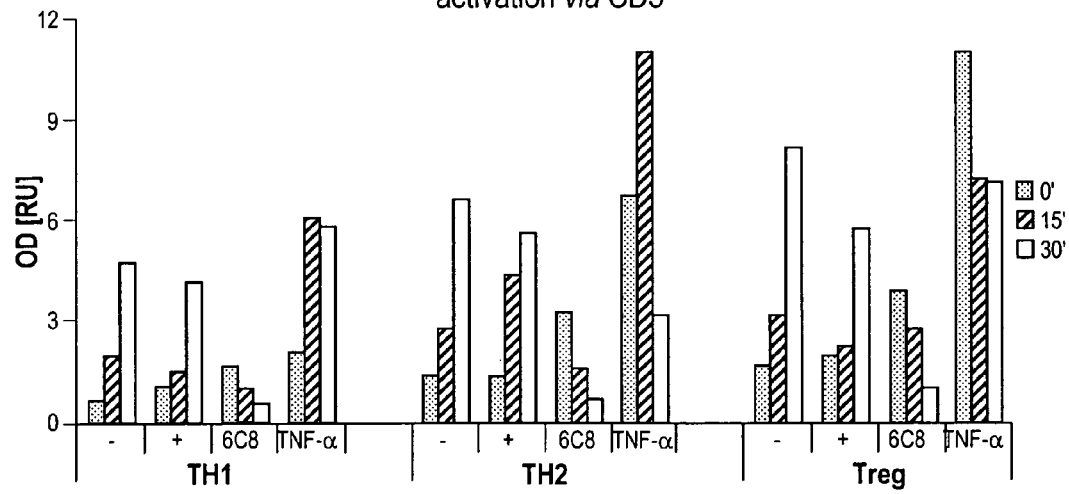
FIG. 12 is a graph demonstrating the effect of anti-GITR on I-κB phosphorylation in CD3 activated T cells.
Figure 13:
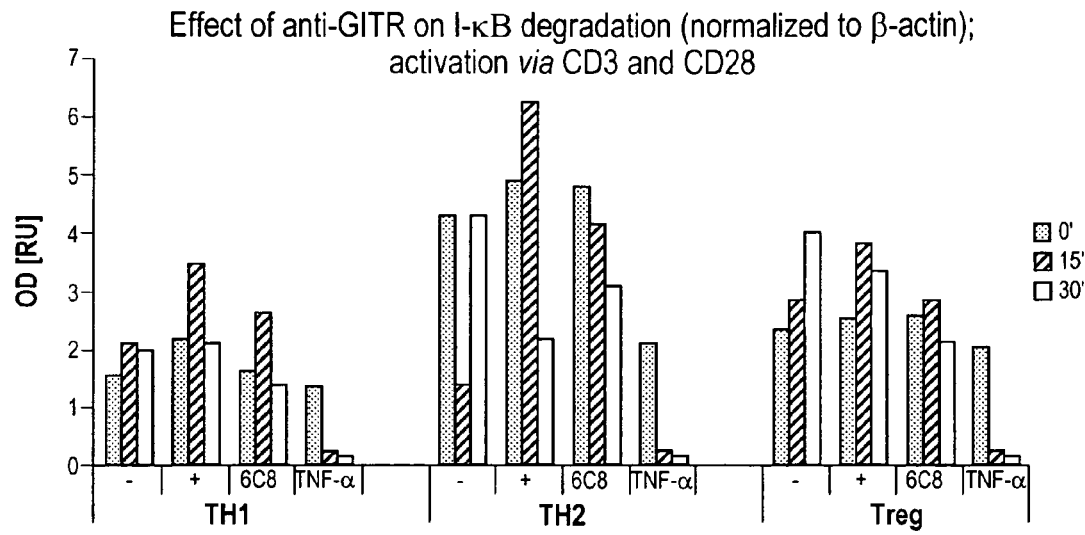
FIG. 13 is a graph demonstrating the effect of anti-GITR on I-κB degradation, in CD3 plus CD28 activated T cells.
Figure 14:
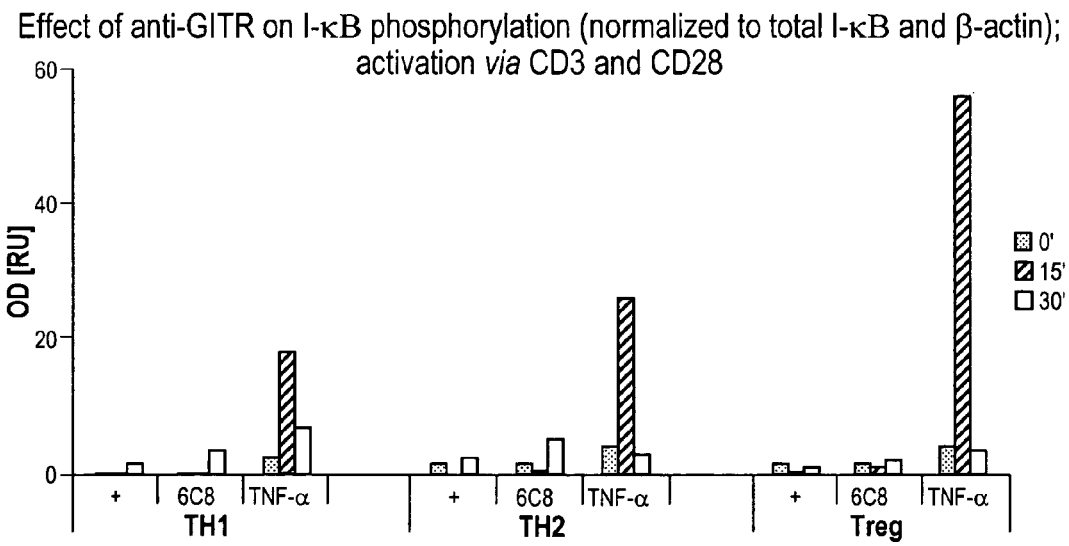
FIG. 14 is a graph demonstrating the effect of anti-GITR on I-κB phosphorylation, CD3 plus CD28 activated T cells.
Figure 15:
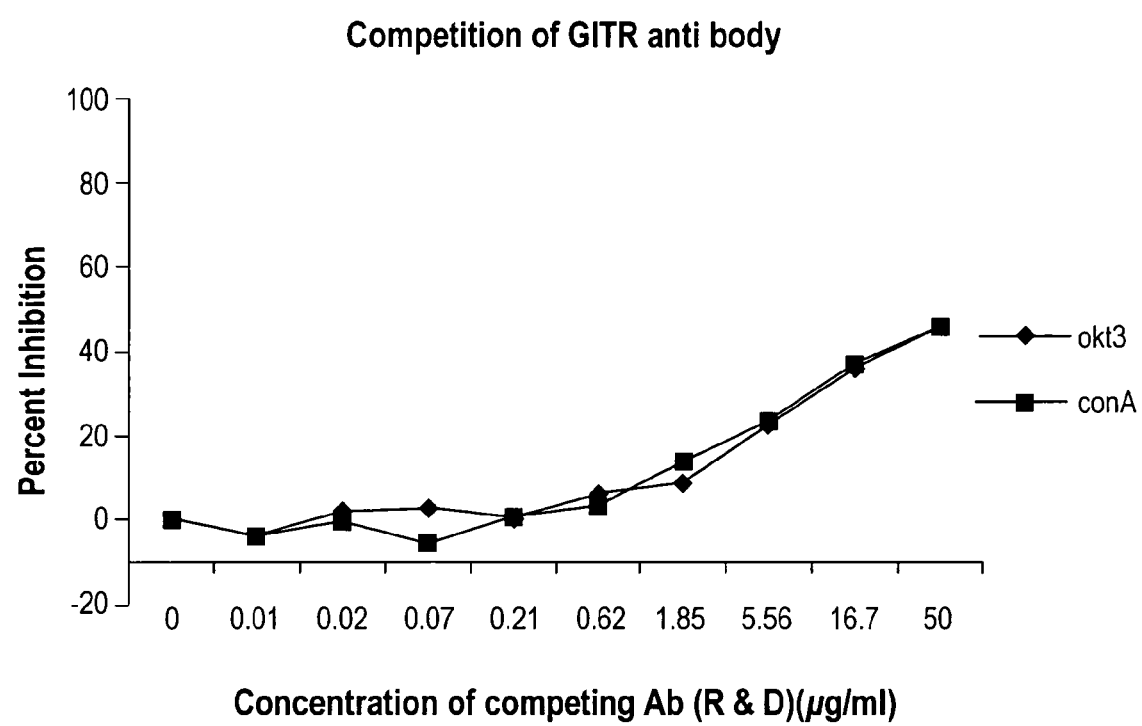
FIG. 15 is a graph demonstrating that 6C8 and the R&D Systems (Minneapolis, Minn.) antibody recognize unique epitopes. The competition assay was performed on both OKT3 and Con A activated lymphocytes. One µg/ml of 6C8 was used with various amounts of the competing R&D Systems antibody (GITR/TNFRSF18 monoclonal antibody). There was some competition observed at the highest concentration of antibody, but this is most likely due to steric hindrance.
Figure 16:
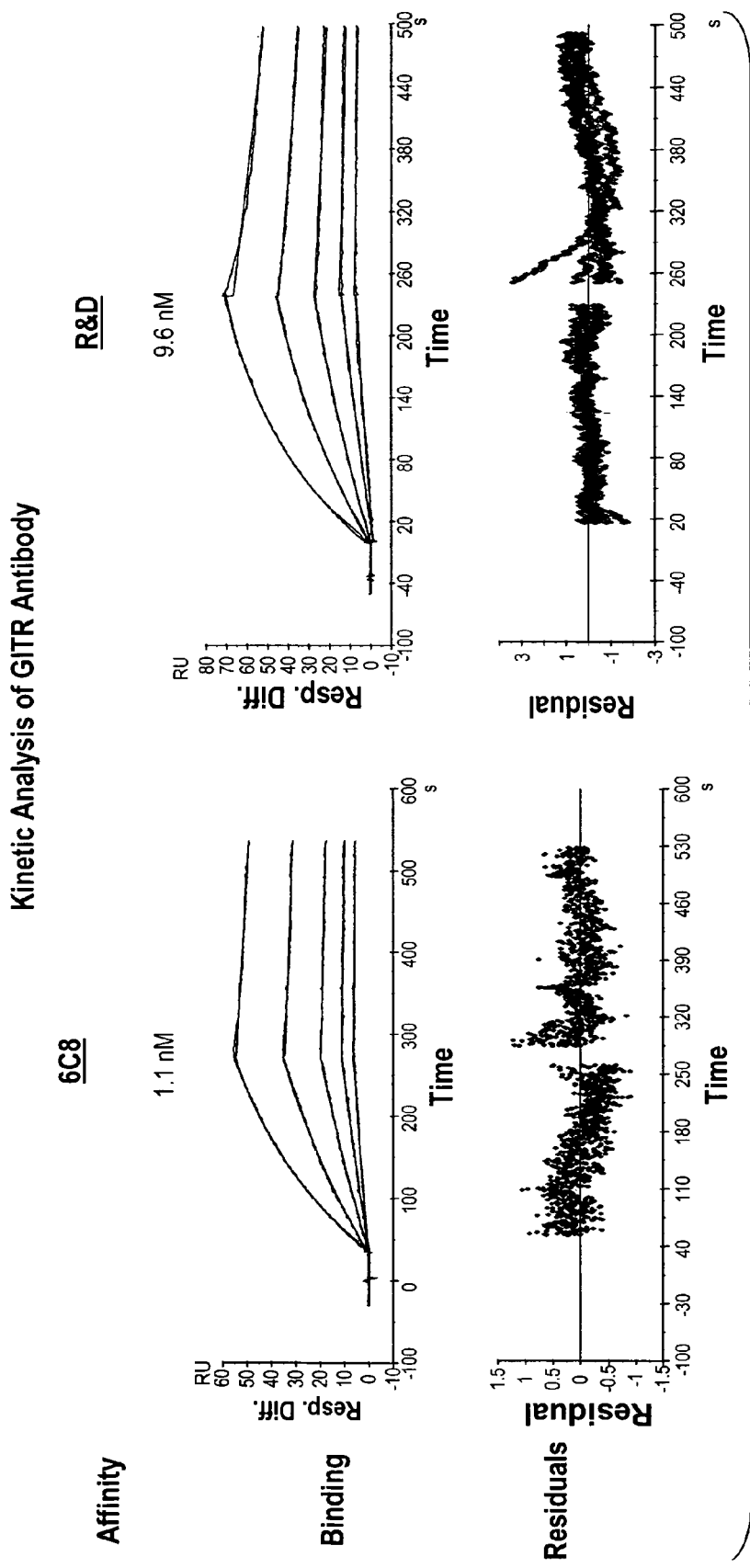
FIG. 16 shows the kinetic analysis of the 6C8 anti-GITR antibody versus the R&D Systems GITR antibody.

Activation of T cells via CD3 or CD3 and CD28 results in activation of I-κB signaling pathways, as assessed by both I-κB phosphorylation (FIGS. 12 and 14) and subsequent degradation (FIGS. 11 and 13).

As presented on FIG. 11, under conditions of partial activation, anti-GITR has a significant effect on I-κB signaling, as assessed by time dependent degradation of -I-κB. In the presence of the GITR binding molecule, degradation is significantly attenuated, at all time points analyzed. Above changes nicely correlate with decline of phosphorylation of I-κB (FIG. 12).

Interestingly the magnitude of response is greater for TH2 and Treg vs. TH 1. Furthermore the expression of GITR appears to be higher on TH 1 cells, compared to TH2 and Treg cells, (as assessed by MCF (mean channel fluorescence)) in parallel experiments. T cells fully activated via crosslinking to CD3 and CD28 loose their responsiveness to anti-GITR, however fully retain activation of 1-Kb via TNF-α.

Example 5

The 6C8 Antibody Enhances Immune Responses

Figure 17:
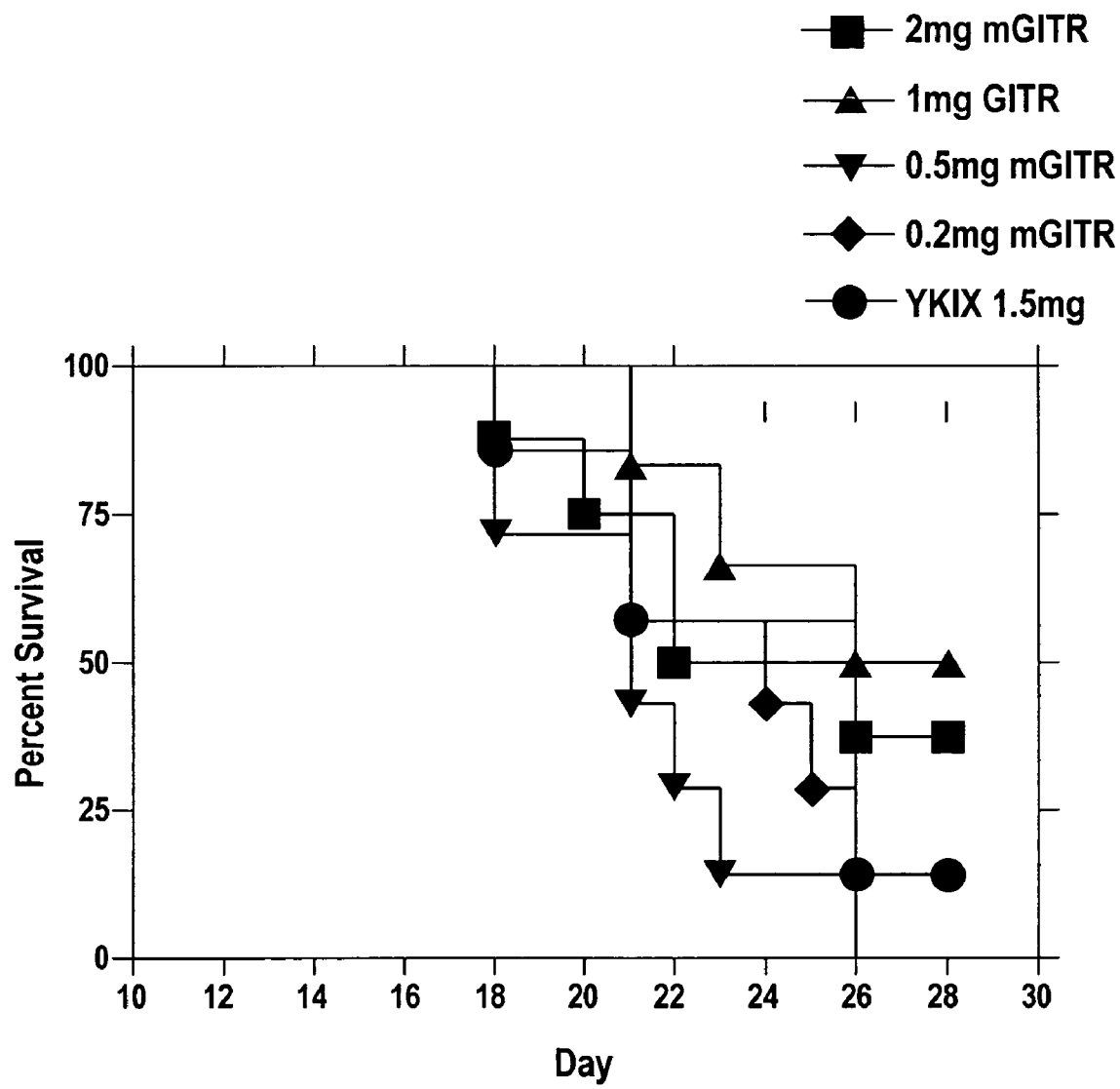
FIG. 17 is a graph showing the percent survival of mice injected with mitomycin C treated B16 cells following treatment with anti-GITR antibody (2F8 rat anti-mouse GITR binding molecule).

The B16 melanoma tumor model is an aggressive melanoma model that has been used to study the role of T regulatory cells in cancer. Treatment of mice with a depleting anti-CD25 antibody or anti-CTLA-4 has shown promising results in this model. In both cases, treatments were able to delay tumor on-set and tumor size. Since GITR is expressed on CD25+ cells and may be involved in abrogating the suppression of T regulatory cells, B16-tumor bearing mice were treated with anti-GITR binding molecule to determine if there was an effect on tumor on-set or tumor size. Treatment with anti-GITR binding molecule one day after the mice were injected with tumor resulted in a delayed onset and size of tumor (FIG. 17). In addition, there were still mice in the GITR treated group that were tumor-free at the end of the study.

All animals were injected with $10^4$ B16 melanoma cells in their right flank on day 0. The GITR groups received 2 milligrams, 1 milligram, 0.5, milligrams, or 0.2 milligrams of anti-GITR binding molecule on Day 1. Measurable tumors were visible starting on Day 16.

Example 6

Simultaneous Delivery of Anti-GITR and Antigen Results in an Adjuvant Effect

The adjuvant effect of an anti-mGITR antibody on the humoral response to ovalbumin (Ova) or hemagglutinin (HA) was further investigated. Mice were treated with either no antibody, YAML (isotype control), or 2F8 (rat-anti-mGITR) on days −1, 0, and 1 at 0.4 mg/day. To assess the importance of Fc receptor engagement in the mechanism of action of the binding molecule, an additional group of animals was treated with 6 mg/day of 2F8 F(ab')2 on days -1, 0 and 1. This dose was selected based on the short half life of F(ab')2 compared to whole antibody. Mice were immunized with Ova (100 g) or HA (10 µg) on day 0. The Ova treated mice were challenged with 100 µg Ova on day 14 and then bled on days 21 and 28 to obtain serum samples for ELISA assays. HA treated mice were challenged with 5 µg HA on day 14 and also bled on days 21 and 28.

Serum concentrations of 2F8 and 2F8 F(ab')2 were monitored to assess the pharmacokinetic profiles of the binding molecules. On day 1, serum levels of binding molecule in mice treated with 2F8 or the 2F8 F(ab')2 fragments were comparable. Binding molecule was detected in the 2F8 treated mice until day 9, whereas the 2F8 F(ab')2 fragment treated mice had detectable binding molecule only until day 3, despite a 15× higher dose.

The results demonstrate that in the HA arm of the study, mice treated with 2F8 had a 4 and 5 fold increase in anti-HA antibodies compared to animals treated with no antibody and an 18 and 20 fold increase in anti-HA antibodies compared to YAML treated mice on days 21 and 28, respectively (FIG. 19). The anti-HA titer observed with the anti-mGITR antibody as an adjuvant is comparable to the titer observed when HA was administered with Incomplete Freund's adjuvant (IFA). This suggests that the response observed with the anti-mGITR antibody is comparable to one of the most potent adjuvants frequently utilized in immunological studies.

In the Ova arm of the study, mice treated with 2F8 had a 13 and 6 fold increase in anti-Ova antibodies compared to animals treated with no antibody and a 17 and 8 fold increase in anti-Ova antibodies compared to YAML treated mice on day 21 and day 28, respectively (FIG. 20). The effect of the 2F8 antibody on the response to Ova was comparable to the observed response to HA. Mice treated with 2F8 F(ab')2 had a 4 and 3 fold increase in Anti-Ova antibodies compared to animals treated with no antibody and a 6 and 5 fold increase in anti-Ova antibodies compared to YAML treated mice on day 21 and day 28, respectively (FIG. 20). The dose of F(ab')2 and the different pharmacokinetic profile compared to whole antibody may explain the decreased anti-Ova response when compared to the 2F8 treated mice.

Together, these data demonstrate that the effect of the 2F8 antibody on the humoral response to antigen is predominantly attributable to the F(ab')2 portion of the antibody and that Fc receptor engagement may not be required for the adjuvant effect of the anti-mGITR antibody.

Example 7

Preparation of a Chimeric Anti-GITR Binding Molecule

The 6C8 variable light chain region was grafted to a human light chain constant region using conventional molecular biological techniques. The IgG1 light chain constant region was used. The amino acid sequence of the complete chimeric light chain GITR binding molecule is shown below:

```
                                          (SEQ ID NO: 22)
DIVMTQSQKFMSTSVGDRVSVTCKASQNVGTNVAWYQQKPGQSPKALIYS

ASYRYSGVPDRFTGSGSGTDFTLTINNVHSEDLAEYFCQQYNTDPLTFGA

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

The 6C8 variable heavy chain was also grafted to a human heavy chain constant region using conventional molecular biological techniques. The IgG1 heavy chain constant region was used. The amino acid sequence of the complete chimeric heavy chain GITR binding molecule is shown below (also referred to as "Gly"):

```
                                          (SEQ ID NO: 23)
QVTLKESGPGILKPSQTLSLTCSFSGFSLSTSGMGVGWIRQPSGKGLEWL

AHIWWDDDKYYNPSLKSQLTISKDTSRNQVFLKITSVDTADAATYYCART

RRYFPFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.
```

Since the amino acid sequence NX(S/T) is a putative consensus sequence for a glycosylation site which may affect the production of the binding molecule, and IgG1 constant region of the 6C8 heavy chain has the sequence NST, a second version of the heavy chain constant region was prepared to conservatively substitute a glutamine for an asparagine at amino acid residue 299 (bolded and underlined above) of SEQ ID NO:23. Accordingly, a second human constant region was grafted to the 6C8 heavy chain variable region. The amino acid sequence of the complete chimeric heavy chain GITR binding molecule is shown below (also referred to a "Agly"):

```
                                            (SEQ ID NO: 24)
QVTLKESGPGILKPSQTLSLTCSFSGFSLSTSGMGVGWIRQPSGKGLEWL

AHIWWDDDKYYNPSLKSQLTISKDTSRNQVFLKITSVDTADAATYYCART

RRYFPFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.
```

Example 8

Preparation of Humanized Forms of the 6C8 Anti-GITR Binding Molecule

The CDR homology based strategy described in Hwang et al. (2005) *Methods* (36) 35-42 was used to humanize 6C8. The heavy and light chain amino acid sequences were blasted using a publicly available database, and the results indicated that 6C8 had a 3-1 heavy chain canonical structure and a 2-1-1 light chain canonical structure. From this, all germ line kappa chain V genes with a 2-1-1 canonical structure in the IMGT database were compared with the 6C8 antibody sequence. The same was done for the heavy chain where all 3-1 germ line heavy chain V genes were compared to the 6C8 amino acid sequence. Only the CDR sequences were compared and the frameworks were selected based on which germline sequences had the most matches in the CDRs. (see alignments below).

For the light chain, the 3-15*01 sequence had 14 matches in the CDRs and was selected. Since CDR 3 ends with leucine and threonine, the Jk4 J gene segment sequence was used.

Light Chain V Genes with 2-1-1 Canonical Structure
(CDR1, CDR2, and CDR3 disclosed as residue 24-34,50-56, and 89-95 of SEQ ID NOs: 43, 42, 41, 40, 36, 35, 33, 32, 30, 29 28, 26, 25, and 44, respectively, in order of appearance.)

| IMGT Gene Name | CDR1 | CDR2 | CDR3 | IDs |
|---|---|---|---|---|
| IGKV1-5 | RASQSISSWLA...... | DASSLES....... | QQYNSYS... | 11 |
| IGKV1-6 | RASQGIRNDLG...... | AASSLSQ....... | LQDYNYP... | 10 |
| IGKV1-9 | RASQGISSYLA...... | AASTLQS....... | QQLNSYP... | 11 |
| IGKV1-12 | RASQGISSWLA...... | AASSLQS....... | QQANSFP... | 11 |
| IGKV1-16 | RASQGISSWLA...... | AASSLQS....... | QQYNSYP... | 12 |
| IGKV1D-16 | RARQGISSWLA...... | AASSLQS....... | QQYNSYP... | 11 |
| IGKV1-17 | RASQGIRNDLG...... | AASSLQS....... | LQHNSYP... | 9 |
| IGKV1-27 | RASQGISNYLA...... | AASTLQS....... | QKYNSAP... | 11 |
| IGKV1-33 | QASQDISNYLN...... | DASNLET....... | QQYDNLP... | 9 |
| IGKV1-39 | RASQSISSYLN...... | AASSLQS....... | QQSYSTP... | 9 |
| IGKV1D-43 | WASQGISSYLA...... | YASSLQS....... | QQYYSTP... | 11 |
| IGKV3-11 | RASQSVSSYLA...... | DASNRAT....... | QQRSNWP... | 11 |
| IGKV3D-11 | RASQGVSSYLA...... | DASNRAT....... | QQRSNWH... | 10 |
| IGKV3-15 | RASQSVSSNLA...... | GASTRAT....... | QQYNNWP... | 14 |
| 6C8 | KASQNVGTNVA...... | SASYRYS....... | QQYNTDP | |

All germ line light chain kappa chain V genes with a 2-1-1 canonical structure in the IMGT database were compared with the 6C8 antibody sequence. The same was done for the heavy chain where all 3-1 germ line heavy chain V genes were compared to the 6C8 amino acid sequence Using this methodology one version of the light chain was made: EIVMTQSPATLSVSPGERATLSCKASQN-VGTNVAWYQQKPGQAPRLLIYSASYR YSGIPARF-SGSGSGTEFTLTISSLQSEDFAVYYC-QQYNTDPLTFGGGTKVEIK (SEQ ID NO:44) (the CDRs are italicized)

For the heavy chain, sequence 2-05*01 had 17 matches. However, the sequences around CDR 3 were different than 6C8 (YYCAR (Residues 114-118 of SEQ ID NO: 1) vs. YYCAHR (SEQ ID NO: 69)). Since CDR 3 has been shown to be the most important CDR for recognition, it is important to keep this area as perfectly matched as possible. Sequence 2-70*01 had 16 matches in the CDRs and the sequences right before CDR 3 perfectly matched 6C8's and so 2-70*01 was selected.

For the J gene segment of the heavy chain, JH4 had the most matches and was therefore, selected. The amino acid sequences were then reverse translated and primers corresponding to the desired nucleotide sequence were obtained from IDT (Coralville, Iowa).

Heavy Chain V Genes with 3-1 Canonical Structures (CDR1 and CDR2, disclosed as residue 31-27 and 52-67, of SEQ ID NOs: 45-53, respectively, in order of appearance.)

| IMGT Gene Name | CDR1 | CDR2 | IDs |
|---|---|---|---|
| IGHV2-5 | TSGVGVG..... | LIYWNDDKRYSPSLKS | 17 |
| IGHV2-26 | NARMGVS..... | HIFSNDEKSYSTSLKS | 12 |
| IGHV2-70 | TSGMCVS..... | LIDWDDDKYYSTSLKT | 16 |
| IGHV4-30-2 | SGGYSWS..... | YIYHSGSTYYNPSLKS | 10 |
| IGHV4-30-4 | SGDYWS..... | YIYYSGSTYYNPSLKS | 9 |
| IGHV4-31 | SGGYYWS..... | YIYYSGSTYYNPSLKS | 9 |
| IGHV4-39 | SSSYYWG..... | SIYYSGSTYYNPSLKS | 10 |
| IGHV4-61 | SGSYYWS..... | YIYYSGSTNYNPSLKS | 8 |
| 6C8 | TSGMGVG..... | HIWWDDDKYYNPSLKS | |

Using this methodology one version of the heavy chain was made: QVTLRESGPALVKPTQTLTLTCTFSGF-SLSTSGMGVGWIRQPPGKALEWLAHI WWD-DDKYYNPSLKSRLTISKDTSKNQVVLT-MTNMDPVDTATYYCARTRRYFP FAYWGQGTLVTVSS (SEQ ID NO:53) (also referred to as "N")

Since the amino acid sequence NX(S/T) is a putative consensus sequence for a glycosylation site which may affect the production of the binding molecule, and CDR2 of the 6C8 heavy chain has the sequence NPS, a second version of the heavy chain was prepared to conservatively substitute a glutamine for an asparagine at amino acid residue 62 (bolded and underlined above) of SEQ ID NO:53. Accordingly, a second heavy chain version was made: QVTLRESG-PALVKPTQTLTLTCTFSGFSLSTSGMGVGWIR QPPGKALEWLAHI WWDDDKYYOPSLKSR-LTISKDTSKNQVVLTMTNMDPVDTATYY-CARTRRYFP FAYWGQGTLVTVSS (SEQ ID NO:54) (also referred to as "Q").

A CLUSTAL W (1.82) multiple sequence alignment (using a Blosum scoring matrix with a gap penalty of 10) of the 6C8 light chain variable region (Residues 1-107 of SEQ ID NO: 22) and the 3-15*01 germline light chain sequence (SEQ ID NO: 25) was also performed. The results are presented below:

```
6C8      DIVMTQSQKFMSTSVGDRVSVTCKASQNVGTNVAWYQQKPGQSPKALIYSASYRYSGVPD
3-15*01  EIVMTQSPATLSVSPGERATLSCRASQSVSSNLAWYQQKPGQAPRLLIYGASTRATGIPA
         :******  :*.* *;*..:::*:***.*..*:*********:: ***.** * :*:*

6C8      RFTGSGSGTDFTLTINNVHSEDLAEYFCQQYNTDPLTFGAGTKLEIK
3-15*01  RFSGSGSGTEFTLTISSLQSEDFAVYYCQQYNNWP------------
         **:******:*****.:;:**:*.*:*****. *
```

Based on the CLUSTAL W analyses, several amino acid residues in the human framework were identified for potential substitution with amino acid residues corresponding to the 6C8 framework residues in the humanized 6C8 light chain. Specifically, the E at position 1, the P at position 8, the A at position 9, the T at position 10, the L at position 11, the V at position 13, the P at position 15, the E at position 17, the A at position 19, the T at position 20, the L at position 21, the S at position 22, the A at position 43, the R at position 45, the L at position 46, the I at position 58, the A at position 60, the S at position 63, the E at position 70, the S at position 76, the S at position 77, the L at position 78, the Q at position 79, the F at position 83, the V at position 85, the Y at position 87, the G at position 100, and the V at position 104.

Similarly, a CLUSTAL W (1.82) multiple sequence alignment (using a Blosum scoring matrix with a gap penalty of 10) of the 6C8 heavy chain variable region (Residues 1-119 of SEQ ID NO: 23) and the germline heavy chain proteins with a 2-70*01 amino acid sequence (SEQ ID NO: 47) was also performed. The results are presented below:

```
6C8      QVTLKESGPGILKPSQTLSLTCSFSGFSLSTSGMGVGWIRQPSGKGLEWLAHIWWDDDKY
2-70*01  QVTLRESGPALVKPTQTLTLTCTFSGFSLSTSGMCVSWIRQPPGKALEWLALIDWDDDKY
         ****:****..:**:***:***:************ *.*****.**.*****.*.******

6C8      YNPSLKSQLTISKDTSRNQVFLKITSVDTADAATYYCARTRRYFPPAYWGQGTLVTVSS
2-70*01  YSTSLKTRLTISKDTSKNQVVLTMTNMDPVDTATYYCARI-------------------
         *..***::********:***.*..*..*.*:**:*******
```

Based on the CLUSTAL W analyses, several amino acid residues in the human framework were identified for potential substitution with amino acid residues corresponding to the 6C8 framework residues in the humanized 6C8 heavy chain.

Specifically, the R at position 5, the A at position 10, the L at position 11, the V at position 12, the T at position 15, the T at position 19, the T at position 23, the P at position 43, the A at position 46, the R at position 68, the K at position 77, the V at position 81, the T at position 83, the M at position 84, the N at position 86, the M at position 87, the P at position 89, the V at position 90, and/or the T at position 92.

Four humanized full-length 6C8 binding molecules were made having the following humanized heavy and light chain combinations:

Full-length Version 1 (HuN6C8-Gly)—humanized (Hu) 6C8 Light chain (L)/humanized Heavy chain with the N in CDR2 ("N") and comprising a constant region having an N ("Gly")

Full-length Version 2 (HuN6C8-Agly)—humanized (Hu) 6C8 Light chain (L)/humanized Heavy chain with the N in CDR2 ("N") and comprising a constant region having an A ("Agly")

Full-length Version 3—(HuQ6C8-Gly)—humanized (Hu) 6C8 Light chain (L)/humanized Heavy chain with the Q in CDR2 ("Q") and comprising a constant region having an N ("Gly")

Full-length Version 4—(HuQ6C8-Agly) humanized (Hu) 6C8 Light chain (L)/humanized Heavy chain with the Q in CDR2 ("Q") and comprising a constant region having an A ("Agly")

The amino acid sequence of the glycosylated IgG1 heavy chain constant region that was used to make the full-length binding molecules is shown below:

(SEQ ID NO: 55)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK.

The amino acid sequence of the aglycosylated IgG1 heavy chain constant region that was used to make the full-length binding molecules is shown below:

(SEQ ID NO: 56)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYASTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK.

The amino acid sequence of the IgG1 light chain constant region that was used to make the full-length binding molecules is shown below:

(SEQ ID NO: 57)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC.

The complete amino acid sequence of the humanized 6C8 light chain is shown below:

(SEQ ID NO: 58)
EIVMTQSPATLSVSPGERATLSCKASQNVGTNVAWYQQKPGQAPRLLIYS
ASYRYSGIPARFSGSGSGTEFTLTISSLQSEDFAVYYCQQYNTDPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.

The leader sequence METQSQVFVYMLLWLSGVDG (SEQ ID NO:59) may optionally be included.

The complete amino acid sequences of the humanized 6C8 heavy chain versions HuN6C8-Agly, HuQ6C8-Gly, and HuQ6C8-Agly are shown below:

HuN6C8-Gly
(SEQ ID NO: 60)
QVTLRESGPALVKPTQTLTLTCTFSGFSLSTSGMGVGWIRQPPGKALEWL

AHIWWDDDKYYNPSLKSRLTISKDTSKNQVVLTMTNMDPVDTATYYCART

RRYFPFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK;

HuN6C8-Agly
(SEQ ID NO: 61)
QVTLRESGPALVKPTQTLTLTCTFSGFSLSTSGMGVGWIRQPPGKALEWL

AHIWWDDDKYYNPSLKSRLTISKDTSKNQVVLTMTNMDPVDTATYYCART

RRYFPFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK;

HuQ6C8-Gly
(SEQ ID NO: 62)
QVTLRESGPALVKPTQTLTLTCTFSGFSLSTSGMGVGWIRQPPGKALEWL

AHIWWDDDKYYQPSLKSRLTISKDTSKNQVVLTMTNMDPVDTATYYCART

RRYFPFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK;
and

HuQ6C8-Agly
(SEQ ID NO: 63)
QVTLRESGPALVKPTQTLTLTCTFSGFSLSTSGMGVGWIRQPPGKALEWL

AHIWWDDDKYYQPSLKSRLTISKDTSKNQVVLTMTNMDPVDTATYYCART

RRYFPFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK.

The leader sequence MDRLTFSFLLLIVPAYVLS (SEQ ID NO:64) may optionally be included.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated monoclonal antibody comprising a light chain and a heavy chain, or an antigen-binding fragment thereof, which antibody or antigen-binding fragment specifically binds glucocorticoid-induced TNFR family-related receptor (GITR), wherein said antibody or antigen-binding fragment thereof comprises (a) the heavy chain variable region set forth in amino acid residues 20-138 of SEQ ID NO:1 or amino acid residues 20-138 of SEQ ID NO:66 and (b) the light chain variable region set forth in amino acid residues 21-127 of SEQ ID NO:2.

2. An isolated monoclonal antibody comprising a light-chain and a heavy chain, or an antigen-binding fragment thereof, which antibody or antigen-binding fragment specifically binds glucocorticoid-induced TNFR family-related receptor (GITR), wherein said antibody or antigen-binding fragment thereof comprises (a) the heavy chain complementarity determining region (CDR) amino acid sequences in SEQ ID NO:1 and (b) the light chain CDR amino acid sequences in SEQ ID NO:2.

3. An isolated monoclonal antibody comprising a light chain and a heavy chain, or an antigen-binding fragment thereof, which antibody or antigen-binding fragment specifically binds glucocorticoid-induced TNFR family-related receptor (GITR), wherein said antibody or antigen-binding fragment thereof comprises the light chain complementarity determining region (CDR) amino acid sequences shown in amino acid residues 44-54 of SEQ ID NO:2, amino acid residues 70-76 of SEQ ID NO:2, and amino acid residues 109-117 of SEQ ID NO:2, and heavy chain CDR amino acid sequences shown in amino acid residues 45-56 of SEQ ID NO:1, amino acid residues 119-127 of SEQ ID NO:1, and one of amino acid residues 71-86 of SEQ ID NO:1 and amino acid residues 71-86 of SEQ ID NO:66.

4. An isolated monoclonal antibody, or antigen-binding fragment thereof, which antibody or antigen-binding fragment specifically binds glucocorticoid-induced-TNFR family-related receptor (GITR) on human T cells and human dendritic cells and has a binding constant (Kd) of $1 \times 10^{-9}$ or less;

wherein said antibody or antigen-binding fragment thereof comprises the light chain complementarity determining region (CDR) amino acid sequences shown in amino acid residues 44-54 of SEQ ID NO:2, amino acid residues 70-76 of SEQ ID NO:2, and amino acid residues 109-117 of SEQ ID NO:2, and heavy chain CDR amino acid sequences shown in amino acid residues 45-56 of SEQ ID NO:1, amino acid residues 119-127 of SEQ ID NO:1, and one of amino acid residues 71-86 of SEQ ID NO:1 and amino acid residues 71-86 of SEQ ID NO:66.

5. An isolated monoclonal antibody comprising a light-chain and a heavy chain, or an antigen-binding fragment thereof, which antibody or antigen-binding fragment specifically binds glucocorticoid-induced TNFR family-related receptor (GITR), wherein said antibody or antigen-binding fragment thereof comprises one of:

a) the heavy chain complementarity determining region (CDR) amino acid sequences in SEQ ID NO:1 and the light chain CDR amino acid sequences in SEQ ID NO:2; or b) the light chain complementarity determining region (CDR) amino acid sequences shown in amino acid residues 44-54 of SEQ ID NO:2, amino acid residues 70-76 of SEQ ID NO:2, and amino acid residues 109-117 of SEQ ID NO:2, and heavy chain CDR amino acid sequences shown in amino acid residues 45-56 of SEQ ID NO:1, amino acid residues 119-127 of SEQ ID NO:1, and one of amino acid residues 71-86 of SEQ ID NO:1 and amino acid residues 71-86 of SEQ ID NO:66;

wherein the antibody or antigen-binding fragment comprises human heavy and light chain framework regions, except that one or more human framework amino acid residues is backmutated to a corresponding murine amino acid residue.

6. The antibody or antigen-binding fragment of claim 2, 3, or 4, wherein the antibody or antigen-binding fragment comprises human heavy and light chain framework regions.

7. The antibody or antigen-binding fragment of claim 5, wherein the antibody or antigen-binding fragment has a binding constant (Kd) of $1 \times 10^{-9}$ or less.

8. The antibody or antigen-binding fragment of claim 6, wherein the heavy and light chain framework regions are germline heavy and light chain framework regions.

9. The antibody or antigen-binding fragment of claim 1 or 4, wherein the antibody or antigen-binding fragment comprises an IgG2b heavy chain constant region.

10. The antibody or antigen-binding fragment of claim 2, 3, or 4, wherein the antibody or antigen-binding fragment binds to human GITR.

11. The antibody or antigen-binding fragment of claim 2, 3, or 4, wherein the antibody or antigen-binding fragment modulates the activity of human GITR.

12. The antibody or antigen-binding fragment of claim 2, 3, or 4, wherein the antibody or antigen-binding fragment is a chimeric antibody or antigen-binding fragment.

13. The antibody or antigen-binding fragment of claim 2, 3, or 4, wherein the antibody or antigen-binding fragment is a humanized antibody or antigen-binding fragment.

14. A composition comprising the antibody or antigen-binding fragment of claim 2, 3, or 4 and a pharmaceutically acceptable carrier.

15. The composition of claim 14, further comprising at least one additional therapeutic agent for treating cancer in a subject.

16. The composition of claim 14, further comprising at least one additional therapeutic agent for treating a viral infection in a subject.

17. The composition of claim 14, further comprising at least one tumor antigen for treating cancer in a subject.

18. The composition of claim 14, further comprising at least one antigen from a pathogenic agent for treating a viral infection in a subject.

19. The antigen-binding fragment of claim 1, 2, 3, or 4, which is an antigen binding fragment selected from the group consisting of a Fab fragment, a F(ab') fragment, a F(ab')2 fragment, a scFv molecule, an Fd fragment, an Fv fragment, and a single domain antibody fragment (DAb).

20. The antibody or antigen-binding fragment, of claim 1, 2, 3, or 4 comprising a human IgG1 heavy chain constant region.

21. An isolated monoclonal antibody, or an antigen-binding fragment thereof, wherein the antibody or antigen-binding fragment specifically binds glucocorticoid-induced TNFR family-related receptor (GITR) and competes for binding to GITR with the antibody or antigen-binding fragment of claim 1, 2, 3 or 4.

22. The antibody or antigen-binding fragment of claim 4, wherein the antibody or antigen-binding fragment comprises the chimeric light chain amino acid sequence set forth in SEQ ID NO:22.

23. The antibody or antigen-binding fragment of claim 4, wherein the antibody or antigen-binding fragment comprises the chimeric heavy chain amino acid sequence set forth in one of SEQ ID NO:23 and SEQ ID NO:24.

24. The antibody or antigen-binding fragment of claim 4, wherein the antibody or antigen-binding fragment comprises the humanized light chain amino acid sequence set forth in SEQ ID NO:44.

25. The antibody or antigen-binding fragment of claim 4, wherein the antibody or antigen-binding fragment comprises the humanized heavy chain amino acid sequence set forth in one of SEQ ID NO:53 or SEQ ID NO:54.

26. The antibody or antigen-binding fragment of claim 4, wherein the antibody or antigen-binding fragment comprises the humanized light chain amino acid sequence set forth in SEQ ID NO:58.

27. The antibody or antigen-binding fragment of claim 4, wherein the antibody or antigen-binding fragment comprises a humanized heavy chain amino acid sequence selected from the group of amino acid sequences set forth in SEQ ID NO:60, SEQ ID NO:61, SEQ ID NO:62, and SEQ ID NO:63.

* * * * *

UNITED STATES PATENT AND TRADEMARK OFFICE
CERTIFICATE OF CORRECTION

| | | |
|---|---|---|
| PATENT NO. | : 7,812,135 B2 | Page 1 of 1 |
| APPLICATION NO. | : 11/389880 | |
| DATED | : October 12, 2010 | |
| INVENTOR(S) | : L. Mary Smith et al. | |

It is certified that error appears in the above-identified patent and that said Letters Patent is hereby corrected as shown below:

Col. 127, Claim 19, line 2, delete "antigen binding" and insert -- antigen-binding --, therefor.

Col. 128, Claim 25, line 4, after "NO:53" delete "or" and insert -- and --, therefor.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,812,135 B2
APPLICATION NO. : 11/389880
DATED : October 12, 2010
INVENTOR(S) : L. Mary Smith et al.

It is certified that error appears in the above-identified patent and that said Letters Patent is hereby corrected as shown below:

Column 127, line 40 (Claim 19, line 2) delete "antigen binding" and insert -- antigen-binding --, therefor.

Column 128, line 29 (Claim 25, line 4) after "NO:53" delete "or" and insert -- and --, therefor.

This certificate supersedes the Certificate of Correction issued December 7, 2010.

Signed and Sealed this
Twenty-fifth Day of January, 2011

David J. Kappos
*Director of the United States Patent and Trademark Office*

SEQUENCE LISTING

```
<160> NUMBER OF SEQ ID NOS: 69

<210> SEQ ID NO 1
<211> LENGTH: 138
<212> TYPE: PRT
<213> ORGANISM: Mus musculus

<400> SEQUENCE: 1

Met Asp Arg Leu Thr Phe Ser Phe Leu Leu Leu Ile Val Pro Ala Tyr
  1               5                  10                  15

Val Leu Ser Gln Val Thr Leu Lys Glu Ser Gly Pro Gly Ile Leu Lys
             20                  25                  30

Pro Ser Gln Thr Leu Ser Leu Thr Cys Ser Phe Ser Gly Phe Ser Leu
         35                  40                  45

Ser Thr Ser Gly Met Gly Val Gly Trp Ile Arg Gln Pro Ser Gly Lys
     50                  55                  60
```

```
Gly Leu Glu Trp Leu Ala His Ile Trp Trp Asp Asp Lys Tyr Tyr
 65                  70                  75                  80

Asn Pro Ser Leu Lys Ser Gln Leu Thr Ile Ser Lys Asp Thr Ser Arg
                 85                  90                  95

Asn Gln Val Phe Leu Lys Ile Ser Val Asp Thr Ala Asp Ala Ala
            100                 105                 110

Thr Tyr Tyr Cys Ala Arg Thr Arg Arg Tyr Phe Pro Phe Ala Tyr Trp
        115                 120                 125

Gly Gln Gly Thr Leu Val Thr Val Ser Ser
    130                 135

<210> SEQ ID NO 2
<211> LENGTH: 127
<212> TYPE: PRT
<213> ORGANISM: Mus musculus

<400> SEQUENCE: 2

Met Glu Thr Gln Ser Gln Val Phe Val Tyr Met Leu Leu Trp Leu Ser
  1               5                  10                  15

Gly Val Asp Gly Asp Ile Val Met Thr Gln Ser Gln Lys Phe Met Ser
                 20                  25                  30

Thr Ser Val Gly Asp Arg Val Ser Val Thr Cys Lys Ala Ser Gln Asn
             35                  40                  45

Val Gly Thr Asn Val Ala Trp Tyr Gln Gln Lys Pro Gly Gln Ser Pro
         50                  55                  60

Lys Ala Leu Ile Tyr Ser Ala Ser Tyr Arg Tyr Ser Gly Val Pro Asp
 65                  70                  75                  80

Arg Phe Thr Gly Ser Gly Ser Gly Thr Asp Phe Thr Leu Thr Ile Asn
                 85                  90                  95

Asn Val His Ser Glu Asp Leu Ala Glu Tyr Phe Cys Gln Gln Tyr Asn
            100                 105                 110

Thr Asp Pro Leu Thr Phe Gly Ala Gly Thr Lys Leu Glu Ile Lys
        115                 120                 125

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Ser Leu Ser Thr Ser Gly Met Gly Val Gly
  1               5                  10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ile Trp Trp Asp Asp Lys Tyr Tyr Asn Pro Ser Leu Lys Ser
  1               5                  10                  15

<210> SEQ ID NO 5
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 5

Thr Arg Arg Tyr Phe Pro Phe Ala Tyr
  1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Gln Asn Val Gly Thr Asn Val Ala
  1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Ser Tyr Arg Tyr Ser
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Asn Thr Asp Pro Leu Thr
  1               5

<210> SEQ ID NO 9
<211> LENGTH: 414
<212> TYPE: DNA
<213> ORGANISM: Mus musculus

<400> SEQUENCE: 9
atggacagac ttacattctc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact tctggtatgg gtgtaggctg gattcgtcag     180
ccttcaggga agggtctgga gtggctggcg cacatttggt gggatgatga taagtactat     240
aatccatccc tgaagagcca gctcacaatc tccaaggata cctccagaaa ccaggtattc     300
ctcaagatca ccagtgtgga cactgcagat gctgccactt actactgtgc tcgaactagg     360
aggtacttcc cctttgctta ctggggccaa gggacactag tcacagtctc ctca           414

<210> SEQ ID NO 10
<211> LENGTH: 381
<212> TYPE: DNA
<213> ORGANISM: Mus musculus
```

<400> SEQUENCE: 10

| | | | | | |
|---|---|---|---|---|---|
| atggagacac | agtctcaggt | ctttgtatac | atgttgctgt | ggttgtctgg | tgttgatgga | 60 |
| gacattgtga | tgacccagtc | tcaaaaattc | atgtccacat | cagtaggaga | cagggtcagc | 120 |
| gtcacctgca | aggccagtca | gaatgtgggt | actaatgtag | cctggtatca | acagaaacca | 180 |
| gggcaatctc | ctaaagcact | gatttactcg | gcatcctacc | ggtacagtgg | agtccctgat | 240 |
| cgcttcacag | gcagtggatc | tgggacagat | ttcactctca | ccatcaacaa | tgtgcactct | 300 |
| gaagacttgg | cagagtattt | ctgtcaacaa | tataacaccg | atccgctcac | gttcggagct | 360 |
| gggaccaagc | tggaaatcaa | a | | | | 381 |

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggttttcac tgagcacttc tggtatgggt gtaggc                                36

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cacatttggt gggatgatga taagtactat aatccatccc tgaagagc                   48

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actaggaggt acttcccctt tgcttac                                          27

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaggccagtc agaatgtggg tactaatgta gcc                                   33

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
tcggcatcct accggtacag t                                              21

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caacaatata acaccgatcc gctcacg                                        27

<210> SEQ ID NO 17
<211> LENGTH: 1214
<212> TYPE: DNA
<213> ORGANISM: Homo sapiens

<400> SEQUENCE: 17
gtctacaccc cctcctcaca cgcacttcac ctgggtcggg attctcaggt catgaacggt    60
cccagccacc tccgggcagg gcgggtgagg acggggacgg ggcgtgtcca actggctgtg   120
ggctcttgaa acccgagcat ggcacagcac ggggcgatgg gcgcgtttcg ggccctgtgc   180
ggcctggcgc tgctgtgcgc gctcagcctg ggtcagcgcc ccaccggggg tcccgggtgc   240
ggccctgggc gcctcctgct tgggacggga acggacgcgc gctgctgccg ggttcacacg   300
acgcgctgct gccgcgatta cccgggcgag gagtgctgtt ccgagtggga ctgcatgtgt   360
gtccagcctg aattccactg cggagaccct tgctgcacga cctgccggca ccaccttgt    420 cccccaggcc aggggtaca gtcccagggg aaattcagtt ttggcttcca gtgtatcgac   480
tgtgcctcgg ggaccttctc cggggccac gaaggccact gcaaaccttg acagactgc    540 acccagttcg ggttctctcac tgtgttccct gggaacaaga cccacaacgc tgtgtgcgtc   600
ccagggtccc cgccggcaga gccgcttggg tggctgaccg tcgtcctcct ggccgtggcc   660
gcctgcgtcc tcctcctgac ctcggcccag cttggactgc acatctggca gctgaggagt   720
cagtgcatgt ggccccgaga gacccagctg ctgctggagg tgccgccgtc gaccgaagac   780
gccagaagct gccagttccc cgaggaagag cggggcgagc gatcggcaga ggagaagggg   840
cggctgggag acctgtgggt gtgagcctgg ccgtcctccg gggccaccga ccgcagccag   900
cccctcccca ggagctcccc aggccgcagg ggctctgcgt tctgctctgg gccgggccct   960
gctcccctgg cagcagaagt gggtgcagga aggtggcagt gaccagcgcc ctggaccatg  1020
cagttcggcg gccgcggctg ggccctgcag gagggagaga gagacacagt catggcccc   1080 ttcctccctt gctggccctg atgggtggg gtcttaggac gggaggctgt gtccgtgggt  1140
gtgcagtgcc cagcacggga cccggctgca ggggaccttc aataaacact tgtccagtga  1200
aaaaaaaaaa aaaa                                                   1214

<210> SEQ ID NO 18
<211> LENGTH: 241
<212> TYPE: PRT
<213> ORGANISM: Homo sapiens

<400> SEQUENCE: 18

Met Ala Gln His Gly Ala Met Gly Ala Phe Arg Ala Leu Cys Gly Leu
 1               5                  10                  15

Ala Leu Leu Cys Ala Leu Ser Leu Gly Gln Arg Pro Thr Gly Gly Pro
            20                  25                  30
```

```
Gly Cys Gly Pro Gly Arg Leu Leu Gly Thr Gly Thr Asp Ala Arg
            35                  40                  45

Cys Cys Arg Val His Thr Thr Arg Cys Cys Arg Asp Tyr Pro Gly Glu
 50                  55                  60

Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
            130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
            195                 200                 205

Pro Pro Ser Thr Glu Asp Ala Arg Ser Cys Gln Phe Pro Glu Glu Glu
            210                 215                 220

Arg Gly Glu Arg Ser Ala Glu Glu Lys Gly Arg Leu Gly Asp Leu Trp
225                 230                 235                 240

Val

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Ile Trp Trp Asp Asp Asp Lys Tyr Tyr Gln Pro Ser Leu Lys Ser
 1               5                   10                  15

<210> SEQ ID NO 20
<211> LENGTH: 105
<212> TYPE: PRT
<213> ORGANISM: Mus musculus

<400> SEQUENCE: 20

Ala Asp Ala Ala Pro Thr Val Ser Ile Phe Pro Pro Ser Ser Glu Gln
 1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
            35                  40                  45

Asn Gly Val Leu Asn Ser Trp Thr Asp Gln Asp Ser Lys Asp Ser Thr
 50                  55                  60

Tyr Ser Met Ser Ser Thr Leu Thr Leu Thr Lys Asp Glu Tyr Glu Arg
 65                  70                  75                  80
```

His Asn Ser Tyr Thr Cys Glu Ala Thr His Lys Thr Ser Ser Pro
                85                  90                  95

Ile Val Lys Ser Phe Asn Arg Asn Glu
            100                 105

<210> SEQ ID NO 21
<211> LENGTH: 334
<212> TYPE: PRT
<213> ORGANISM: Mus musculus

<400> SEQUENCE: 21

Ala Lys Thr Thr Pro Pro Ser Val Tyr Pro Leu Ala Pro Gly Cys Gly
 1               5                  10                  15

Asp Thr Thr Gly Ser Ser Val Thr Leu Gly Cys Leu Val Lys Gly Tyr
                20                  25                  30

Phe Pro Glu Ser Val Thr Val Thr Trp Asn Ser Gly Ser Leu Ser Ser
            35                  40                  45

Ser Val His Thr Phe Pro Ala Leu Leu Gln Ser Gly Leu Tyr Thr Met
        50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys Lys Cys Pro Ala Pro Asn Leu Glu Gly Gly Pro Ser Val
        115                 120                 125

Phe Ile Phe Pro Pro Asn Ile Lys Asp Val Leu Met Ile Ser Leu Thr
130                 135                 140

Pro Lys Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Ile Arg Val Val Ser
            180                 185                 190

Thr Leu Pro Ile Gln His Gln Asp Trp Met Ser Gly Lys Glu Phe Lys
        195                 200                 205

Cys Lys Val Asn Asn Lys Asp Leu Pro Ser Pro Ile Glu Arg Thr Ile
210                 215                 220

Ser Lys Ile Lys Gly Leu Val Arg Ala Gln Val Tyr Ile Leu Pro Pro
225                 230                 235                 240

Pro Ala Glu Gln Leu Ser Arg Lys Asp Val Ser Leu Thr Cys Leu Val
                245                 250                 255

Val Gly Phe Asn Pro Gly Asp Ile Ser Val Glu Trp Thr Ser Asn Gly
            260                 265                 270

His Thr Glu Glu Asn Tyr Lys Asp Thr Ala Pro Val Leu Asp Ser Asp
        275                 280                 285

Gly Ser Tyr Phe Ile Tyr Ser Lys Leu Asn Met Lys Thr Ser Lys Trp
290                 295                 300

Glu Lys Thr Asp Ser Phe Ser Cys Asn Val Arg His Glu Gly Leu Lys
305                 310                 315                 320

Asn Tyr Tyr Leu Lys Lys Thr Ile Ser Arg Ser Pro Gly Lys
                325                 330

<210> SEQ ID NO 22

```
<211> LENGTH: 214
<212> TYPE: PRT
<213> ORGANISM: Artificial Sequence
<220> FEATURE:
<223> OTHER INFORMATION: Description of Artificial Sequence: Synthetic
      mouse/human light chain construct

<400> SEQUENCE: 22

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Thr Asn
             20                  25                  30

Val Ala Trp Tyr Gln Gln Lys Pro Gly Gln Ser Pro Lys Ala Leu Ile
         35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Asn Asn Val His Ser
 65                  70                  75                  80

Glu Asp Leu Ala Glu Tyr Phe Cys Gln Gln Tyr Asn Thr Asp Pro Leu
                 85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 449
<212> TYPE: PRT
<213> ORGANISM: Artificial Sequence
<220> FEATURE:
<223> OTHER INFORMATION: Description of Artificial Sequence: Synthetic
      mouse/human heavy chain construct

<400> SEQUENCE: 23

Gln Val Thr Leu Lys Glu Ser Gly Pro Gly Ile Leu Lys Pro Ser Gln
 1               5                  10                  15

Thr Leu Ser Leu Thr Cys Ser Phe Ser Gly Phe Ser Leu Ser Thr Ser
             20                  25                  30

Gly Met Gly Val Gly Trp Ile Arg Gln Pro Ser Gly Lys Gly Leu Glu
         35                  40                  45

Trp Leu Ala His Ile Trp Trp Asp Asp Asp Lys Tyr Tyr Asn Pro Ser
 50                  55                  60

Leu Lys Ser Gln Leu Thr Ile Ser Lys Asp Thr Ser Arg Asn Gln Val
 65                  70                  75                  80

Phe Leu Lys Ile Thr Ser Val Asp Thr Ala Asp Ala Ala Thr Tyr Tyr
                 85                  90                  95
```

Cys Ala Arg Thr Arg Arg Tyr Phe Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 24
<211> LENGTH: 449
<212> TYPE: PRT
<213> ORGANISM: Artificial Sequence
<220> FEATURE:
<223> OTHER INFORMATION: Description of Artificial Sequence: Synthetic
      mouse/human complete chimeric heavy chain

<400> SEQUENCE: 24

-continued

```
Gln Val Thr Leu Lys Glu Ser Gly Pro Gly Ile Leu Lys Pro Ser Gln
  1               5                  10                 15

Thr Leu Ser Leu Thr Cys Ser Phe Ser Gly Phe Ser Leu Ser Thr Ser
             20                  25                 30

Gly Met Gly Val Gly Trp Ile Arg Gln Pro Ser Gly Lys Gly Leu Glu
         35                  40                 45

Trp Leu Ala His Ile Trp Trp Asp Asp Lys Tyr Tyr Asn Pro Ser
     50                  55                 60

Leu Lys Ser Gln Leu Thr Ile Ser Lys Asp Thr Ser Arg Asn Gln Val
 65                  70                 75                  80

Phe Leu Lys Ile Thr Ser Val Asp Thr Ala Asp Ala Thr Tyr Tyr
                 85                  90                 95

Cys Ala Arg Thr Arg Arg Tyr Phe Pro Phe Ala Tyr Trp Gly Gln Gly
             100                 105                110

Thr Leu Val Thr Val Ser Ser Ala Ser Thr Lys Gly Pro Ser Val Phe
             115                 120                125

Pro Leu Ala Pro Ser Ser Lys Ser Thr Ser Gly Gly Thr Ala Ala Leu
             130                 135                140

Gly Cys Leu Val Lys Asp Tyr Phe Pro Glu Pro Val Thr Val Ser Trp
145                 150                 155                160

Asn Ser Gly Ala Leu Thr Ser Gly Val His Thr Phe Pro Ala Val Leu
                 165                 170                175

Gln Ser Ser Gly Leu Tyr Ser Leu Ser Ser Val Val Thr Val Pro Ser
             180                 185                190

Ser Ser Leu Gly Thr Gln Thr Tyr Ile Cys Asn Val Asn His Lys Pro
             195                 200                205

Ser Asn Thr Lys Val Asp Lys Lys Val Glu Pro Lys Ser Cys Asp Lys
         210                 215                 220

Thr His Thr Cys Pro Pro Cys Pro Ala Pro Glu Leu Leu Gly Gly Pro
225                 230                 235                240

Ser Val Phe Leu Phe Pro Pro Lys Pro Lys Asp Thr Leu Met Ile Ser
                 245                 250                255

Arg Thr Pro Glu Val Thr Cys Val Val Val Asp Val Ser His Glu Asp
             260                 265                270

Pro Glu Val Lys Phe Asn Trp Tyr Val Asp Gly Val Glu Val His Asn
             275                 280                285

Ala Lys Thr Lys Pro Arg Glu Glu Gln Tyr Ala Ser Thr Tyr Arg Val
         290                 295                 300

Val Ser Val Leu Thr Val Leu His Gln Asp Trp Leu Asn Gly Lys Glu
305                 310                 315                320

Tyr Lys Cys Lys Val Ser Asn Lys Ala Leu Pro Ala Pro Ile Glu Lys
                 325                 330                335

Thr Ile Ser Lys Ala Lys Gly Gln Pro Arg Glu Pro Gln Val Tyr Thr
             340                 345                350

Leu Pro Pro Ser Arg Asp Glu Leu Thr Lys Asn Gln Val Ser Leu Thr
             355                 360                365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                400

Asp Ser Asp Gly Ser Phe Phe Leu Tyr Ser Lys Leu Thr Val Asp Lys
                 405                 410                415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 25
<211> LENGTH: 95
<212> TYPE: PRT
<213> ORGANISM: Homo sapiens

<400> SEQUENCE: 25

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro
                 85                  90                  95

<210> SEQ ID NO 26
<211> LENGTH: 95
<212> TYPE: PRT
<213> ORGANISM: Homo sapiens

<400> SEQUENCE: 26

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Gly Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Pro Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp His
                 85                  90                  95

<210> SEQ ID NO 27
<211> LENGTH: 95
<212> TYPE: PRT
<213> ORGANISM: Homo sapiens

<400> SEQUENCE: 27

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                 85                  90                  95

<210> SEQ ID NO 28
<211> LENGTH: 95
<212> TYPE: PRT
<213> ORGANISM: Homo sapiens

<400> SEQUENCE: 28

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Arg Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                 85                  90                  95

<210> SEQ ID NO 29
<211> LENGTH: 95
<212> TYPE: PRT
<213> ORGANISM: Homo sapiens

<400> SEQUENCE: 29

Ala Ile Arg Met Thr Gln Ser Pro Phe Ser Leu Ser Ala Ser Val Gly
  1               5                  10                  15

Asp Arg Val Thr Ile Thr Cys Trp Ala Ser Gln Gly Ile Ser Ser Tyr
                 20                  25                  30

Leu Ala Trp Tyr Gln Gln Lys Pro Ala Lys Ala Pro Lys Leu Phe Ile
             35                  40                  45

Tyr Tyr Ala Ser Ser Leu Gln Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Tyr Ser Thr Pro
                 85                  90                  95

<210> SEQ ID NO 30
<211> LENGTH: 95
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95
```

<210> SEQ ID NO 31
<211> LENGTH: 95
<212> TYPE: PRT
<213> ORGANISM: Homo sapiens

<400> SEQUENCE: 31

```
Asp Ile Gln Met Thr Gln Ser Pro Ser Phe Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Cys Gly Tyr Ser Thr Pro
                 85                  90                  95
```

<210> SEQ ID NO 32
<211> LENGTH: 95
<212> TYPE: PRT
<213> ORGANISM: Homo sapiens

<400> SEQUENCE: 32

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95
```

<210> SEQ ID NO 33
<211> LENGTH: 95
<212> TYPE: PRT
<213> ORGANISM: Homo sapiens

<400> SEQUENCE: 33

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
```

```
                65                  70                  75                  80
Glu Asp Val Ala Thr Tyr Tyr Cys Gln Lys Tyr Asn Ser Ala Pro
                    85                  90                  95

<210> SEQ ID NO 34
<211> LENGTH: 95
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 35
<211> LENGTH: 95
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Asn Ser Tyr Pro
                85                  90                  95

<210> SEQ ID NO 36
<211> LENGTH: 95
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro
                85                  90                  95

<210> SEQ ID NO 37
<211> LENGTH: 95
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
  1               5                  10                  15

Asp Arg Val Thr Ile Thr Cys Arg Ala Arg Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                85                  90                  95

<210> SEQ ID NO 38
<211> LENGTH: 95
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                85                  90                  95

<210> SEQ ID NO 39
<211> LENGTH: 95
<212> TYPE: PRT
<213> ORGANISM: Homo sapiens

<400> SEQUENCE: 39

Asp Ile Gln Met Thr Gln Ser Pro Ser Val Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80
```

```
Glu Asp Phe Ala Thr Tyr Tyr Cys Gln Gln Ala Asn Ser Phe Pro
            85                  90                  95

<210> SEQ ID NO 40
<211> LENGTH: 95
<212> TYPE: PRT
<213> ORGANISM: Homo sapiens

<400> SEQUENCE: 40

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
            85                  90                  95

<210> SEQ ID NO 41
<211> LENGTH: 95
<212> TYPE: PRT
<213> ORGANISM: Homo sapiens

<400> SEQUENCE: 41

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
            85                  90                  95

<210> SEQ ID NO 42
<211> LENGTH: 95
<212> TYPE: PRT
<213> ORGANISM: Homo sapiens

<400> SEQUENCE: 42

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
```

<210> SEQ ID NO 43
<211> LENGTH: 95
<212> TYPE: PRT
<213> ORGANISM: Homo sapiens

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 44

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
            100                 105

<210> SEQ ID NO 45
<211> LENGTH: 96
<212> TYPE: PRT
<213> ORGANISM: Homo sapiens

<400> SEQUENCE: 45

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
50                  55                  60

```
Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95
```

<210> SEQ ID NO 46
<211> LENGTH: 100
<212> TYPE: PRT
<213> ORGANISM: Homo sapiens

<400> SEQUENCE: 46

```
Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
             35                  40                  45

Trp Leu Ala His Ile Phe Ser Asn Asp Glu Lys Ser Tyr Ser Thr Ser
 50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100
```

<210> SEQ ID NO 47
<211> LENGTH: 100
<212> TYPE: PRT
<213> ORGANISM: Homo sapiens

<400> SEQUENCE: 47

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Met Cys Val Ser Trp Ile Arg Gln Pro Pro Gly Lys Ala Leu Glu
             35                  40                  45

Trp Leu Ala Leu Ile Asp Trp Asp Asp Asp Lys Tyr Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100
```

<210> SEQ ID NO 48
<211> LENGTH: 99
<212> TYPE: PRT
<213> ORGANISM: Homo sapiens

<400> SEQUENCE: 48

```
Gln Leu Gln Leu Gln Glu Ser Gly Ser Gly Leu Val Lys Pro Ser Gln
 1               5                  10                  15

Thr Leu Ser Leu Thr Cys Ala Val Ser Gly Gly Ser Ile Ser Ser Gly
                 20                  25                  30
```

```
Gly Tyr Ser Trp Ser Trp Ile Arg Gln Pro Gly Lys Gly Leu Glu
            35                  40                  45

Trp Ile Gly Tyr Ile Tyr His Ser Gly Ser Thr Tyr Tyr Asn Pro Ser
 50                  55                  60

Leu Lys Ser Arg Val Thr Ile Ser Val Asp Arg Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 49
<211> LENGTH: 99
<212> TYPE: PRT
<213> ORGANISM: Homo sapiens

<400> SEQUENCE: 49

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln Pro Pro Gly Lys Gly Leu Glu
            35                  40                  45

Trp Ile Gly Tyr Ile Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 50
<211> LENGTH: 99
<212> TYPE: PRT
<213> ORGANISM: Homo sapiens

<400> SEQUENCE: 50

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Leu Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 51
<211> LENGTH: 99
<212> TYPE: PRT
<213> ORGANISM: Homo sapiens

<400> SEQUENCE: 51

Gln Leu Gln Leu Gln Glu Ser Gly Pro Gly Leu Val Lys Pro Ser Glu
```

```
                 1               5                   10                  15
Thr Leu Ser Leu Thr Cys Thr Val Ser Gly Gly Ser Ile Ser Ser Ser
                    20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
 65                 70                  75                  80

Ser Leu Lys Leu Ser Ser Val Thr Ala Ala Asp Thr Ala Val Tyr Tyr
                    85                  90                  95

Cys Ala Arg

<210> SEQ ID NO 52
<211> LENGTH: 99
<212> TYPE: PRT
<213> ORGANISM: Homo sapiens

<400> SEQUENCE: 52

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Val Ser Ser Gly
                    20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Ser Lys Asn Gln Phe
 65                 70                  75                  80

Ser Leu Lys Leu Ser Ser Val Thr Ala Ala Asp Thr Ala Val Tyr Tyr
                    85                  90                  95

Cys Ala Arg

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 53

Gln Val Thr Leu Arg Glu Ser Gly Pro Ala Leu Val Lys Pro Thr Gln
 1               5                   10                  15

Thr Leu Thr Leu Thr Cys Thr Phe Ser Gly Phe Ser Leu Ser Thr Ser
                    20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Asp Lys Tyr Tyr Asn Pro Ser
        50                  55                  60

Leu Lys Ser Arg Leu Thr Ile Ser Lys Asp Thr Ser Lys Asn Gln Val
 65                 70                  75                  80

Val Leu Thr Met Thr Asn Met Asp Pro Val Asp Thr Ala Thr Tyr Tyr
                    85                  90                  95

Cys Ala Arg Thr Arg Arg Tyr Phe Pro Phe Ala Tyr Trp Gly Gln Gly
                100                 105                 110
```

Thr Leu Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 54

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Lys Tyr Tyr Gln Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

<210> SEQ ID NO 55
<211> LENGTH: 330
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 55

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 56
<211> LENGTH: 330
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 56

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Ala Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 58
<211> LENGTH: 214
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 58

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Thr Asp Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
     195                 200                 205

Phe Asn Arg Gly Glu Cys
    210

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      amino acid leader sequence

<400> SEQUENCE: 59

Met Glu Thr Gln Ser Gln Val Phe Val Tyr Met Leu Leu Trp Leu Ser
  1               5                  10                  15

Gly Val Asp Gly
         20

<210> SEQ ID NO 60
<211> LENGTH: 449
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 60

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Gly Val Gly Trp Ile Arg Gln Pro Pro Gly Lys Ala Leu Glu
             35                  40                  45

Trp Leu Ala His Ile Trp Trp Asp Asp Asp Lys Tyr Tyr Asn Pro Ser
     50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

```
Cys Ala Arg Thr Arg Arg Tyr Phe Pro Phe Ala Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 61
<211> LENGTH: 449
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 61
```

-continued

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Gly Val Gly Trp Ile Arg Gln Pro Pro Gly Lys Ala Leu Glu
         35                  40                  45

Trp Leu Ala His Ile Trp Trp Asp Asp Lys Tyr Tyr Asn Pro Ser
     50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Thr Arg Arg Tyr Phe Pro Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 62
<211> LENGTH: 449
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 62

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Gln Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 63
<211> LENGTH: 449
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 63

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Gln Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      leader sequence peptide

<400> SEQUENCE: 64

Met Asp Arg Leu Thr Phe Ser Phe Leu Leu Leu Ile Val Pro Ala Tyr
  1               5                  10                  15

Val Leu Ser

<210> SEQ ID NO 65
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cacatttggt gggatgatga taagtactat caaccatccc tgaagagcca                50

<210> SEQ ID NO 66
<211> LENGTH: 138
<212> TYPE: PRT
<213> ORGANISM: Mus musculus
```

<400> SEQUENCE: 66

Met Asp Arg Leu Thr Phe Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Lys Tyr Tyr
65                  70                  75                  80

Gln Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Ala Ala
            100                 105                 110

Thr Tyr Tyr Cys Ala Arg Thr Arg Arg Tyr Phe Pro Phe Ala Tyr Trp
        115                 120                 125

Gly Gln Gly Thr Leu Val Thr Val Ser Ser
130                 135

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 67

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Asn Pro Ser Leu
    50                  55                  60

Lys Ser Arg Leu Thr Ile Ser Lys Asp Thr Ser Asn Gln Val Phe
65                  70                  75                  80

Leu Lys Ile Thr Ser Val Asp Thr Arg Asp Thr Ala Thr Tyr Tyr Cys
                85                  90                  95

Ala Arg Thr Arg Arg Tyr Phe Pro Phe Ala Tyr Trp Gly Glu Gly Thr
            100                 105                 110

Ser Val Thr Val Thr Ser
        115

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 68

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser

-continued

```
                    20                  25                  30
Gly Met Gly Val Gly Trp Ile Arg Gln Pro Pro Gly Lys Ala Leu Glu
            35                  40                  45

Trp Leu Ala His Ile Trp Trp Asp Asp Asp Lys Tyr Asn Pro Ser Leu
         50                  55                  60

Lys Ser Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                 85                  90                  95

Ala Arg Thr Arg Arg Tyr Phe Pro Phe Ala Tyr Trp Gly Gln Gly Thr
            100                 105                 110

Leu Val Thr Val Ser Ser
            115

<210> SEQ ID NO 69
<211> LENGTH: 6
<212> TYPE: PRT
<213> ORGANISM: Homo sapiens

<400> SEQUENCE: 69

Tyr Tyr Cys Ala His Arg
 1               5
```